US006605588B1

(12) United States Patent
Lees et al.

(10) Patent No.: US 6,605,588 B1
(45) Date of Patent: Aug. 12, 2003

(54) LOW DENSITY LIPOPROTEIN BINDING PROTEINS AND THEIR USE IN DIAGNOSING AND TREATING ATHEROSCLEROSIS

(75) Inventors: Ann M. Lees, Brookline, MA (US); Robert S. Lees, Brookline, MA (US); Simon W. Law, Lexington, MA (US); Anibal A. Arjona, Boston, MA (US)

(73) Assignee: Boston Heart Foundation, Inc., Cambridge, MA (US)

( * ) Notice: Subject to any disclaimer, the term of this patent is extended or adjusted under 35 U.S.C. 154(b) by 0 days.

(21) Appl. No.: 09/517,849

(22) Filed: Mar. 2, 2000

Related U.S. Application Data

(63) Continuation-in-part of application No. 08/979,608, filed on Nov. 26, 1997, now Pat. No. 6,355,451.
(60) Provisional application No. 60/048,547, filed on Jun. 3, 1997, and provisional application No. 60/031,930, filed on Nov. 27, 1996.

(51) Int. Cl.[7] ............................................. A01N 37/18
(52) U.S. Cl. ........................... 514/2; 424/185.1; 435/6; 435/7.1; 435/69.1; 530/350; 514/814
(58) Field of Search ........................... 435/7.1, 6, 69.1; 530/350; 514/2, 814; 424/185.1

(56) References Cited

U.S. PATENT DOCUMENTS

| | | | |
|---|---|---|---|
| 4,660,563 A | 4/1987 | Lees ........................... | 128/654 |
| 4,877,599 A | 10/1989 | Lees ........................... | 424/1.1 |
| 5,196,324 A | 3/1993 | Bumol et al. ............. | 435/70.21 |
| 5,665,872 A | 9/1997 | Saito et al. ................. | 536/23.5 |
| 5,726,153 A | 3/1998 | Lees et al. .................... | 514/12 |

FOREIGN PATENT DOCUMENTS

| | | |
|---|---|---|
| EP | 0 586 094 A1 | 3/1994 |
| EP | 0773290 A2 | 5/1997 |
| JP | 59206046 | 11/1984 |
| WO | WO 91/06011 | 5/1991 |
| WO | WO 91/16919 | 11/1991 |
| WO | WO 94/16074 | 7/1994 |
| WO | WO 98/23282 | 6/1998 |

OTHER PUBLICATIONS

Machesky et al. Mammalian actin–related protein 2/3 complex localizes to regions of lamellipodial protrusion and is composed of evolutionarily conserved proteins, Jul. 1997, Biochem. J. vol. 328, pp. 105–112.*
Kuzmenko et al., "Characteristics of Smooth Muscle Cell Lipoprotein Binding Proteins (p105/p130) as T–Cadherin and Regulation by Positive and Negative Growth Regulators," Biochemical And Biophysical Research Communications, 246:489–494 (1998).
Tkachuk et al., "Identification of an atypical lipoprotein-–binding protein from human aortic smooth muscle as T–cadherin," FEBS Letters, 421:208–212 (1998).
Ambrus et al., "Identification of a cDNA for a human high–molecular–weight B–cell growth factor," PNAS 93:8154 (1996).
Lee et al., "Nucleotide sequence of the rat low density lipoportein receptor cDNA," Nucleic Acids Res. 17(3):1259–1260 (1989).
Lees et al., "$^{99m}$ Technetium–labeled low density lipoprotein: receptor recognition and intracellular sequestration of radiolabel," Journal of Lipid Research, 32(1):1–8 (1991).
Yang et al., "Protein farnesyltransferase in plants. Molecular cloning and expression of a homolog of the beta subunit from the garden pea," Plant Physiol. 101:667–674 (1993).
GenBank™ Accession No. AA287095 (Aug. 14, 1997).
GenBank™ Accession No. R76498 (Jun. 6, 1995).
GenBank™ Accession No. W07246 (Apr. 25, 1996).
Accession AF006088, GenBank, Dec. 15, 1999.
Accession AF017807, GenBank, Sep. 18, 1997.
Accession AL022098, GenBank, Nov. 23, 1999.
Accession AL049795, GenBank, Feb. 18, 2000.
Accession AL137800, GenBank, Jun. 20, 2000.
Accession L15344, GenBank, May 25, 1995.
Accession NM005717, GenBank, Jun. 9, 1999.
Ambrus, Jr. et al., "Identification of a cDNA for a human high–molecular–weight B–cell growth factor," Proc. Natl. Acad. Sci. USA, 90:6630–6334, (Jul. 1993).
Camejo et al., "Characterization and Properties of a Lipoprotein–Complexing Proteoglycan from Human Aorta," Atherosclerosis, 35:307–320, (1980).
Chang et al., "Low–Density Lipoprotein Modification and Arterial Wall accumulation In a Rabbit Model of Atherosclerosis," Biochemistry, 32(33):8518–8524, (1993).
Chang et al., "Time Course of $^{125}$I–Labeled LDL Accumulation in the Healing, Balloon–Deendothelialized Rabbit Aorta," Arteriosclerosis and Thrombosis, 12(9):1088–1098, (Sep. 1992).
Davies, "Flow–Mediated Endothelial Mechanotransduction," Physiological Reviews, 75(3):519–560, (Jul. 1995).
de Rijke et al., "Rat Liver Kupffer and Endothelial Cells Express Different Binding Proteins for Modified Low Density Lipoproteins," The Journal of Biological Chemistry, 269(2):824–827, (Jan. 14, 1994).

(List continued on next page.)

*Primary Examiner*—Christopher S. F. Low
*Assistant Examiner*—Holly Schnizer
(74) *Attorney, Agent, or Firm*—Fish & Richardson P.C.

(57) ABSTRACT

Isolated polynucleotides encoding novel polypeptides which are capable of binding to native and methylated LDL (low density lipoprotein), the isolated polypeptides, called LBPs (LDL binding proteins), and biologically active fragments and analogs thereof, are described. Also described are methods for determining if an animal is at risk for atherosclerosis, methods for evaluating an agent for use in treating atherosclerosis, methods for treating atherosclerosis, and methods for treating a cell having an abnormality in structure or metabolism of LBP. Pharmaceutical compositions and vaccine compositions are also provided.

22 Claims, 35 Drawing Sheets

OTHER PUBLICATIONS

DePaola et al., "Vascular Endothelium Responds to Fluid Shear Stress Gradients," Arteriosclerosis and Thrombosis, 12(11):1254–1257, (Nov. 1992).

Esterbauer et al., "The Role of Lipid Peroxidation and Antioxidants In Oxidative Modification of LDL," Free Radical Biology & Medicine, 13:341–390, (1992).

Fischman et al., "Accumulation of Native and Methylated Low Density Lipoproteins by Healing Rabbit Arterial Wall," Arteriosclerosis, 7(4):361–366, (Jul./Aug. 1987).

Gimbrone, Jr. et al., "Vascular Endothelium An Integrator of Pathophysiological Stimuli in Atherogenesis," Annals New York Academy of Sciences, 748:122–131, (1995).

Gofman et al., "Blood Lipids and Human Atherosclerosis," The Journal of the American Heart Association, II(2):161–178, (Aug. 1950).

Hoff et al., "Apolipoprotein B Retention in the Grossly Normal and Atherosclerotic Human Aorta," Circulation Research, 41(5):684–690, (Nov. 1977).

Hoff et al., "Detergent Extraction of Tightly–Bound apoB from Extracts of Normal Aortic Intima and Plaques," Experimental and Molecular Pathology, 28:290–300, (1978).

Lees et al.,. "Imaging Human Atherosclerosis with $^{99m}$Tc–labeled Low Density Lipoproteins," Arteriosclerosis, 8(5):461–470, (Sep./Oct. 1988).

Minick et al., "Role of Endothelium and Hypercholesterolemia in Intimal Thickening and Lipid Accumulation," American Journal of Pathology, 95(1):131–151, Figs. 1–7, (Apr. 1979).

Morel et al., "Endothelial and Smooth Muscle Cells Alter Low Density Lipoprotein In Vitro by Free Radical Oxidation," Arteriosclerosis, 4(4):357–364, (Jul./Aug. 1984).

Nielsen, "Transfer of Low Density Lipoprotein Into the Arterial Wall and Risk of Atherosclerosis," Atherosclerosis, 123:1–15, (1996).

Nievelstein et al., "Lipid accumulation in Rabbit Aortic Intima 2 Hours After Bolus Infusion of Low Density Lipoprotein," Arteriosclerosis and Thrombosis, 11(6):1795–1805, (Nov./Dec. 1991).

Ramprasad et al., "Cell Surface Expression of Mouse Macrosialin and Human CD68 and Their Role As Macrophage Receptors for Oxidized Low Density Lipoprotein," Proc. Natl. Acad. Sci. USA, 93:14833–14838, (Dec. 1996).

Roberts et al., "Selective Accumulation of Low Density Lipoproteins In Damaged Arterial Wall," Journal of Lipid Research, 24:1160–1167, (1983).

Scandinavian Simvastatin Survival Study Group, Randomised Trial of Cholesterol Lowering in 4444 Patients with Coronary Heart Disease: the Scandinavian Simvastatin Survival Study (4S), The Lancet, 344:1383–1389, (Nov. 19, 1994).

Schwenke et al., "Initiation of Atherosclerotic Lesions in Cholesterol–fed Rabbits," Arteriosclerosis, 9(6):895–907, (Nov./Dec. 1989).

Schwenke et al., "Initiation of Atherosclerotic Lesions in Cholesterol–fed Rabbits," Arteriosclerosis, 9(6):908–918, (Nov./Dec. 1989).

Shepherd et al., "Prevention of Coronary Heart Disease with Pravastatin In Men with Hypercholesterolemia," The New England Journal of Medicine, 333(20):1301–1307, (Nov. 16, 1995).

Shih, "Focal Accumulation of An Apolipoprotein B–based Synthetic Oligopeptide in the Healing Rabbit Arterial Wall," Proc. Natl. Acad. Sci. USA, 87:1436–1440, (Feb. 1990).

Sigma Chemical Company, Biochemicals Organic Compounds for Research and Diagnostic Reagents, p. 1906 (1995).

Smith, "The Relationship Between Plasma and Tissue Lipids in human Atherosclerosis," Adv. Lipid Res., 12:1–49, (1974).

Srinivasan et al., "Isolation of Lipoprotein–Acid Mucopolysaccharide Complexes from Fatty Streaks of Human Aortas," Atherosclerosis, 16:95–104, (1972).

Stamler et al., "Is Relationship Between Serum Cholesterol and Risk of Premature Death From Coronary Heart Disease Continuous and Graded?," JAMA, 256(20):2823–2828, (Nov. 28, 1986).

Stampfer et al., "A Prospective Study of Cholesterol, Apolipoproteins, and the Risk of Myocardial Infarction," New England Journal of Medicine, 325:373–381, (Aug. 8, 1991).

Stary et al., "A Definition of Initial, Fatth Streak, and Intermediate Lesions of Atherosclerosis," Arteriosclerosis and Thrombosis, 14(5):840–856, (May 1994).

Steinberg et al., "Beyond Cholesterol Modifications of Low–Density Lipoprotein That Increase Its Atherogenicity," The New England Journal of Medicine, 320(14):915–924, (Apr. 6, 1989).

Steinbrecher et al., "Modification of Low Density Lipoprotein By Endothelial Cells Involves Lipid Peroxidation and Degradation of Low Density Lipoprotein Phospholipids," Proc. Natl. Acad. Sci. USA, 81:3883–3887, (Jun. 1984).

Weisgraber et al., "Role of the Lysine Residues of Plasma Lipoproteins in High Affinity Binding to Cell Surface Receptors on Human Fibroblasts," The Journal of Biological Chemistry, 253:9053–9062, (1978).

Welch et al., "Actin Polymerization is Induced by Arp2/3 Protein Complex at the Surface of Listeria Monocytogenes," Nature, 385:265–269, (Jan. 16, 1997).

Welch et al., "The Human Arp2/3 Complex Is Composed of Evolutionarily Conserved Subunits and Is Localized to Cellular Regions of Dynamic Actin Filament Assembly," The Journal of Cell Biology, 138(2):375–384, (Jul. 28, 1997).

Williams, "The Response–to–Retention Hypothesis of Early Atherogenesis," Arteriosclerosis, Thrombosis, and Vascular Biology, 15(5):551–561, (May 1995).

* cited by examiner met ser lys asn thr
val ser ser ala arg phe arg lys val asp val asp
glu tyr asp glu asn lys phe val asp glu glu asp
gly gly asp gly gln ala gly pro asp glu gly glu
val asp ser cys leu arg gln gly asn met thr ala
ala leu gln ala ala leu lys asn pro pro ile asn
thr arg ser gln ala val lys asp arg ala gly ser
ile val leu lys val leu ile ser phe lys ala gly
asp ile glu lys ala val gln ser leu asp arg asn
gly val asp leu leu met lys tyr ile tyr lys gly
phe glu ser pro ser asp asn ser ser ala val leu
leu gln trp his glu lys ala leu ala ala gly gly val gly ser ile val arg val leu thr ala arg lys thr val

FIG. 1 asp cys arg ser ser ser asn asn arg Xaa pro lys
gly gly ala ala arg ala gly gly pro ala arg pro
val ser leu arg glu val val arg tyr leu gly gly
ser ser gly ala gly gly arg leu thr arg gly arg
val gln gly leu leu glu glu glu ala ala ala arg
gly arg leu glu arg thr arg leu gly ala leu ala
leu pro arg gly asp arg pro gly arg ala pro pro
ala ala ser ala arg ala ala arg asn lys arg ala
gly glu glu arg val leu glu lys glu glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly

FIG. 2 ala ser ala arg ala ala arg asn lys arg ala
gly glu glu arg val leu glu lys glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly

FIG. 3

```
                              thr arg leu gly ala leu ala
leu pro arg gly asp arg pro gly arg ala pro pro
ala ala ser ala arg ala ala arg asn lys arg ala
gly glu glu arg val leu glu lys glu glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly
```

FIG. 4

```
                                        met lys asn gln
asp lys lys asn gly ala ala lys gln pro asn pro
lys ser ser pro gly gln pro glu ala gly ala glu
gly ala gln gly arg pro gly arg pro ala pro ala
arg glu ala glu gly ala ser ser gln ala pro gly
arg pro glu gly ala gln ala lys thr ala gln pro
gly ala leu cys asp val ser glu glu leu ser arg
gln leu glu asp ile leu ser thr tyr cys val asp
asn asn gln gly ala pro gly glu asp gly val gln
gly glu pro pro glu pro glu asp ala glu lys ser
arg ala tyr val ala arg asn gly glu pro glu pro
gly thr pro val val asn gly glu lys glu thr ser
lys ala glu pro gly thr glu glu ile arg thr ser
asp glu val gly asp arg asp his arg arg pro gln
glu lys lys lys ala lys gly leu gly lys glu ile
thr leu leu met gln thr leu asn thr leu ser thr
pro glu glu lys leu ala ala leu cys lys lys tyr
ala glu leu leu glu glu his arg asn ser gln lys
gln met lys leu leu gln lys lys gln ser gln leu
val gln glu lys asp his leu arg gly glu his ser
lys ala ile leu ala arg ser lys leu glu ser leu
cys arg glu leu gln arg his asn arg ser leu lys
glu glu gly val gln arg ala arg glu glu glu glu
lys arg lys glu val thr ser his phe gln met thr
leu asn asp ile gln leu gln met glu gln his asn
glu arg asn ser lys leu arg gln glu asn met glu
```

FIG. 5A leu ala glu arg leu lys lys leu ile glu gln tyr
glu leu arg glu glu his ile asp lys val phe lys
his lys asp leu gln gln gln leu val asp ala lys
leu gln gln ala gln glu met leu lys glu ala glu
glu arg his gln arg glu lys asp phe leu leu lys
glu ala val glu ser gln arg met cys glu leu met
lys gln gln glu thr his leu lys gln gln leu ala
leu tyr thr glu lys phe glu glu phe gln asn thr
leu ser lys ser ser glu val phe thr thr phe lys
gln glu met glu lys met thr lys lys ile lys lys
leu glu lys glu thr thr met tyr arg ser arg trp
glu ser ser asn lys ala leu leu glu met ala glu
glu lys thr leu arg asp lys glu leu glu gly leu
gln val lys ile gln arg leu glu lys leu cys arg
ala leu gln thr glu arg asn asp leu asn lys arg
val gln asp leu ser ala gly gly gln gly pro val
ser asp ser gly pro glu arg arg pro glu pro ala
thr thr ser lys glu gln gly val glu gly pro gly
ala gln val pro asn ser pro arg ala thr asp ala
ser cys cys ala gly ala pro ser thr glu ala ser
gly gln thr gly pro gln glu pro thr thr ala thr
ala

FIG. 5B

```
                    met ser lys asn thr val ser ser ala
arg phe arg lys val asp val asp glu tyr asp glu
asn lys phe val asp glu glu asp gly gly asp gly
gln ala gly pro asp glu gly glu val asp ser cys
leu arg gln gly asn met thr ala ala leu gln ala
ala leu lys asn pro pro ile asn thr lys ser gln
ala val lys asp arg ala gly ser ile val leu lys
val leu ile ser phe lys ala asn asp ile glu lys
ala val gln ser leu asp lys asn gly val asp leu
leu met lys tyr ile tyr lys gly phe glu ser pro
ser asp asn ser ser ala met leu leu gln trp his
glu lys ala leu ala ala gly gly val gly ser ile
val arg val leu thr ala arg lys thr val
```

FIG. 6 glu glu arg val leu glu lys glu glu glu glu asp
asp asp glu asp glu asp glu glu asp asp val ser
glu gly ser glu val pro glu ser asp arg pro ala
gly ala gln his his gln leu asn gly glu arg gly
pro gln ser ala lys glu arg val lys glu trp thr
pro cys gly pro his gln gly gln asp glu gly arg
gly pro ala pro gly ser gly thr arg gln val phe
ser met ala ala met asn lys glu gly gly thr ala
ser val ala thr gly pro asp ser pro ser pro val
pro leu pro pro gly lys pro ala leu pro gly ala
asp gly thr pro phe gly cys pro pro gly arg lys
glu lys pro ser asp pro val glu trp thr val met
asp val val glu tyr phe thr glu ala gly phe pro
glu gln ala thr ala phe gln glu gln glu ile asp
gly lys ser leu leu leu met gln arg thr asp val
leu thr gly leu ser ile arg leu gly pro ala leu
lys ile tyr glu his his ile lys val leu gln gln
gly his phe glu asp asp asp pro asp gly phe leu
gly

FIG. 7 lys ser ser pro gly gln pro glu ala gly pro glu gly ala
gln glu arg pro ser gln ala ala pro ala val glu ala glu gly
pro gly ser ser gln ala pro arg lys pro glu gly ala gln ala
arg thr ala gln ser gly ala leu arg asp val ser glu glu leu
ser arg gln leu glu asp ile leu ser thr tyr cys val asp asn
asn gln gly gly pro gly glu asp gly ala gln gly glu pro ala
glu pro glu asp ala glu lys ser arg thr tyr val ala arg asn
gly glu pro glu pro thr pro val val tyr gly glu lys glu pro
ser lys gly asp pro asn thr glu glu ile arg gln ser asp glu
val gly asp arg asp his arg arg pro gln glu lys lys lys ala
lys gly leu gly lys glu ile thr leu leu met gln thr leu asn
thr leu ser thr pro glu glu lys leu ala ala leu cys lys lys
tyr ala glu leu leu glu glu his arg asn ser gln lys gln met
lys leu leu gln lys lys gln ser gln leu val gln glu lys asp
his leu arg gly glu his ser lys ala val leu ala arg ser lys
leu glu ser leu cys arg glu leu gln arg his asn arg ser leu
lys glu glu gly val gln arg ala arg glu glu glu glu lys arg
lys glu val thr ser his phe gln val thr leu asn asp ile gln
leu gln met glu gln his asn glu arg asn ser lys leu arg gln
glu asn met glu leu ala glu arg leu lys lys leu ile glu gln
tyr glu leu arg glu glu his ile asp lys val phe lys his lys
asp leu gln gln gln leu val asp ala lys leu gln gln ala gln
glu met leu lys glu ala glu glu arg his gln arg glu lys asp
phe leu leu lys glu ala val glu ser gln arg met cys glu leu
met lys gln gln glu thr his leu lys gln gln leu ala leu tyr
thr glu lys phe glu glu phe gln asn thr leu ser lys ser ser

FIG. 8A glu val phe thr thr phe lys gln glu met glu lys met thr lys lys ile lys lys leu glu lys glu thr thr met tyr arg ser arg trp glu ser ser asn lys ala leu leu glu met ala glu glu lys thr val arg asp lys glu leu glu gly leu gln val lys ile gln arg leu glu lys leu cys arg ala leu gln thr glu arg asn asp leu asn lys arg val gln asp leu ser ala gly gly gln gly ser leu thr asp ser gly pro glu arg arg pro glu gly pro gly ala gln ala pro ser ser pro arg val thr glu ala pro cys tyr pro gly ala pro ser thr glu ala ser gly gln thr gly pro gln glu pro thr ser ala arg ala ***

FIG. 8B val asp val asp glu tyr asp glu asn lys phe val asp glu glu asp gly gly asp gly

FIG. 9

```
  1  AAG CCT CGC AGC GGT CGG GGC GGC GCC GCG GAG GCT
 37  CGA GGG CGG CGG GCG GCG GCG ATG TCG AAG AAC ACG
                                 met ser lys asn thr 73  GTG TCG TCG GCG CGG TTC CGG AAG GTG GAC GTG GAT
     val ser ser ala arg phe arg lys val asp val asp 109  GAG TAC GAC GAG AAC AAG TTC GTG GAC GAG GAA GAC
     glu tyr asp glu asn lys phe val asp glu glu asp 145  GGC GGC GAC GGC CAG GCG GGG CCG GAC GAG GGC GAG
     gly gly asp gly gln ala gly pro asp glu gly glu 181  GTG GAC TCG TGC CTG CGG CAA GGG AAC ATG ACA GCC
     val asp ser cys leu arg gln gly asn met thr ala 217  GCC CTG CAG GCG GCG CTG AAG AAC CCT CCC ATC AAC
     ala leu gln ala ala leu lys asn pro pro ile asn 253  ACC AGG AGC CAG GCG GTG AAG GAC CGG GCA GGC AGC
     thr arg ser gln ala val lys asp arg ala gly ser 289  ATC GTG CTG AAG GTG CTC ATC TCC TTC AAG GCC GGC
     ile val leu lys val leu ile ser phe lys ala gly

325  GAC ATA GAA AAG GCC GTG CAG TCC CTG GAC AGG AAC
     asp ile glu lys ala val gln ser leu asp arg asn 361  GGC GTG GAC CTG CTC ATG AAG TAC ATC TAC AAG GGC
     gly val asp leu leu met lys tyr ile tyr lys gly 397  TTC GAG AGC CCC TCC GAC AAC AGC AGC GCC GTG CTC
     phe glu ser pro ser asp asn ser ser ala val leu 433  CTG CAG TGG CAC GAG AAG GCG CTG GCT GCA GGA GGA
     leu gln trp his glu lys ala leu ala ala gly gly 469  GTG GGC TCC ATC GTC CGT GTC CTG ACT GCA AGG AAA
     val gly ser ile val arg val leu thr ala arg lys 505  ACC GTG TAG CCT GGC AGG AAC GGG TGC CTG CCG GGG
     thr val
```

FIG. 10A

```
541   AGC GGG AGC TGC CGG TAC AAA GAC CAA AAC GCC CAG
577   ATG CCG CCG CTG CCC TGT GGG CGG CGT CTG TTC CCA
613   GCT TCG CTT TTT CCC TTT CCC GTG TCT GTC AGG ATT
649   ACA TAA GGT TTC CCT TCG TGA GAA TCG GAG TGG CGC
685   AGA GGG TCC TGT TCA TAC GCG CCG TGC GTC GGG CTG
721   TGT AAG ACC CCT GCC TTC AGT GTC CTT GAG CAA CGG
757   TAG CGT GTC GCC GGC TGG GTT TGG TTT TGT CGT GGA
793   GGG ATC TGG TCA GAA TTT GAG GCC AGT TTC CTA ACT
829   CAT TGC TGG TCA GGA AAT GAT CTT CAT TTA AAA AAA
865   AAA AAA AGA CTG GCA GCT ATT ATG CAA AAC TGG ACC
901   CTC TTC CCT TAT TTA AGC AGA GTG AGT TTC TGG AAC
937   CAG TGG TGC CCC CCC CCC CGC CCC GGC CGC CGT CCT
973   GCT CAA GGG AAG CCT CCC TGC AGA GCA GCA GAG CCC
1009  CTG GGC AGG AGC GCC GCG TCC CGC TCC CAG GAG ACA
1045  GCA TGC GCG GTC ACG CGG CAC TTC CTG TGC CTC CCA
1081  GCC CCA GTG CCC CGG AGT TCT TCA GGG CGA CAG GGA
1117  CCT CAG AAG ACT GGA TCC GAT CCA GAC AGA CGC CCA
1153  TTC TTG GTT CAG CTC AGT GTT TTC AAA AGG AAC GTG
1189  CTA CCG TGG GTA GAG CAC ACT GGT TCT CAG AAC ACG
1225  GCC GGC GCT TGA CGG TTG TCA CAG CTC CAG AAC AAA
1261  TCC TGG GAG ACA GGC GAG CGC GAG TCG CCG GGC AGG
1297  AAT TCC ACA CAC TCG TGC TGT TTT TGA TAC CTG CTT
1333  TTT GTT TTG TTT TGT AAA AAT GAT GCA CTT GAG AAA
1369  ATA AAA CGT CAG TGT TGA CAA AAA AAA AAA AAA
```

FIG. 10B

```
  1  GAC TGC CGC AGC AGC AGC AAC AAC CGC TAG CCG AAG
     asp cys arg ser ser ser asn asn arg Xaa pro lys 37  GGT GGC GCG GCG CGG GCC GGC GGC CCG GCG CGG CCC
     gly gly ala ala arg ala gly gly pro ala arg pro 73  GTG AGC CTG CGG GAA GTC GTG CGC TAC CTC GGG GGT
     val ser leu arg glu val val arg tyr leu gly gly 109  AGC AGC GGC GCT GGC GGC CGC CTG ACC CGC GGC CGC
     ser ser gly ala gly gly arg leu thr arg gly arg 145  GTG CAG GGT CTG CTG GAA GAG GAG GCG GCG GCG CGG
     val gln gly leu leu glu glu glu ala ala ala arg 181  GGC CGC CTG GAG CGC ACC CGT CTC GGA GCG CTT GCG
     gly arg leu glu arg thr arg leu gly ala leu ala 217  CTG CCC CGC GGG GAC AGG CCC GGA CGG GCG CCA CCG
     leu pro arg gly asp arg pro gly arg ala pro pro 253  GCC GCC AGC GCC CGC GCG GCG CGG AAC AAG AGA GCT
     ala ala ser ala arg ala ala arg asn lys arg ala 289  GGC GAG GAG CGA GTG CTT GAA AAG GAG GAG GAG GAG
     gly glu glu arg val leu glu lys glu glu glu glu 325  GAG GAG GAG GAA GAC GAC GAG GAC GAC GAC GAC GAC
     glu glu glu glu asp asp glu asp asp asp asp asp 361  GTC GTG TCC GAG GGC TCG GAG GTG CCC GAG AGC GAT
     val val ser glu gly ser glu val pro glu ser asp 397  CGT CCC GCG GGT GCG CAG CAT CAC CAG CTG AAT GGC
     arg pro ala gly ala gln his his gln leu asn gly 433  GGC GAG CGC GGC CCG CAG ACC GCC AAG GAG CGG GCC
     gly glu arg gly pro gln thr ala lys glu arg ala 469  AAG GAG TGG TCG CTG TGT GGC CCC CAC CCT GGC CAG
     lys glu trp ser leu cys gly pro his pro gly gln
```

FIG. 11A

```
505  GAG GAA GGG CGG GGG CCG GCC GCG GGC AGT GGC ACC
     glu glu gly arg gly pro ala ala gly ser gly thr 541  CGC CAG GTG TTC TCC ATG GCG GCC TTG AGT AAG GAG
     arg gln val phe ser met ala ala leu ser lys glu 577  GGG GGA TCA GCC TCT TCG ACC ACC GGG CCT GAC TCC
     gly gly ser ala ser ser thr thr gly pro asp ser 613  CCG TCC CCG GTG CCT TTG CCC CCC GGG AAG CCA GCC
     pro ser pro val pro leu pro pro gly lys pro ala 649  CTC CCA GGA GCC GAT GGG ACC CCC TTT GGC TGC CCT
     leu pro gly ala asp gly thr pro phe gly cys pro 685  GCC GGG CGC AAA GAG AAG CCG GCA GAC CCC GTG GAG
     ala gly arg lys glu lys pro ala asp pro val glu 721  TGG ACA GTC ATG GAC GTC GTG GAG TAC TTC ACC GAG
     trp thr val met asp val val glu tyr phe thr glu 757  GCG GGC TTC CCT GAG CAA GCC ACG GCT TTC CAG GAG
     ala gly phe pro glu gln ala thr ala phe gln glu 793  CAG GAG ATC GAC GGC AAG TCC CTG CTG CTC ATG CAG
     gln glu ile asp gly lys ser leu leu leu met gln 829  CGC ACC GAT GTC CTC ACC GGC CTG TCC ATC CGC CTG
     arg thr asp val leu thr gly leu ser ile arg leu 865  GGG CCA GCG TTG AAA ATC TAT GAG CAC CAT ATC AAG
     gly pro ala leu lys ile tyr glu his his ile lys 901  GTG CTG CAG CAG GGT CAC TTC GAG GAC GAT GAC CCG
     val leu gln gln gly his phe glu asp asp asp pro 937  GAA GGC TTC CTG GGA TGA GCA CAG AGC CGC CGC GCC
     glu gly phe leu gly 973  CCT TGT CCC CAC CCC CAC CCC GCC TGG ACC CAT TCC
1009 TGC CTC CAT GTC ACC CAA GGT GTC CCA GAG GCC AGG
1045 AGC TGG ACT GGG CAG GCG AGG GGT GCG GAC CTA CCC
1081 TGA TTC TGG TAG GGG GCG GGG CCT TGC TGT GCT CAT
```

FIG. 11B

```
1117  TGC TAC CCC CCC ACC CCG TGT GTG TCT CTG CAC CTG
1153  CCC CCA GCA CAC CCC TCC CGG AGC CTG GAT GTC GCC
1189  TGG GAC TCT GGC CTG CTC ATT TTG CCC CCA GAT CAG
1225  CCC CCT CCC TCC CTC CTG TCC CAG GAC ATT TTT TAA
1261  AAG AAA AAA AGG AAA AAA AAA AAT TGG GGA GGG GGC
1297  TGG GAA GGT GCC CCA AGA TCC TCC TCG GCC CAA CCA
1333  GGT GTT TAT TCC TAT ATA TAT ATA TAT ATG TTT TGT
1369  TCT GCC TGT TTT TCG TTT TTT GGT GCG TGG CCT TTC
1405  TTC CCT CCC ACC ACC ACT CAT GGC CCC AGC CCT GCT
1441  CGC CCT GTC GGC GGG AGC AGC TGG GAA TGG GAG GAG
1477  GGT GGG ACC TTG GGT CTG TCT CCC ACC CTC TCT CCC
1513  GTT GGT TCT GTT GTC GCT CCA GCT GGC TGT ATT GCT
1549  TTT TAA TAT TGC ACC GAA GGG TTG TTT TTT TTT TTT
1585  TAA ATA AAA TTT TAA AAA AAG GAA AAA AAA AAA
```

FIG. 11C

```
256   GCC AGC GCC CGC GCG GCG CGG AAC AAG AGA GCT
      ala ser ala arg ala ala arg asn lys arg ala 289   GGC GAG GAG CGA GTG CTT GAA AAG GAG GAG GAG
      gly glu glu arg val leu glu lys glu glu glu 325   GAG GAG GAG GAA GAC GAC GAG GAC GAC GAC GAC
      glu glu glu glu asp asp glu asp asp asp asp 361   GTC GTG TCC GAG GGC TCG GAG GTG CCC GAG AGC GAT
      val val ser glu gly ser glu val pro glu ser asp 397   CGT CCC GCG GGT GCG CAG CAT CAC CAG CTG AAT GGC
      arg pro ala gly ala gln his his gln leu asn gly 433   GGC GAG CGC GGC CCG CAG ACC GCC AAG GAG CGG GCC
      gly glu arg gly pro gln thr ala lys glu arg ala 469   AAG GAG TGG TCG CTG TGT GGC CCC CAC CCT GGC CAG
      lys glu trp ser leu cys gly pro his pro gly gln 505   GAG GAA GGG CGG GGG CCG GCC GCG GGC AGT GGC ACC
      glu glu gly arg gly pro ala ala gly ser gly thr 541   CGC CAG GTG TTC TCC ATG GCG GCC TTG AGT AAG GAG
      arg gln val phe ser met ala ala leu ser lys glu 577   GGG GGA TCA GCC TCT TCG ACC ACC GGG CCT GAC TCC
      gly gly ser ala ser ser thr thr gly pro asp ser 613   CCG TCC CCG GTG CCT TTG CCC CCC GGG AAG CCA GCC
      pro ser pro val pro leu pro pro gly lys pro ala 649   CTC CCA GGA GCC GAT GGG ACC CCC TTT GGC TGC CCT
      leu pro gly ala asp gly thr pro phe gly cys pro 685   GCC GGG CGC AAA GAG AAG CCG GCA GAC CCC GTG GAG
      ala gly arg lys glu lys pro ala asp pro val glu 721   TGG ACA GTC ATG GAC GTC GTG GAG TAC TTC ACC GAG
      trp thr val met asp val val glu tyr phe thr glu
```

FIG. 12A

```
757  GCG GGC TTC CCT GAG CAA GCC ACG GCT TTC CAG GAG
     ala gly phe pro glu gln ala thr ala phe gln glu 793  CAG GAG ATC GAC GGC AAG TCC CTG CTG CTC ATG CAG
     gln glu ile asp gly lys ser leu leu leu met gln 829  CGC ACC GAT GTC CTC ACC GGC CTG TCC ATC CGC CTG
     arg thr asp val leu thr gly leu ser ile arg leu 865  GGG CCA GCG TTG AAA ATC TAT GAG CAC CAT ATC AAG
     gly pro ala leu lys ile tyr glu his his ile lys 901  GTG CTG CAG CAG GGT CAC TTC GAG GAC GAT GAC CCG
     val leu gln gln gly his phe glu asp asp asp pro 937  GAA GGC TTC CTG GGA TGA GCA CAG AGC CGC CGC GCC
     glu gly phe leu gly 973  CCT TGT CCC CAC CCC CAC CCC GCC TGG ACC CAT TCC
1009 TGC CTC CAT GTC ACC CAA GGT GTC CCA GAG GCC AGG
1045 AGC TGG ACT GGG CAG GCG AGG GGT GCG GAC CTA CCC
1081 TGA TTC TGG TAG GGG GCG GGG CCT GCT GTG CTG CAT
1117 TGC TAC CCC CCC ACC CCG TGT GTG TCT CTG CAC CTG
1153 CCC CCA GCA CAC CCC TCC CGG AGC TGG ATG TCG CC
1189 TGG GAC TCT GGC CTG CTC ATT TTG CCC CCA GAT CAG
1225 CCC CCT CCC TCC CTC CTG TCC CAG GAC ATT TTT TAA
1261 AAG AAA AAA AGG AAA AAA AAA AAT TGG GGA GGG GGC
1297 TGG GAA GGT GCC CCA AGA TCC TCC TCG GCC AAC CA
1333 GGT GTT TAT TCC TAT ATA TAT ATA TAT ATG TTT TGT
1369 TCT GCC TGT TTT TCG TTT TTT GGT GCG TGG CCT TTC
1405 TTC CCT CCC ACC ACC ACT CAT GGC CCC AGC CCT GCT
1441 CGC CCT GTC GGC GGG AGC AGC TGG AAT GGG AGG AG
1477 GGT GGG ACC TTG GGT CTG TCT CCC ACC CTC TCT CCC
1513 GTT GGT TCT GTT GTC GCT CCA GCT GGC TGT ATT GCT
1549 TTT TAA TAT TGC ACC GAA GGG TTG TTT TTT TTT TTT
1585 TAA ATA AAA TTT TAA AAA AAG GAA AAA AAA AAA
```

FIG. 12B

```
196                     ACC CGT CTC GGA GCG CTT GCG
                        thr arg leu gly ala leu ala 217 CTG CCC CGC GGG GAC AGG CCC GGA CGG GCG CCA CCG
    leu pro arg gly asp arg pro gly arg ala pro pro 253 GCC GCC AGC GCC CGC GCG GCG CGG AAC AAG AGA GCT
    ala ala ser ala arg ala ala arg asn lys arg ala 289 GGC GAG GAG CGA GTG CTT GAA AAG GAG GAG GAG GAG
    gly glu glu arg val leu glu lys glu glu glu glu 325 GAG GAG GAG GAA GAC GAC GAG GAC GAC GAC GAC GAC
    glu glu glu glu asp asp glu asp asp asp asp asp 361 GTC GTG TCC GAG GGC TCG GAG GTG CCC GAG AGC GAT
    val val ser glu gly ser glu val pro glu ser asp 397 CGT CCC GCG GGT GCG CAG CAT CAC CAG CTG AAT GGC
    arg pro ala gly ala gln his his gln leu asn gly 433 GGC GAG CGC GGC CCG CAG ACC GCC AAG GAG CGG GCC
    gly glu arg gly pro gln thr ala lys glu arg ala 469 AAG GAG TGG TCG CTG TGT GGC CCC CAC CCT GGC CAG
    lys glu trp ser leu cys gly pro his pro gly gln 505 GAG GAA GGG CGG GGG CCG GCC GCG GGC AGT GGC ACC
    glu glu gly arg gly pro ala ala gly ser gly thr 541 CGC CAG GTG TTC TCC ATG GCG GCC TTG AGT AAG GAG
    arg gln val phe ser met ala ala leu ser lys glu 577 GGG GGA TCA GCC TCT TCG ACC ACC GGG CCT GAC TCC
    gly gly ser ala ser ser thr thr gly pro asp ser 613 CCG TCC CCG GTG CCT TTG CCC CCC GGG AAG CCA GCC
    pro ser pro val pro leu pro pro gly lys pro ala 649 CTC CCA GGA GCC GAT GGG ACC CCC TTT GGC TGC CCT
    leu pro gly ala asp gly thr pro phe gly cys pro
```

FIG. 13A

```
685  GCC GGG CGC AAA GAG AAG CCG GCA GAC CCC GTG GAG
     ala gly arg lys glu lys pro ala asp pro val glu 721  TGG ACA GTC ATG GAC GTC GTG GAG TAC TTC ACC GAG
     trp thr val met asp val val glu tyr phe thr glu 757  GCG GGC TTC CCT GAG CAA GCC ACG GCT TTC CAG GAG
     ala gly phe pro glu gln ala thr ala phe gln glu 793  CAG GAG ATC GAC GGC AAG TCC CTG CTG CTC ATG CAG
     gln glu ile asp gly lys ser leu leu leu met gln 829  CGC ACC GAT GTC CTC ACC GGC CTG TCC ATC CGC CTG
     arg thr asp val leu thr gly leu ser ile arg leu 865  GGG CCA GCG TTG AAA ATC TAT GAG CAC CAT ATC AAG
     gly pro ala leu lys ile tyr glu his his ile lys 901  GTG CTG CAG CAG GGT CAC TTC GAG GAC GAT GAC CCG
     val leu gln gln gly his phe glu asp asp asp pro 937  GAA GGC TTC CTG GGA TGA GCA CAG AGC CGC CGC GCC
     glu gly phe leu gly 973  CCT TGT CCC CAC CCC CAC CCC GCC TGG ACC CAT TCC
1009 TGC CTC CAT GTC ACC CAA GGT GTC CCA GAG GCC AGG
1045 AGC TGG ACT GGG CAG GCG AGG GGT GCG GAC CTA CCC
1081 TGA TTC TGG TAG GGG GCG GGG CCT TGC TGT GCT CAT
1117 TGC TAC CCC CCC ACC CCG TGT GTG TCT CTG CAC CTG
1153 CCC CCA GCA CAC CCC TCC CGG AGC TGG ATG TCG CC
1189 TGG GAC TCT GGC CTG CTC ATT TTG CCC CCA GAT CAG
1225 CCC CCT CCC TCC CTC CTG TCC CAG GAC ATT TTT TAA
1261 AAG AAA AAA AGG AAA AAA AAA AAT TGG GGA GGG GGC
1297 TGG GAA GGT GCC CCA AGA TCC TCC TCG GCC CAA CCA
1333 GGT GTT TAT TCC TAT ATA TAT ATA TAT ATG TTT TGT
1369 TCT GCC TGT TTT TCG TTT TTT GGT GCG TGG CCT TTC
1405 TTC CCT CCC ACC ACC ACT CAT GGC CCC AGC CCT GCT
1441 CGC CCT GTC GGC GGG AGC AGC TGG AAT GGA GAG GAG
1477 GGT GGG ACC TTG GGT CTG TCT CCC ACC CTC TCT CCC
1513 GTT GGT TCT GTT GTC GCT CCA GCT GGC TGT ATT GCT
1549 TTT TAA TAT TGC ACC GAA GGG TTG TTT TTT TTT TTT
1585 TAA ATA AAA TTT TAA AAA AAG GAA AAA AAA AAA
```

FIG. 13B

```
  1  GTG GAA AAT AGC AAC TGT GTT TCT CAA GGA TCC AAT
 37  CCC AAC CTA AGG TGG CAG CGC ACA ATG AAG AAT CAA
                                     met lys asn gln 73  GAC AAA AAG AAC GGG GCT GCC AAA CAG CCC AAC CCC
     asp lys lys asn gly ala ala lys gln pro asn pro 109  AAA AGC AGC CCG GGA CAG CCG GAA GCA GGA GCG GAG
     lys ser ser pro gly gln pro glu ala gly ala glu 145  GGA GCC CAG GGG CGG CCC GGC CGG CCG GCC CCC GCC
     gly ala gln gly arg pro gly arg pro ala pro ala 181  CGA GAA GCC GAA GGT GCC AGC AGC CAG GCT CCC GGG
     arg glu ala glu gly ala ser ser gln ala pro gly 217  AGG CCG GAG GGG GCT CAA GCC AAA ACT GCT CAG CCT
     arg pro glu gly ala gln ala lys thr ala gln pro 253  GGG GCG CTC TGT GAT GTC TCT GAG GAG CTG AGC CGC
     gly ala leu cys asp val ser glu glu leu ser arg 289  CAG TTG GAA GAC ATA CTC AGT ACA TAC TGT GTG GAC
     gln leu glu asp ile leu ser thr tyr cys val asp 325  AAC AAC CAG GGG GCC CCG GGT GAG GAT GGG GTC CAG
     asn asn gln gly ala pro gly glu asp gly val gln 361  GGT GAG CCC CCT GAA CCT GAA GAT GCA GAG AAG TCT
     gly glu pro pro glu pro glu asp ala glu lys ser 397  CGC GCC TAT GTG GCA AGG AAT GGG GAG CCG GAG CCG
     arg ala tyr val ala arg asn gly glu pro glu pro 433  GGC ACC CCA GTA GTC AAT GGC GAG AAG GAG ACC TCC
     gly thr pro val val asn gly glu lys glu thr ser 469  AAG GCA GAG CCG GGC ACG GAA GAG ATC CGG ACG AGC
     lys ala glu pro gly thr glu glu ile arg thr ser 505  GAT GAG GTC GGA GAC CGA GAC CAC CGG AGG CCA CAG
     asp glu val gly asp arg asp his arg arg pro gln
```

FIG. 14A

```
541  GAA AAG AAG AAG GCC AAG GGT CTG GGA AAG GAG ATC
     glu lys lys lys ala lys gly leu gly lys glu ile 577  ACG CTG CTG ATG CAG ACA CTG AAC ACG CTG AGC ACC
     thr leu leu met gln thr leu asn thr leu ser thr 613  CCA GAG GAG AAG CTG GCG GCT CTG TGC AAG AAG TAT
     pro glu glu lys leu ala ala leu cys lys lys tyr 649  GCG GAA CTG CTC GAG GAG CAC CGG AAC TCG CAG AAG
     ala glu leu leu glu glu his arg asn ser gln lys 685  CAG ATG AAG CTG CTG CAG AAG AAG CAG AGC CAG CTG
     gln met lys leu leu gln lys lys gln ser gln leu 721  GTG CAG GAG AAG GAC CAC CTG CGT GGC GAG CAC AGC
     val gln glu lys asp his leu arg gly glu his ser 757  AAG GCC ATC CTG GCC CGC AGC AAG CTC GAG AGC CTG
     lys ala ile leu ala arg ser lys leu glu ser leu 793  TGC CGG GAG CTG CAG CGG CAC AAC CGC TCG CTC AAG
     cys arg glu leu gln arg his asn arg ser leu lys 829  GAA GAA GGT GTG CAG CGA GCC CGA GAG GAG GAG GAG
     glu glu gly val gln arg ala arg glu glu glu glu 865  AAG CGC AAG GAG GTG ACG TCA CAC TTC CAG ATG ACG
     lys arg lys glu val thr ser his phe gln met thr 901  CTC AAC GAC ATT CAG CTG CAG ATG GAG CAG CAC AAC
     leu asn asp ile gln leu gln met glu gln his asn 937  GAG CGC AAC TCC AAG CTG CGC CAG GAG AAC ATG GAG
     glu arg asn ser lys leu arg gln glu asn met glu 973  CTG GCC GAG CGG CTC AAG AAG CTG ATT GAG CAG TAC
     leu ala glu arg leu lys lys leu ile glu gln tyr 1009 GAG CTG CGA GAA GAG CAC ATC GAC AAA GTC TTC AAA
     glu leu arg glu glu his ile asp lys val phe lys
```

FIG. 14B

```
1045  CAC AAG GAT CTG CAG CAG CAG CTG GTG GAC GCC AAG
      his lys asp leu gln gln gln leu val asp ala lys 1081  CTC CAG CAG GCC CAG GAG ATG CTG AAG GAG GCA GAG
      leu gln gln ala gln glu met leu lys glu ala glu 1117  GAG CGG CAC CAG CGG GAG AAG GAC TTT CTC CTG AAG
      glu arg his gln arg glu lys asp phe leu leu lys 1153  GAG GCC GTG GAG TCC CAG AGG ATG TGC GAG CTG ATG
      glu ala val glu ser gln arg met cys glu leu met 1189  AAG CAA CAG GAG ACC CAC CTG AAG CAG CAG CTT GCC
      lys gln gln glu thr his leu lys gln gln leu ala 1225  CTA TAC ACA GAG AAG TTT GAG GAG TTC CAG AAC ACT
      leu tyr thr glu lys phe glu glu phe gln asn thr 1261  CTT TCC AAA AGC AGC GAG GTG TTC ACC ACA TTC AAA
      leu ser lys ser ser glu val phe thr thr phe lys 1297  CAG GAA ATG GAA AAG ATG ACA AAG AAG ATC AAG AAG
      gln glu met glu lys met thr lys lys ile lys lys 1333  CTG GAG AAA GAG ACC ACC ATG TAC CGT TCC CGG TGG
      leu glu lys glu thr thr met tyr arg ser arg trp 1369  GAG AGC AGC AAC AAG GCC CTG CTT GAG ATG GCT GAG
      glu ser ser asn lys ala leu leu glu met ala glu 1405  GAG AAA ACA CTC CGG GAC AAA GAG CTG GAA GGC CTG
      glu lys thr leu arg asp lys glu leu glu gly leu 1441  CAG GTG AAA ATC CAG CGG CTG GAG AAG CTG TGC CGG
      gln val lys ile gln arg leu glu lys leu cys arg 1477  GCA CTG CAG ACA GAG CGC AAT GAC CTG AAC AAG AGG
      ala leu gln thr glu arg asn asp leu asn lys arg 1513  GTG CAG GAC CTG AGT GCC GGT GGC CAG GGC CCC GTC
      val gln asp leu ser ala gly gly gln gly pro val
```

FIG. 14C

```
1549  TCC GAC AGC GGT CCT GAG CGG AGG CCA GAG CCC GCC
      ser asp ser gly pro glu arg arg pro glu pro ala 1585  ACC ACC TCC AAG GAG CAG GGT GTC GAG GGC CCC GGG
      thr thr ser lys glu gln gly val glu gly pro gly 1621  GCT CAA GTA CCC AAC TCT CCA AGG GCC ACA GAC GCT
      ala gln val pro asn ser pro arg ala thr asp ala 1657  TCC TGC TGC GCA GGT GCA CCC AGC ACA GAG GCA TCA
      ser cys cys ala gly ala pro ser thr glu ala ser 1693  GGC CAG ACA GGG CCC CAG GAG CCC ACC ACT GCC ACT
      gly gln thr gly pro gln glu pro thr thr ala thr 1729  GCC TAG AGA GCT TGG TGC TGG GGT GTG CCA GGA AGG
      ala 1765  GAG CAG GCA GCC CAG CCA GGC CTG GCC CAG CCC AGG
1801  CTC CCA TGC TAA GCA GTC CGG TGC TGA GGC CAG GAT
1837  GTT CTG ACC TGG CTG GCA CCT GAC CCT CTG CAG TCT
1873  TGG ATT TTG TGG GTC AGT TTT ACA TGC ATA TGG CAC
1909  ACA TGC AAG GCC TCA CAC ATT TGT GTC TCT AAG TGT
1945  ACT GTG GGC TTG CAT CGG GGG TGA CGA TGG ACA GAT
1981  GAA GCC AGC GGC TCC CTT GTG AGC TGA AGT CTT ACG
2017  GAG GAG ACG GCG TCT GCA CTG CCA TCG CAG TGA CCT
2053  GCA GGA CGA GTT CCT TGA GCT TTC CCT GCC TGC TTT
2089  GAG GCT GAG ACC CCT CCC GGC CCT TCA GAG CTC CTG
2125  ACA GGT GAT ACA CAC CCA GCC TTG ACC GCA CTT CTC
2161  TTG GGT AGC TGG GCT CTC CTA GCC TCC CCC AGA GGC
2197  GCC ATT GCT TCT CTT GAC TTG GAG AGG GGA TGC CCA
2233  GGC GTG GCC TTG GCA GGC ACT GGG AGC TAG TGA TTG
2269  GGC TGC TCT CCT GCC TCG AGC AGG GGC AGG AGT GTT
2305  TCT GGT GGG ATG ATG CGC TCG CTG GTC AGG AGC CCC
2341  GTG GGC GCT GCT TCC CCC GCC CTC TGG TGA TGC CAG
2377  GAC CAG GCC AGT GAT GCT TCT CAG TAG CCT TAC CAT
2413  TCA CAG GTG CCT CTC CAG CCC GCA CAG TGA GTG ACA
2449  AGA TCA TCC AAA GGA TTC TTC TGA AGG TGT TCG TT
2485  TCG TTT TGT TTT GTT GCA CGT GAC GGT TTG TAT TGA
2521  GGA CCC TCT GAG GAA GAG GGG TGC TGT AGC AGT GGT
2557  CCC TGC GTG CCT GGC TCC AGT GTC CTG CCC TCC CCC
2593  CCC TCG CCA TGG CTC CTC GGC CGC TTT GGT GCT GAG
2629  GTT TCT GTT TGG TGA GAT CAG GTT GTC TGT TCA GAG
```

FIG. 14D

```
2665  AGA AGA GGC GTC TGA TGG CTT TGC CGC CAG CTT GCC
2701  TGC GGG CCT CAA TCC CGG GAG GCC GCC CGG TTC CCG
2737  TCA CTG TTG TCC CCG TGC AGT GCG TTG CTG GTC CCC
2773  AGG ACC AGC TGC TCG TTT GCT GTA TGG GTC AGT TTC
2809  TGC TTC CTG CCC CCC ACT CCA CCT AAC TGC AAT CCT
2845  TGG GGT TTC CCT GGT TCT CGT CCC TGG TAC CTC TGT
2881  GCC CAA GAA GTA GCC TTC TTT GGG ATT CTT GTT CTG
2917  CCC ATG CGG GAG CTG CTG CTG TCT GAC AGG TGA GGC
2953  CTG AGA CTC AGC GGC TGA CAG AGC TGC AGA GCT CTG
2989  CAC GGT GGC TCC CGG GGC GGC CTC TGT GTG CTG CAC
3025  ACC GCT GCT CTG CTG GCA CTG GCC AGT CTG TGC AGA
3061  GCA TTT GAG TAC TGG CTC AGG AGG GAG GGC TCT GCT
3097  GGC CTC GAG GGA CAG CGC CAC GTC TCC AGC TGG GCT
3133  CAG GGA GAG CCC CAG ACT GGC TGC GTA GGG TGC TTG
3169  GGG TTT GCT TCT TGC AGT ATT TCT TGG AAG CTG TTT
3205  TGT TGT CCT GCT ATT CCT TCA TCT TCC ACA GTC CAC
3241  GCT CAG CCT TTA ACT TGG ATC CCT CAC ATA ACA GGG
3277  TTC ATG AGA CCC GCA AGT ACG CCC AAG CTA CGT ATG
3313  GCT GAG GCC AGC TGG CAG GTG AAT GGC ACG CCA TTG
3349  CTG CTG CTA ATC CCT GGC ATA TCT TTA GTT CAC CTC
3385  GAA ATG CCC CCG CCA CAG TGC AAG CAG TGA GTC CAC
3421  GTG CCA CCC TGG GCT GAA TCC CAC CCC CTG TGA GTG
3457  TTG CCC GAG ATT GTG TCT CTT CTG AAT GCC TTC ACT
3493  GGG AAT GGC CTC TGC CGC CTC CTG CTC AGG GAG GCT
3529  TTC CCC TTC CCT CAG CCC CTG TGC CAG ACT GAG GTA
3565  CAA GAA CCG CCA AGC CCA TGC AAG GTG TGG CTA GGC
3601  GCC AGG GTG CAG GAA GGA GGC AGG TAG CTG CCT GCA
3637  CCC TTG AAA GCC AAG AGG CCT ACG GTG GCC TCC ATC
3673  CTG GCT TGC CTC ACT TCA GCT ACC TCG CAT AGC CCA
3709  GGG GTG GGG CTA TTG GAT TCC AGG GTG GGG GA TGG
3745  GAA GCT GCA GGG GGC AGG TGG CTC TCA CTA GGC TTC
3781  CCA GCT CAG GAA TGT GGG CCT CAG GTA GGG GAG AGC
3817  CTT TGC TCC ACT CCA CCC ATT GCA GGC ATC TA GGC
3853  CAG TCT AGA TGG CGA CCC CTT CTC TTC CTC TCC ATT
3889  GAC CAA ATC GTA CCT GTC TCT CCA GCT GCT CGC TTG
3925  CTC TGC TTT CCA AAG TCA GCC CAG GTA CCC AGG TGC
3961  CGC CCA CAT TGG CCT GGA ACC TGG ACC AGA GGC AAG
3997  GGA GGT GGC CTA TCC TTG AGT GAT AGC CAG TGC CTT
4033  CCT CAC CCG GTG GCT TCC ATG CCT GTG ACC TCA GAT
4069  TTA GGA CCA AGA GCT GTG TTG GTT TCT TAC GTT GTG
4105  AGC TTT CCC TCC AGG GGA CCA CAG CAG GTG AGG CTC
4141  GGA GCC CAG AGC CCT TGG CGC CGC CAG CAG TAA CTT
4177  GTG TCC GGA CCT TGT CCA GCT GAG CGC TTC GTG TAT
```

FIG. 14E

```
4213  GAC TCA GCT TCG TGT GTG AGT CCA GCG GAG TGC GTC
4249  ACG TGA CCT AGA CTC AGC GGT GTC AGC CGC ACT TTG
4285  ATT TGT TTG TTT TCC ATG AGG TTT TTG GAC CAT GGG
4321  CTT AGC TCA GGC AAC TTT TCT GTA AGG AGA ATG TTA
4357  ACT TTC TGT AAA GAT GCT TAT TTA ACT AAC GCC TGC
4393  TTC CCC CAC TCC CAA CCA GGT GGC CAC CGA GAG CTC
4429  ACC AGG AGG CCA ATA GAG CTG CTC CAG CTC TCC CAT
4465  CTT GCA CCG CAC AAA GGT GGC CGC CCC AGG GAC AGC
4501  CAG GCA CCT GCC TGG GGG AGG GGC TTC TCT TCC TTA
4537  TGG CCT GGC CAT CTA GAT TGT TTA AAG TTG TGC TGA
4573  CAG CTT TTT TTG GTT TTT TGG TTT TTG TTT TTG TTT
4609  TTG TTT TTG TTT TTG TCT ACT TTT GGT ATT CAC AAC
4645  AGC CAG GGA CTT GAT TTT GAT GTA TTT TAA GCC ACA
4681  TTA AAT AAA GAG TCT GTT GCC TTA AAA AAA AAA AAA
4717  AAA AAA
```

FIG. 14F

```
  1  GAC GCC TCA GAG CGG AAC AGG GAA GTG AAT CAG GCG
 37  CCG GGT AGT GGG TTG CTG GGC TGG GCT TGC TGA GGT
 73  AGA GGC AGC GCC AAG AAG AGG CCT TTG CCG CTG GTC
109  GGG ATT GGG ATG TCG AAG AAC ACA GTG TCG TCG GCC
                     met ser lys asn thr val ser ser ala 145  CGC TTC CGG AAG GTG GAC GTG GAT GAA TAT GAC GAG
     arg phe arg lys val asp val asp glu tyr asp glu 181  AAC AAG TTC GTG GAC GAA GAA GAT GGG GGC GAC GGC
     asn lys phe val asp glu glu asp gly gly asp gly 217  CAG GCC GGG CCC GAC GAG GGC GAG GTG GAC TCC TGC
     gln ala gly pro asp glu gly glu val asp ser cys 253  CTG CGG CAA GGA AAC ATG ACA GCT GCC CTA CAG GCA
     leu arg gln gly asn met thr ala ala leu gln ala 289  GCT CTG AAG AAC CCC CCT ATC AAC ACC AAG AGT CAG
     ala leu lys asn pro pro ile asn thr lys ser gln 325  GCA GTG AAG GAC CGG GCA GGC AGC ATT GTC TTG AAG
     ala val lys asp arg ala gly ser ile val leu lys 361  GTG CTC ATC TCT TTT AAA GCT AAT GAT ATA GAA AAG
     val leu ile ser phe lys ala asn asp ile glu lys 397  GCA GTT CAA TCT CTG GAC AAG AAT GGT GTG GAT CTC
     ala val gln ser leu asp lys asn gly val asp leu 433  CTA ATG AAG TAT ATT TAT AAA GGA TTT GAG AGC CCG
     leu met lys tyr ile tyr lys gly phe glu ser pro 469  TCT GAC AAT AGC AGT GCT ATG TTA CTG CAA TGG CAT
     ser asp asn ser ser ala met leu leu gln trp his 505  GAA AAG GCA CTT GCT GCT GGA GGA GTA GGG TCC ATT
     glu lys ala leu ala ala gly gly val gly ser ile 541  GTT CGT GTC TTG ACT GCA AGA AAA ACT GTG TAG TCT
     val arg val leu thr ala arg lys thr val
```

FIG. 15A

```
577   GGC AGG AAG TGG ATT ATC TGC CTC GGG AGT GGG AAT
613   TGC TGG TAC AAA GAC CAA AAC AAC CAA ATG CCA CCG
649   CTG CCC TGT GGG TAG CAT CTG TTT CTC TCA GCT TTG
685   CCT TCT TGC TTT TTC ATA TCT GTA AAG AAA AAA ATT
721   ACA TAT CAG TTG TCC CTT TAA TGA AAA TTG GGA TAA
757   TAT AGA AGA AAT TGT GTT AAA ATA GAA GTG TTT CAT
793   CCT TTC AAA ACC ATT TCA GTG ATG TTT ATA CCA ATC
829   TGT ATA TAG TAT AAT TTA CAT TCA AGT TTT AAT TGT
865   GCA ACT TTT AAC CCT GTT GGC TGG TTT TTG GTT CTG
901   TTT GGT TTT GTA TTA TTT TTA ACT AAT ACT GAA AAA
937   TTT GGT CAG AAT TTG AGG CCA GTT TCC TAG CTC ATT
973   GCT AGT CAG GAA ATG ATA TTT ATA AAA AAT ATG AGA
1009  GAC TGG CAG CTA TTA ACA TTG CAA AAC TGG ACC ATA
1045  TTT CCC TTA TTT AAT AAG CAA AAT ATG TTT TTG GAA
1081  TAA GTG GTG GGT GAA TAC CAC TGC TAA GTT ATA GCT
1117  TTG TTT TTG CTT GCC TCC TCA TTA TCT GTA CTG TGG
1153  GTT TAA GTA TGC TAC TTT CTC TCA GCA TCC AAT AAT
1189  CAT GGC CCC TCA ATT TAT TTG TGG TCA CGC AGG GTT
1225  CAG AGC AAG AAG TCT TGC TTT ATA CAA ATG TAT CCA
1261  TAA AAT ATC AGA GCT TGT TGG GCA TGA ACA TCA AAC
1297  TTT TGT TCC ACT AAT ATG GCT CTG TTT GGA AAA AAC
1333  TGC AAA TCA GAA AGA ATG ATT TGC AGA AAG AAA GAA
1369  AAA CTA TGG TGT AAT TTA AAC TCT GGG CAG CCT CTG
1405  AAT GAA ATG CTA CTT TCT TTA GAA ATA TAA TAG CTG
1441  CCT TAG ACA TTA TGA GGT ATA CAA CTA GTA TTT AAG
1477  ATA CCA TTT AAT ATG CCC CGT AAA TGT CTT CAG TGT
1513  TCT TCA GGG TAG TTG GGA TCT CAA AAG ATT TGG TTC
1549  AGA TCC AAA CAA ATA CAC ATT CTG TGT TTT AGC TCA
1585  GTG TTT TCT AAA AAA AGA AAC TGC CAC ACA GCA AAA
1621  AAT TGT TTA CTT TGT TGG ACA AAC CAA ATC AGT TCT
1657  CAA AAA ATG ACC GGT GCT TAT AAA AAG TTA TAA ATA
1693  TCG AGT AGC TCT AAA ACA AAC CAC CTG ACC AAG AGG
1729  GAA GTG AGC TTG TGC TTA GTA TTT ACA TTG GAT GCC
1765  AGT TTT GTA ATC ACT GAC TTA TGT GCA AAC TGG TGC
1801  AGA AAT TCT ATA AAC TCT TTG CTG TTT TTG ATA CCT
1837  GCT TTT TGT TTC ATT TTG TTT TGT TTT GTA AAA ATG
1873  ATA AAA CTT CAG AAA ATA AAA TGT CAG TGT TGA ATA
1909  ATT AAA AAA AAA AAA AA
```

FIG. 15B

```
  1  GAA GAG CGA GTA CTT GAG AAA GAA GAG GAA GAA GAT
     glu glu arg val leu glu lys glu glu glu glu asp 37  GAT GAT GAA GAT GAA GAT GAA GAA GAT GAT GTG TCA
     asp asp glu asp glu asp glu glu asp asp val ser 73  GAG GGC TCT GAA GTG CCC GAG AGT GAC CGT CCT GCA
     glu gly ser glu val pro glu ser asp arg pro ala 109  GGT GCC CAG CAC CAC CAG CTT AAC GGC GAG CGG GGA
     gly ala gln his his gln leu asn gly glu arg gly 145  CCT CAG AGT GCC AAG GAG AGG GTC AAG GAG TGG ACC
     pro gln ser ala lys glu arg val lys glu trp thr 181  CCC TGC GGA CCG CAC CAG GGC CAG GAT GAA GGG CGG
     pro cys gly pro his gln gly gln asp glu gly arg 217  GGG CCA GCC CCG GGC AGC GGC ACC CGC CAG GTG TTC
     gly pro ala pro gly ser gly thr arg gln val phe 253  TCC ATG GCA GCC ATG AAC AAG GAA GGG GGA ACA GCT
     ser met ala ala met asn lys glu gly gly thr ala 289  TCT GTT GCC ACC GGG CCA GAC TCC CCG TCC CCC GTG
     ser val ala thr gly pro asp ser pro ser pro val 325  CCT TTG CCC CCA GGC AAA CCA GCC CTA CCT GGG GCC
     pro leu pro pro gly lys pro ala leu pro gly ala 361  GAC GGG ACC CCC TTT GGC TGT CCT CCC GGG CGC AAA
     asp gly thr pro phe gly cys pro pro gly arg lys 397  GAG AAG CCA TCT GAT CCC GTC GAG TGG ACC GTG ATG
     glu lys pro ser asp pro val glu trp thr val met 433  GAT GTC GTC GAA TAT TTT ACT GAG GCT GGA TTC CCG
     asp val val glu tyr phe thr glu ala gly phe pro 469  GAG CAG GCG ACA GCT TTC CAA GAG CAG GAA ATT GAT
     glu gln ala thr ala phe gln glu gln glu ile asp
```

FIG. 16A

```
505  GGC AAA TCT TTG CTG CTC ATG CAG CGC ACA GAT GTG
     gly lys ser leu leu leu met gln arg thr asp val 541  CTC ACC GGC CTG TCC ATC CGC CTC GGG CCA GCC CTG
     leu thr gly leu ser ile arg leu gly pro ala leu 577  AAA ATC TAC GAG CAC CAC ATC AAG GTG CTT CAG CAA
     lys ile tyr glu his his ile lys val leu gln gln 613  GGC CAC TTT GAG GAT GAT GAC CCC GAT GGC TTC TTA
     gly his phe glu asp asp asp pro asp gly phe leu 649  GGC TGA GCG CCC AGC CTC ACC CCT GCC CCA GCC CAT
     gly 685  TCC GGC CCC CAT CTC ACC CAA GAT CCC CCA GAG TCC
721  AGG AGC TGG ACG GGG ACA CCC TCA GCC CTC ATA ACA
757  GAT TCC AAG GAG AGG GCA CCC TCT TGT CCT TAT CTT
793  TGC CCC TTG TNT CTG TCT CAC ACA CAT CTG CTC CTC
829  AGC ACG TCG GTG TGG GGA GGG GAT TGC TCC TTA AAC
865  CCC AGG TGG CTG ACC CTC CCC ACC CAG TCC AGG ACA
901  TTT TAG GAA AAA AAA AAT GAA ATG TGG GGG GCT TCT
937  CAT CTC CCC AAG ATC CTC TTC CGT TCA GCC AGA TGT
973  TTC CTG TAT AAA TGT TTG GAT CTG CCT GTT TAT TTT
1009 GGT GGG TGG TCT TTC CTC CCT CCC CTA CCA CCC ATG
1045 CCC CCC TTC TCA GTC TGC CCC TGG CCT CCA GCC CCT
1081 AGG GGA CTA GCT GGG TTG GGG TTC CTC GGG CCT TTT
1117 CTC TCC TCC CTC TTT TCT TTC TGT TGA TTG TCG CTC
1153 CAG CTG GCT GTA TTG CTT TTT AAT ATT GCA CCG AAG
1189 GTT TTT TAA ATA AAA TTT TA
```

FIG. 16B

```
  1   CA AAA AGC AGC CCA GGA CAA CCG GAA GCA GGA CCC GAG GGA GCC
         lys ser ser pro gly gln pro glu ala gly pro glu gly ala 45   CAG GAG CGG CCC AGC CAG GCG GCT CCT GCA GTA GAA GCA GAA GGT
      gln glu arg pro ser gln ala ala pro ala val glu ala glu gly 90   CCC GGC AGC AGC CAG GCT CCT CGG AAG CCG GAG GGG GCT CAA GCC
      pro gly ser ser gln ala pro arg lys pro glu gly ala gln ala 135   AGA ACG GCT CAG TCT GGG GCC CTT CGT GAT GTC TCT GAG GAG CTG
      arg thr ala gln ser gly ala leu arg asp val ser glu glu leu 180   AGC CGC CAA CTG GAA GAC ATA CTG AGC ACA TAC TGT GTG GAC AAT
      ser arg gln leu glu asp ile leu ser thr tyr cys val asp asn 225   AAC CAG GGG GGC CCC GGC GAG GAT GGG GCA CAG GGT GAG CCG GCT
      asn gln gly gly pro gly glu asp gly ala gln gly glu pro ala 270   GAA CCC GAA GAT GCA GAG AAG TCC CGG ACC TAT GTG GCA AGG AAT
      glu pro glu asp ala glu lys ser arg thr tyr val ala arg asn 315   GGG GAG CCT GAA CCA ACT CCA GTA GTC TAT GGA GAG AAG GAA CCC
      gly glu pro glu pro thr pro val val tyr gly glu lys glu pro 360   TCC AAG GGG GAT CCA AAC ACA GAA GAG ATC CGG CAG AGT GAC GAG
      ser lys gly asp pro asn thr glu glu ile arg gln ser asp glu 405   GTC GGA GAC CGA GAC CAT CGA AGG CCA CAG GAG AAG AAA AAA GCC
      val gly asp arg asp his arg arg pro gln glu lys lys lys ala 450   AAG GGT TTG GGG AAG GAG ATC ACG TTG CTG ATG CAG ACA TTG AAT
      lys gly leu gly lys glu ile thr leu leu met gln thr leu asn 495   ACT CTG AGT ACC CCA GAG GAG AAG CTG GCT GCT CTG TGC AAG AAG
      thr leu ser thr pro glu glu lys leu ala ala leu cys lys lys 540   TAT GCT GAA CTG CTG GAG GAG CAC CGG AAT TCA CAG AAG CAG ATG
      tyr ala glu leu leu glu glu his arg asn ser gln lys gln met 585   AAG CTC CTA CAG AAA AAG CAG AGC CAG CTG GTG CAA GAG AAG GAC
      lys leu leu gln lys lys gln ser gln leu val gln glu lys asp 630   CAC CTG CGC GGT GAG CAC AGC AAG GCC GTC CTG GCC CGC AGC AAG
      his leu arg gly glu his ser lys ala val leu ala arg ser lys 675   CTT GAG AGC CTA TGC CGT GAG CTG CAG CGG CAC AAC CGC TCC CTC
      leu glu ser leu cys arg glu leu gln arg his asn arg ser leu
```

FIG. 17A

```
720   AAG GAA GAA GGT GTG CAG CGG GCC CGG GAG GAG GAG GAG AAG CGC
      lys glu glu gly val gln arg ala arg glu glu glu glu lys arg 765   AAG GAG GTG ACC TCG CAC TTC CAG GTG ACA CTG AAT GAC ATT CAG
      lys glu val thr ser his phe gln val thr leu asn asp ile gln 810   CTG CAG ATG GAA CAG CAC AAT GAG CGC AAC TCC AAG CTG CGC CAA
      leu gln met glu gln his asn glu arg asn ser lys leu arg gln 855   GAG AAC ATG GAG CTG GCT GAG AGG CTC AAG AAG CTG ATT GAG CAG
      glu asn met glu leu ala glu arg leu lys lys leu ile glu gln 900   TAT GAG CTG CGC GAG GAG CAT ATC GAC AAA GTC TTC AAA CAC AAG
      tyr glu leu arg glu glu his ile asp lys val phe lys his lys 945   GAC CTA CAA CAG CAG CTG GTG GAT GCC AAG CTC CAG CAG GCC CAG
      asp leu gln gln gln leu val asp ala lys leu gln gln ala gln 990   GAG ATG CTA AAG GAG GCA GAA GAG CGG CAC CAG CGG GAG AAG GAT
      glu met leu lys glu ala glu glu arg his gln arg glu lys asp 1035  TTT CTC CTG AAA GAG GCA GTA GAG TCC CAG AGG ATG TGT GAG CTG
      phe leu leu lys glu ala val glu ser gln arg met cys glu leu 1080  ATG AAG CAG CAA GAG ACC CAC CTG AAG CAA CAG CTT GCC CTA TAC
      met lys gln gln glu thr his leu lys gln gln leu ala leu tyr 1125  ACA GAG AAG TTT GAG GAG TTC CAG AAC ACA CTT TCC AAA AGC AGC
      thr glu lys phe glu glu phe gln asn thr leu ser lys ser ser 1170  GAG GTA TTC ACC ACA TTC AAG CAG GAG ATG GAA AAG ATG ACT AAG
      glu val phe thr thr phe lys gln glu met glu lys met thr lys 1215  AAG ATC AAG AAG CTG GAG AAA GAA ACC ACC ATG TAC CGG TCC CGG
      lys ile lys lys leu glu lys glu thr thr met tyr arg ser arg 1260  TGG GAG AGC AGC AAC AAG GCC CTG CTT GAG ATG GCT GAG GAG AAA
      trp glu ser ser asn lys ala leu leu glu met ala glu glu lys 1305  ACA GTC CGG GAT AAA GAA CTG GAG GGC CTG CAG GTA AAA ATC CAA
      thr val arg asp lys glu leu glu gly leu gln val lys ile gln 1350  CGG CTG GAG AAG CTG TGC CGG GCA CTG CAG ACA GAG CGC AAT GAC
      arg leu glu lys leu cys arg ala leu gln thr glu arg asn asp 1395  CTG AAC AAG AGG GTA CAG GAC CTG AGT GCT GGT GGC CAG GGC TCC
      leu asn lys arg val gln asp leu ser ala gly gly gln gly ser 1440  CTC ACT GAC AGT GGC CCT GAG AGG AGG CCA GAG GGG CCT GGG GCT
      leu thr asp ser gly pro glu arg arg pro glu gly pro gly ala
```

FIG. 17B

```
1485  CAA GCA CCC AGC TCC CCC AGG GTC ACA GAA GCG CCT TGC TAC CCA
      gln ala pro ser ser pro arg val thr glu ala pro cys tyr pro 1530  GGA GCA CCG AGC ACA GAA GCA TCA GGC CAG ACT GGG CCT CAA GAG
      gly ala pro ser thr glu ala ser gly gln thr gly pro gln glu 1575  CCC ACC TCC GCC AGG GCC TAG AGA GCC TGG TGT TGG GTC ATG CTG
      pro thr ser ala arg ala ***

1620  GGA AGG GAG CGG CAG CCC AGC CAG GCC TGG CCC ATA AAA GGC TCC
1665  CAT GCT GAG CAG CCC ATT GCT GAA GCC AGG ATG TTC TTG ACC TGG
1710  CTG GCA TCT GGC ACT TGC AAT TTT GGA TTT TGT GGG TCA GTT TTA
1755  CGT ACA TAG GGC ATT TTG CAA GGC CTT GCA AAT GCA TTT ATA CCT
1800  GTA AGT GTA CAG TGG GCT TGC ATT GGG GAT GGG GGT GTG TAC AGA
1845  TGA AGT CAG TGG CTT GTC TGT GAG CTG AAG AGT CTT GAG AGG GGC
1890  TGT CAT CTG TAG CTG CCA TCA CAG TGA GTT GGC AGA AGT GAC TTG
1935  AGC ATT TCT CTG TCT GAT TTG AGG CTC AGA CCC CTC CCT GCC CTT
1980  TCA GAG CTC AAA ACA AGT AAT ACA CCA AGG TCT TGA CTG CAT TTG
2025  TCT TGT GAG CAG GGC TTG CTT GGT CAG CTC AGG CCC TCC TAG CTG
2070  CTT GGA GGC TCC TTT GAT TCT CTA GAC CTG GAA AAG GTG TCC CTA
2115  GGC AGA GCC CTG GCA GGG CGC TCA GAG CTG GGA TTT CCT GCC TGG
2160  AAC AAG GGA CCT GGA GAA TGT TTT TGC GTG GGA TGA TGT GCT GGT
2205  CAG GAG CCC CTT GGG CAT CGC TTC CCC TGC CCT TTG GTA GTG CCA
2250  GGA CCA GGC CAA TGA TGC TTC TCA GTA GCC TTA TCA TTC ACA GGT
2295  GCC TCT CTA GCC TGC ACA AAT GAT TGA CAA GAG ATC ACC CAA AGG
2340  ATT ATT TCT GAA GGT GTT TTT TTC TTT ATT TCT TTT TCT TTT TTT
2385  TTT TTT CTT TTT CTT TTT TTT TTG CAC ATG ACA GTG TTT GTA TTG
2430  AGG ACC TTC CAA GGA AAA GGG ATG CTG TAC CAG TGG TGC CTG GGT
2475  GCC TGG CCT CCA GTG TCC CAC CTC CTT CAC CAC CCC ACT TGG CTC
2520  CTT TGC CAT CTT GAT GCT GAG GTT TCC TGT TTG GTG AGA TCA GGT
2565  TGT TTG TGG TAA AAG AAA GGA AAG GGC TTC TGA TGG CTT TGC CAC
2610  AAG CTT ACC TGT GGG TTT CAG TCC TGA GAG GCC ACC ACC AGT TCC
2655  CAT CAG CAC TGT CTC CAT GCA GCA GTT GCT GGG TCC CAT GTC CAG
2700  CTG CCT CTT TGG CTT CAT GGG TTT TTC TGC TTC CTG CCC CCA CCC
2745  CCA CAT GTG CAA TCC TCA AGA TTT GTC CTG ATT CTA TTT CCT GGC
2790  ACC TCC CTG CCT GTC CTT GGG GAT TCT ACT TCT TCC TGT GTG GGG
2835  CCC ATA GCT GTT GTC TAA CAG GTA AGA AAT GAA ATT GAA CTA TTG
2880  ACT GGG CCC CAG AAA TCC ATA AAA TGG CTG CAG ACA GTT GTT TCT
2925  GTG TCC TGT TCT ACC CCC ACT CCA GTA CAT AAC TAC TAT GTA CTG
2970  TGT AGA GCC ATT CTA TAT GCT GAA TGT TCT GCT GTT GCA AAC TTG
3015  CCA GGG TAT TAG CCA GTG TTT GTG CCA AGC AGT TTT CGG GGA CAA
3060  CAG AAT GAC TCA GAC CAA GAT GGA TAG GAT GGT TAG GGC TTT GCT
3105  TCT TGC TGT TTT TCT TTG AAC TAG TCA TTG TCC TGC AGG TCC CTT
3150  CAT CTT CCA TAC CTA GCC CAC TCT TTT AGC CCT TAC CTT AAA TCT
3195  CTC AGA TAA GTT GGT TCA CAA AGA ATG TTA AGT ACT GAA TCA TGT
3240  GTG ACT GAG ACC AGA GAT GGC AAA TGA ATG CAC ACA TTC TCC
3285  TTC TCC TGC CCC AGG GCA GGT ACC ACT GAT CTG CAT CAG AGT TGC
3330  CTG CTA TTC TCT GGT GTA CCT TCA TCT AGG TGC CCT CAA GCA
3375  GCT GTG TGA GTG TTG AGA TCT CTG CCA TCT CTG GCT GAG ATA CTG
3420  CTG TCC TGT GAA GTG TTT CCC ATG ACC TTT TTC TTC CCC TTT GAA
3465  TCC CTC TTG TCT GGA GTA GTC CTT GCC TTC TTC TTG CTC CAG TAG
```

FIG. 17C

```
3510  GCC TTT TCC TTA CCC CAG CCC TTG TGC CAG GCT AAG CTG GTA CAA
3555  GAG CTG CCA ACT CAC AGA GTT TTG CTA GGC GAG AGA GGT GCA GGG
3600  AAG AGG CAG AGG TAT GCA CCT TCC CCC TTG AAG AGA GGG GAA AGG
3645  CCT ACA GTG GCC CAC ATA ATT GCC TGA CTC ACA CTT CAG CTA CCT
3690  CTT AAT GCC TGT GGA GGG ACT GGA GCT GCT GGA TCC CAG TGT GGT
3735  GGT GTA GGA GGC CAC AGT GAG CAG GTG GCC CCA GCT GGG TTT CCC
3780  AGG TCA GGA ATG TGG GCC CCA GGC AAG GTG CAG CCT TTG CTC ACA
3825  GCT CCA TCC ATG TCT AGA CCT TCA GGC CAG TCT GCA GAT GAG GTT
3870  CCC TAC CTT TTT CTT CTC TTC ATT GAC CAA ATC AAC CAA TCA CTA
3915  CAG CTG CTC TGC TTC TGC TTT CCA AAG TAG CCC AGG TCC TGG GCC
3960  AGA TGC AGG GGA GGT GCC TAT CCA TGA GTG AAG GCC AGT GTC TTC
4005  CTC ACC TGG GTG GTC CCA CAC TTG TGA CCC TCA GTT TTA GGA CCC
4050  AAG ATC TGT GTT GGT TTC TTA GAT GCT AGC TTT CTC AGG GGG
4095  ACC ACA GCA GGT GAA GCT CAA GAG CGC ATG GCT CTG CTA ATA GTA
4140  AAT TGT TTT CAG GGC CTT GTC CAG CTG AGA GCT TCA TGT CCA CCA
4185  GAT TCT GAG AGG TGT CAG CAG CAC TTT TTT TTT TTA TTT GTT GTT
4230  TGT TTT CCA TGA GGT TAT CGG ACC ATG GGC TGA GCT CAG GCA CTT
4275  TCT GTA GGA GAC TGT TAT TTC TGT AAA GAT GGT TAT TTA ACC CTC
4320  CTC CAC CCC ATC ACG GTG GCC CTG AGG GCT GAC CCG GAG GCC AGT
4365  GGA GCT GCC TGG TGT CCA CGG GGG AGG GCC AAG GCC TGC TGA GCT
4410  GAT TCT CCA GCT GCT GCC CCA GCC TTT CCG CCT TGC ACA GCA CAG
4455  AGG TGG TCA CCC CAG GGA CAG CCA GGC ACC TGC TCC TCT TGC CCT
4500  TCC TGG GGG AAA GGA GCT GCC TTC TGT CCC TGT AAC TGC TTT CCT
4545  TAT GGC CCA ACC CGG CCA CTC AGA CTT GTT TGA AGC TGC ACT GGC
4590  AGC TTT TTT GTC TCC TTT GGG TAT TCA CAA CAG CCA GGG ACT TGA
4635  TTT TGA TGT ATT TTA AAC CAC ATT AAA TAA AGA GTC TGT TGC CTT
4680  AAA AAA AAA AAA AAA AAA
```

FIG. 17D

```
GTG GAC GTG GAT GAG TAC GAC GAG AAC AAG TTC GTG
val asp val asp glu tyr asp glu asn lys phe val GAC GAG GAA GAC GGC GGC GAC GGC
asp glu glu asp gly gly asp gly
```

FIG. 18

```
        1                                                            50
Rabbit  MSKNTVSSAR FRKVDVDEYD ENKFVDEEDG GDGQAGPDEG EVDSCLRQGN
Human   .......... .......... .......... .......... ..........

51                                                           100
Rabbit  MTAALQAALK NPPINTRSQA VKDRAGSIVL KVLISFKAGD IEKAVQSLDR
Human   .......... ......K... .......... .........N. .........K 101                                                          150
Rabbit  NGVDLLMKYI YKGFESPSDN SSAVLLQWHE KALAAGGVGS IVRVLTARKT
Human   .......... .......... ...M...... .......... ..........

151
Rabbit  V
Human   .
```

FIG. 19

```
        1                                                            50
Rabbit  EERVLEKEEE EEEEEDDEDD DDDVVSEGSE VPESDRPAGA QHHQLNGGER
Human   .......... .DDD..EDEE ..-....... .......... ........-...

51                                                           100
Rabbit  GPQTAKERAK EWSLCGPHPG QEEGRGPAAG SGTRQVFSMA ALSKEGGSAS
Human   ...S....V. ...TP....Q. .D......P. .......... .MN....T..

101                                                          150
Rabbit  STTGPDSPSP VPLPPGKPAL PGADGTPFGC PAGRKEKPAD PVEWTVMDVV
Human   VA........ .......... .......... .P......S. ..........

151                                                          200
Rabbit  EYFTEAGFPE QATAFQEQEI DGKSLLLMQR TDVLTGLSIR LGPALKIYEH
Human   .......... .......... .......... .......... ..........

201         220
Rabbit  HIKVLQQGHF EDDDPEGFLG
Human   .......... .....D....
```

FIG. 20

```
            1                                                          50
Rabbit  MKNQDKKNGA AKQPNPKSSP GQPEAGAEGA QGRPGRPAPA REAEG-ASSQ
Human   ---------- ----------  ......P...  .E..SQA...  V....PG...

51                                                        100
Rabbit  APGRPEGAQA KTAQPGALCD VSEELSRQLE DILSTYCVDN NQGAPGEDGV
Human   ..RK......  R...S...R.  ..........  ..........  ...G.....A 101                                                       150
Rabbit  QGEPPEPEDA EKSRAYVARN GEPEPGTPVV NGEKETSKAE PGTEEIRTSD
Human   ....A.....  ....T.....  .....-....  Y....P..GD  .N.....Q..

151                                                       200
Rabbit  EVGDRDHRRP QEKKKAKGLG KEITLLMQTL NTLSTPEEKL AALCKKYAEL
Human   ..........  ..........  ..........  ..........  ..........

201                                                       250
Rabbit  LEEHRNSQKQ MKLLQKKQSQ LVQEKDHLRG EHSKAILARS KLESLCRELQ
Human   ..........  ..........  ..........  .....V....  ..........

251                                                       300
Rabbit  RHNRSLKEEG VQRAREEEEK RKEVTSHFQM TLNDIQLQME QHNERNSKLR
Human   ..........  ..........  ........V.  ..........  ..........

301                                                       350
Rabbit  QENMELAERL KKLIEQYELR EEHIDKVFKH KDLQQQLVDA KLQQAQEMLK
Human   ..........  ..........  ..........  ..........  ..........

351                                                       400
Rabbit  EAEERHQREK DFLLKEAVES QRMCELMKQQ ETHLKQQLAL YTEKFEEFQN
Human   ..........  ..........  ..........  ..........  ..........

401                                                       450
Rabbit  TLSKSSEVFT TFKQEMEKMT KKIKKLEKET TMYRSRWESS NKALLEMAEE
Human   ..........  ..........  ..........  ..........  ..........

451                                                       500
Rabbit  KTLRDKELEG LQVKIQRLEK LCRALQTERN DLNKRVQDLS AGGQGPVSDS
Human   ..V.......  ..........  ..........  ..........  .....SLT..

501                                                       550
Rabbit  GPERRPEPAT TSKEQGVEGP GAQVPNSPRA TDASCCAGAP STEASGQTGP
Human   .........-  -------...  ...A.S...V  .E.P.YP...  ..........

551
Rabbit  QEPTTATA
Human   ....S.R.
```

FIG. 21

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 151 amino acids
      (B) TYPE: amino acid
      (D) TOPOLOGY: linear (ii) MOLECULE TYPE: protein (xi) SEQUENCE DESCRIPTION: SEQ ID NO: 1:

```
Met Ser Lys Asn Thr Val Ser Ser Ala Arg Phe Arg Lys Val Asp Val
 1               5                  10                  15

Asp Glu Tyr Asp Glu Asn Lys Phe Val Asp Glu Asp Gly Gly Asp
                20                  25                  30

Gly Gln Ala Gly Pro Asp Glu Gly Val Asp Ser Cys Leu Arg Gln
            35                  40                  45

Gly Asn Met Thr Ala Ala Leu Gln Ala Leu Lys Asn Pro Pro Ile
        50                  55                  60

Asn Thr Arg Ser Gln Ala Val Lys Asp Arg Ala Gly Ser Ile Val Leu
 65                  70                  75                  80

Lys Val Leu Ile Ser Phe Lys Ala Gly Asp Ile Glu Lys Ala Val Gln
                    85                  90                  95

Ser Leu Asp Arg Asn Gly Val Asp Leu Leu Met Lys Tyr Ile Tyr Lys
                100                 105                 110

Gly Phe Glu Ser Pro Ser Asp Asn Ser Ser Ala Val Leu Leu Gln Trp
            115                 120                 125

His Glu Lys Ala Leu Ala Ala Gly Gly Val Gly Ser Ile Val Arg Val
        130                 135                 140

Leu Thr Ala Arg Lys Thr Val
145                 150
```

(2) INFORMATION FOR SEQ ID NO: 2:

(i) SEQUENCE CHARACTERISTICS:
      (A) LENGTH: 317 amino acids
      (B) TYPE: amino acid
      (D) TOPOLOGY: linear (ii) MOLECULE TYPE: protein (xi) SEQUENCE DESCRIPTION: SEQ ID NO: 2:

```
Asp Cys Arg Ser Ser Ser Asn Asn Arg Xaa Pro Lys Gly Gly Ala Ala
 1               5                  10                  15

Arg Ala Gly Gly Pro Ala Arg Pro Val Ser Leu Arg Glu Val Val Arg
                20                  25                  30

Tyr Leu Gly Gly Ser Ser Gly Ala Gly Gly Arg Leu Thr Arg Gly Arg
            35                  40                  45

Val Gln Gly Leu Leu Glu Glu Glu Ala Ala Ala Arg Gly Arg Leu Glu
        50                  55                  60

Arg Thr Arg Leu Gly Ala Leu Ala Leu Pro Arg Gly Asp Arg Pro Gly
 65                  70                  75                  80

Arg Ala Pro Pro Ala Ala Ser Ala Arg Ala Ala Arg Asn Lys Arg Ala
                    85                  90                  95
```

-continued

```
Gly Glu Glu Arg Val Leu Glu Lys Glu Glu Glu Glu Glu Glu
            100                 105                 110
Asp Asp Glu Asp Asp Asp Asp Val Val Ser Glu Gly Ser Glu Val
            115                 120                 125
Pro Glu Ser Asp Arg Pro Ala Gly Ala Gln His His Gln Leu Asn Gly
            130                 135                 140
Gly Glu Arg Gly Pro Gln Thr Ala Lys Glu Arg Ala Lys Glu Trp Ser
145                 150                 155                 160
Leu Cys Gly Pro His Pro Gly Gln Glu Glu Gly Arg Gly Pro Ala Ala
                    165                 170                 175
Gly Ser Gly Thr Arg Gln Val Phe Ser Met Ala Ala Leu Ser Lys Glu
            180                 185                 190
Gly Gly Ser Ala Ser Ser Thr Thr Gly Pro Asp Ser Pro Ser Pro Val
            195                 200                 205
Pro Leu Pro Pro Gly Lys Pro Ala Leu Pro Gly Ala Asp Gly Thr Pro
            210                 215                 220
Phe Gly Cys Pro Ala Gly Arg Lys Glu Lys Pro Ala Asp Pro Val Glu
225                 230                 235                 240
Trp Thr Val Met Asp Val Val Glu Tyr Phe Thr Glu Ala Gly Phe Pro
                    245                 250                 255
Glu Gln Ala Thr Ala Phe Gln Glu Gln Glu Ile Asp Gly Lys Ser Leu
            260                 265                 270
Leu Leu Met Gln Arg Thr Asp Val Leu Thr Gly Leu Ser Ile Arg Leu
            275                 280                 285
Gly Pro Ala Leu Lys Ile Tyr Glu His His Ile Lys Val Leu Gln Gln
            290                 295                 300
Gly His Phe Glu Asp Asp Pro Glu Gly Phe Leu Gly
305                 310                 315
```

(2) INFORMATION FOR SEQ ID NO: 3:

(i) SEQUENCE CHARACTERISTICS:
        (A) LENGTH: 232 amino acids
        (B) TYPE: amino acid
        (D) TOPOLOGY: linear (ii) MOLECULE TYPE: protein (xi) SEQUENCE DESCRIPTION: SEQ ID NO: 3:

```
Ala Ser Ala Arg Ala Ala Arg Asn Lys Arg Ala Gly Glu Glu Arg Val
1                   5                   10                  15
Leu Glu Lys Glu Glu Glu Glu Glu Glu Glu Asp Asp Glu Asp Asp
            20                  25                  30
Asp Asp Asp Val Val Ser Glu Gly Ser Glu Val Pro Glu Ser Asp Arg
            35                  40                  45
Pro Ala Gly Ala Gln His His Gln Leu Asn Gly Gly Glu Arg Gly Pro
            50                  55                  60
Gln Thr Ala Lys Glu Arg Ala Lys Glu Trp Ser Leu Cys Gly Pro His
65                  70                  75                  80
Pro Gly Gln Glu Glu Gly Arg Gly Pro Ala Ala Gly Ser Gly Thr Arg
                    85                  90                  95
Gln Val Phe Ser Met Ala Ala Leu Ser Lys Gly Gly Ser Ala Ser
            100                 105                 110
Ser Thr Thr Gly Pro Asp Ser Pro Ser Pro Val Pro Leu Pro Pro Gly
            115                 120                 125
Lys Pro Ala Leu Pro Gly Ala Asp Gly Thr Pro Phe Gly Cys Pro Ala
```

```
              130                 135                 140
Gly Arg Lys Glu Lys Pro Ala Asp Pro Val Glu Trp Thr Val Met Asp
145                 150                 155                 160

Val Val Glu Tyr Phe Thr Glu Ala Gly Phe Pro Glu Gln Ala Thr Ala
                165                 170                 175

Phe Gln Glu Gln Glu Ile Asp Gly Lys Ser Leu Leu Met Gln Arg
            180                 185                 190

Thr Asp Val Leu Thr Gly Leu Ser Ile Arg Leu Gly Pro Ala Leu Lys
                195                 200                 205

Ile Tyr Glu His His Ile Lys Val Leu Gln Gln Gly His Phe Glu Asp
210                 215                 220

Asp Asp Pro Glu Gly Phe Leu Gly
225                 230

(2) INFORMATION FOR SEQ ID NO: 4:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO: 4:

Thr Arg Leu Gly Ala Leu Ala Leu Pro Arg Gly Asp Arg Pro Gly Arg
1               5                   10                  15

Ala Pro Pro Ala Ala Ser Ala Arg Ala Arg Asn Lys Arg Ala Gly
                20                  25                  30

Glu Glu Arg Val Leu Glu Lys Glu Glu Glu Glu Glu Glu Asp
         35                  40                  45

Asp Glu Asp Asp Asp Asp Val Val Ser Glu Gly Ser Glu Val Pro
    50                  55                  60

Glu Ser Asp Arg Pro Ala Gly Ala Gln His His Gln Leu Asn Gly Gly
65                  70                  75                  80

Glu Arg Gly Pro Gln Thr Ala Lys Glu Arg Ala Lys Glu Trp Ser Leu
                85                  90                  95

Cys Gly Pro His Pro Gly Gln Glu Glu Gly Arg Gly Pro Ala Ala Gly
                100                 105                 110

Ser Gly Thr Arg Gln Val Phe Ser Met Ala Ala Leu Ser Lys Glu Gly
                115                 120                 125

Gly Ser Ala Ser Ser Thr Thr Gly Pro Asp Ser Pro Ser Pro Val Pro
130                 135                 140

Leu Pro Pro Gly Lys Pro Ala Leu Pro Gly Ala Asp Gly Thr Pro Phe
145                 150                 155                 160

Gly Cys Pro Ala Gly Arg Lys Glu Lys Pro Ala Asp Pro Val Glu Trp
                165                 170                 175

Thr Val Met Asp Val Val Glu Tyr Phe Thr Glu Ala Gly Phe Pro Glu
            180                 185                 190

Gln Ala Thr Ala Phe Gln Glu Gln Glu Ile Asp Gly Lys Ser Leu Leu
        195                 200                 205

Leu Met Gln Arg Thr Asp Val Leu Thr Gly Leu Ser Ile Arg Leu Gly
210                 215                 220

Pro Ala Leu Lys Ile Tyr Glu His His Ile Lys Val Leu Gln Gln Gly
225                 230                 235                 240

His Phe Glu Asp Asp Asp Pro Glu Gly Phe Leu Gly
                245                 250
```

(2) INFORMATION FOR SEQ ID NO: 5:

(i) SEQUENCE CHARACTERISTICS:
        (A) LENGTH: 557 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 5:

```
Met Lys Asn Gln Asp Lys Lys Asn Gly Ala Ala Lys Gln Pro Asn Pro
 1               5                  10                  15

Lys Ser Ser Pro Gly Gln Pro Glu Ala Gly Ala Glu Gly Ala Gln Gly
            20                  25                  30

Arg Pro Gly Arg Pro Ala Pro Ala Arg Glu Ala Glu Gly Ala Ser Ser
        35                  40                  45

Gln Ala Pro Gly Arg Pro Glu Gly Ala Gln Ala Lys Thr Ala Gln Pro
    50                  55                  60

Gly Ala Leu Cys Asp Val Ser Glu Glu Leu Ser Arg Gln Leu Glu Asp
65                  70                  75                  80

Ile Leu Ser Thr Tyr Cys Val Asp Asn Gln Gly Ala Pro Gly Glu
                85                  90                  95

Asp Gly Val Gln Gly Glu Pro Pro Glu Pro Glu Asp Ala Glu Lys Ser
                100                 105                 110

Arg Ala Tyr Val Ala Arg Asn Gly Glu Pro Glu Pro Gly Thr Pro Val
            115                 120                 125

Val Asn Gly Glu Lys Glu Thr Ser Lys Ala Glu Pro Gly Thr Glu Glu
    130                 135                 140

Ile Arg Thr Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Ile Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Met Thr Leu Asn Asp Ile Gln Leu Gln Met
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
```

```
                    340                 345                 350
Glu Arg His Gln Arg Glu Lys Asp Phe Leu Leu Lys Glu Ala Val Glu
            355                 360                 365

Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
            420                 425                 430

Arg Ser Arg Trp Glu Ser Ser Asn Lys Ala Leu Leu Glu Met Ala Glu
    435                 440                 445

Glu Lys Thr Leu Arg Asp Lys Glu Leu Glu Gly Leu Gln Val Lys Ile
450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gln Gly Pro Val
                485                 490                 495

Ser Asp Ser Gly Pro Glu Arg Arg Pro Glu Pro Ala Thr Thr Ser Lys
            500                 505                 510

Glu Gln Gly Val Glu Gly Pro Gly Ala Gln Val Pro Asn Ser Pro Arg
    515                 520                 525

Ala Thr Asp Ala Ser Cys Cys Ala Gly Ala Pro Ser Thr Glu Ala Ser
    530                 535                 540

Gly Gln Thr Gly Pro Gln Glu Pro Thr Thr Ala Thr Ala
545                 550                 555

(2) INFORMATION FOR SEQ ID NO: 6:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO: 6:

Met Ser Lys Asn Thr Val Ser Ser Ala Arg Phe Arg Lys Val Asp Val
 1               5                  10                  15

Asp Glu Tyr Asp Glu Asn Lys Phe Val Asp Glu Glu Asp Gly Gly Asp
                20                  25                  30

Gly Gln Ala Gly Pro Asp Glu Gly Glu Val Asp Ser Cys Leu Arg Gln
            35                  40                  45

Gly Asn Met Thr Ala Ala Leu Gln Ala Ala Leu Lys Asn Pro Pro Ile
    50                  55                  60

Asn Thr Lys Ser Gln Ala Val Lys Asp Arg Ala Gly Ser Ile Val Leu
65                  70                  75                  80

Lys Val Leu Ile Ser Phe Lys Ala Asn Asp Ile Glu Lys Ala Val Gln
                85                  90                  95

Ser Leu Asp Lys Asn Gly Val Asp Leu Leu Met Lys Tyr Ile Tyr Lys
            100                 105                 110

Gly Phe Glu Ser Pro Ser Asp Asn Ser Ser Ala Met Leu Leu Gln Trp
    115                 120                 125

His Glu Lys Ala Leu Ala Ala Gly Gly Val Gly Ser Ile Val Arg Val
130                 135                 140
```

```
Leu Thr Ala Arg Lys Thr Val
145                 150

(2) INFORMATION FOR SEQ ID NO: 7:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO: 7:

Glu Glu Arg Val Leu Glu Lys Glu Glu Glu Asp Asp Glu Asp
 1               5                  10                  15

Glu Asp Glu Glu Asp Asp Val Ser Glu Gly Ser Glu Val Pro Glu Ser
                20                  25                  30

Asp Arg Pro Ala Gly Ala Gln His His Gln Leu Asn Gly Glu Arg Gly
            35                  40                  45

Pro Gln Ser Ala Lys Glu Arg Val Lys Glu Trp Thr Pro Cys Gly Pro
        50                  55                  60

His Gln Gly Gln Asp Glu Gly Arg Gly Pro Ala Pro Gly Ser Gly Thr
 65                 70                  75                  80

Arg Gln Val Phe Ser Met Ala Ala Met Asn Lys Glu Gly Gly Thr Ala
                85                  90                  95

Ser Val Ala Thr Gly Pro Asp Ser Pro Ser Pro Val Pro Leu Pro Pro
            100                 105                 110

Gly Lys Pro Ala Leu Pro Gly Ala Asp Gly Thr Pro Phe Gly Cys Pro
        115                 120                 125

Pro Gly Arg Lys Glu Lys Pro Ser Asp Pro Val Glu Trp Thr Val Met
        130                 135                 140

Asp Val Val Glu Tyr Phe Thr Glu Ala Gly Phe Pro Glu Gln Ala Thr
145                 150                 155                 160

Ala Phe Gln Glu Gln Glu Ile Asp Gly Lys Ser Leu Leu Leu Met Gln
                165                 170                 175

Arg Thr Asp Val Leu Thr Gly Leu Ser Ile Arg Leu Gly Pro Ala Leu
            180                 185                 190

Lys Ile Tyr Glu His His Ile Lys Val Leu Gln Gln Gly His Phe Glu
        195                 200                 205

Asp Asp Asp Pro Asp Gly Phe Leu Gly
        210                 215

(2) INFORMATION FOR SEQ ID NO: 8:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO: 8:

Lys Ser Ser Pro Gly Gln Pro Glu Ala Gly Pro Glu Gly Ala Gln Glu
 1               5                  10                  15

Arg Pro Ser Gln Ala Ala Pro Ala Val Glu Ala Glu Gly Pro Gly Ser
                20                  25                  30

Ser Gln Ala Pro Arg Lys Pro Glu Gly Ala Gln Ala Arg Thr Ala Gln
            35                  40                  45
```

-continued

```
Ser Gly Ala Leu Arg Asp Val Ser Glu Glu Leu Ser Arg Gln Leu Glu
 50                  55                  60

Asp Ile Leu Ser Thr Tyr Cys Val Asp Asn Asn Gln Gly Gly Pro Gly
 65                  70                  75                  80

Glu Asp Gly Ala Gln Gly Glu Pro Ala Glu Pro Glu Asp Ala Glu Lys
                 85                  90                  95

Ser Arg Thr Tyr Val Ala Arg Asn Gly Glu Pro Glu Pro Thr Pro Val
            100                 105                 110

Val Tyr Gly Glu Lys Glu Pro Ser Lys Gly Asp Pro Asn Thr Glu Glu
        115                 120                 125

Ile Arg Gln Ser Asp Glu Val Gly Asp Arg Asp His Arg Arg Pro Gln
130                 135                 140

Glu Lys Lys Lys Ala Lys Gly Leu Gly Lys Glu Ile Thr Leu Leu Met
145                 150                 155                 160

Gln Thr Leu Asn Thr Leu Ser Thr Pro Glu Glu Lys Leu Ala Ala Leu
                165                 170                 175

Cys Lys Lys Tyr Ala Glu Leu Leu Glu Glu His Arg Asn Ser Gln Lys
            180                 185                 190

Gln Met Lys Leu Leu Gln Lys Lys Gln Ser Gln Leu Val Gln Glu Lys
        195                 200                 205

Asp His Leu Arg Gly Glu His Ser Lys Ala Val Leu Ala Arg Ser Lys
210                 215                 220

Leu Glu Ser Leu Cys Arg Glu Leu Gln Arg His Asn Arg Ser Leu Lys
225                 230                 235                 240

Glu Glu Gly Val Gln Arg Ala Arg Glu Glu Glu Lys Arg Lys Glu
                245                 250                 255

Val Thr Ser His Phe Gln Val Thr Leu Asn Asp Ile Gln Leu Gln Met
                260                 265                 270

Glu Gln His Asn Glu Arg Asn Ser Lys Leu Arg Gln Glu Asn Met Glu
            275                 280                 285

Leu Ala Glu Arg Leu Lys Lys Leu Ile Glu Gln Tyr Glu Leu Arg Glu
        290                 295                 300

Glu His Ile Asp Lys Val Phe Lys His Lys Asp Leu Gln Gln Gln Leu
305                 310                 315                 320

Val Asp Ala Lys Leu Gln Gln Ala Gln Glu Met Leu Lys Glu Ala Glu
                325                 330                 335

Glu Arg His Gln Arg Glu Lys Asp Phe Leu Leu Lys Glu Ala Val Glu
            340                 345                 350

Ser Gln Arg Met Cys Glu Leu Met Lys Gln Gln Glu Thr His Leu Lys
        355                 360                 365

Gln Gln Leu Ala Leu Tyr Thr Glu Lys Phe Glu Glu Phe Gln Asn Thr
370                 375                 380

Leu Ser Lys Ser Ser Glu Val Phe Thr Thr Phe Lys Gln Glu Met Glu
385                 390                 395                 400

Lys Met Thr Lys Lys Ile Lys Lys Leu Glu Lys Glu Thr Thr Met Tyr
                405                 410                 415

Arg Ser Arg Trp Glu Ser Ser Asn Lys Ala Leu Leu Glu Met Ala Glu
            420                 425                 430

Glu Lys Thr Val Arg Asp Lys Glu Leu Glu Gly Leu Gln Val Lys Ile
        435                 440                 445

Gln Arg Leu Glu Lys Leu Cys Arg Ala Leu Gln Thr Glu Arg Asn Asp
450                 455                 460

Leu Asn Lys Arg Val Gln Asp Leu Ser Ala Gly Gly Gln Gly Ser Leu
```

```
                465               470               475               480
         Thr Asp Ser Gly Pro Glu Arg Arg Pro Glu Gly Pro Gly Ala Gln Ala
                             485               490               495

Pro Ser Ser Pro Arg Val Thr Glu Ala Pro Cys Tyr Pro Gly Ala Pro
                         500               505               510

Ser Thr Glu Ala Ser Gly Gln Thr Gly Pro Gln Glu Pro Thr Ser Ala
                     515               520               525

Arg Ala
             530

(2) INFORMATION FOR SEQ ID NO: 9:

(i) SEQUENCE CHARACTERISTICS:
        (A) LENGTH: 20 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 9:

Val Asp Val Asp Glu Tyr Asp Glu Asn Lys Phe Val Asp Glu Glu Asp
 1               5                  10                  15

Gly Gly Asp Gly
            20

(2) INFORMATION FOR SEQ ID NO: 10:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 58...510

(xi) SEQUENCE DESCRIPTION: SEQ ID NO: 10:

AAGCCTCGCA GCGGTCGGGG CGGCGCCGCG GAGGCTCGAG GGCGGCGGGC GGCGGCG ATG         60
                                                                 Met
                                                                  1

TCG AAG AAC ACG GTG TCG TCG GCG CGG TTC CGG AAG GTG GAC GTG GAT          108
Ser Lys Asn Thr Val Ser Ser Ala Arg Phe Arg Lys Val Asp Val Asp
         5                  10                  15

GAG TAC GAC GAG AAC AAG TTC GTG GAC GAG GAA GAC GGC GGC GAC GGC          156
Glu Tyr Asp Glu Asn Lys Phe Val Asp Glu Glu Asp Gly Gly Asp Gly
             20                  25                  30

CAG GCG GGG CCG GAC GAG GGC GAG GTG GAC TCG TGC CTG CGG CAA GGG          204
Gln Ala Gly Pro Asp Glu Gly Glu Val Asp Ser Cys Leu Arg Gln Gly
         35                  40                  45

AAC ATG ACA GCC GCC CTG CAG GCG GCG CTG AAG AAC CCT CCC ATC AAC          252
Asn Met Thr Ala Ala Leu Gln Ala Ala Leu Lys Asn Pro Pro Ile Asn
 50                  55                  60                  65

ACC AGG AGC CAG GCG GTG AAG GAC CGG GCA GGC AGC ATC GTG CTG AAG          300
Thr Arg Ser Gln Ala Val Lys Asp Arg Ala Gly Ser Ile Val Leu Lys
                 70                  75                  80

GTG CTC ATC TCC TTC AAG GCC GGC GAC ATA GAA AAG GCC GTG CAG TCC          348
Val Leu Ile Ser Phe Lys Ala Gly Asp Ile Glu Lys Ala Val Gln Ser
                 85                  90                  95

CTG GAC AGG AAC GGC GTG GAC CTG CTC ATG AAG TAC ATC TAC AAG GGC          396
Leu Asp Arg Asn Gly Val Asp Leu Leu Met Lys Tyr Ile Tyr Lys Gly
```

```
                100                 105                 110
TTC GAG AGC CCC TCC GAC AAC AGC AGC GCC GTG CTC CTG CAG TGG CAC        444
Phe Glu Ser Pro Ser Asp Asn Ser Ser Ala Val Leu Leu Gln Trp His
    115                 120                 125

GAG AAG GCG CTG GCT GCA GGA GGA GTG GGC TCC ATC GTC CGT GTC CTG        492
Glu Lys Ala Leu Ala Ala Gly Gly Val Gly Ser Ile Val Arg Val Leu
130                 135                 140                 145

ACT GCA AGG AAA ACC GTG TAGCCTGGCA GGAACGGGTG CCTGCCGGGG AGCGGGAG      548
Thr Ala Arg Lys Thr Val
                150

CTGCCGGTAC AAAGACCAAA ACGCCCAGAT GCCGCCGCTG CCCTGTGGGC GGCGTCTGTT      608

CCCAGCTTCG CTTTTTCCCT TTCCCGTGTC TGTCAGGATT ACATAAGGTT TCCCTTCGTG      668

AGAATCGGAG TGGCGCAGAG GGTCCTGTTC ATACGCGCCG TGCGTCCGGC TGTGTAAGAC      728

CCCTGCCTTC AGTGTCCTTG AGCAACGGTA GCGTGTCGCC GGCTGGGTTT GGTTTTGTCG      788

TGGAGGGATC TGGTCAGAAT TTGAGGCCAG TTTCCTAACT CATTGCTGGT CAGGAAATGA      848

TCTTCATTTA AAAAAAAAAA AAAGACTGGC AGCTATTATG CAAAACTGGA CCCTCTTCCC      908

TTATTTAAGC AGAGTGAGTT TCTGGAACCA GTGGTGCCCC CCCCCCGCC CCGGCCGCCG       968

TCCTGCTCAA GGGAAGCCTC CCTGCAGAGC AGCAGAGCCC CTGGGCAGGA GCGCCGCGTC     1028

CCGCTCCCAG GAGACAGCAT GCGCGGTCAC GCGGCACTTC CTGTGCCTCC CAGCCCCAGT     1088

GCCCCGGAGT TCTTCAGGGC GACAGGGACC TCAGAAGACT GGATCCGATC AGACAGACG      1148

CCCATTCTTG GTTCAGCTCA GTGTTTTCAA AAGGAACGTG CTACCGTGGG TAGAGCACAC     1208

TGGTTCTCAG AACACGGCCG GCGCTTGACG GTTGTCACAG CTCCAGAACA AATCCTGGGA     1268

GACAGGCGAG CGCGAGTCGC CGGGCAGGAA TTCCACACAC TCGTGCTGTT TTTGATACCT     1328

GCTTTTTGTT TTGTTTTGTA AAAATGATGC ACTTGAGAAA ATAAAACGTC AGTGTTGACA     1388

AAAAAAAAAA AAAAA                                                      1404

(2) INFORMATION FOR SEQ ID NO: 11:

(i) SEQUENCE CHARACTERISTICS:
        (A) LENGTH: 1617 base pairs
        (B) TYPE: nucleic acid
        (C) STRANDEDNESS: single
        (D) TOPOLOGY: linear (xi) SEQUENCE DESCRIPTION: SEQ ID NO: 11:

GACTGCCGCA GCAGCAGCAA CAACCGCTAG CCGAAGGGTG GCGCGGCGCG GGCCGGCGGC        60

CCGGCGCGGC CCGTGAGCCT GCGGGAAGTC GTGCGCTACC TCGGGGGTAG CAGCGGCGCT       120

GGCGGCCGCC TGACCCGCGG CCGCGTGCAG GGTCTGCTGG AAGAGGAGGC GGCGGCGCGG       180

GGCCGCCTGG AGCGCACCCG TCTCGGAGCG CTTGCGCTGC CCCGCGGGGA CAGGCCCGGA       240

CGGGCGCCAC CGGCCGCCAG CGCCCGCGCG GCGCGGAACA AGAGAGCTGG CGAGGAGCGA       300

GTGCTTGAAA AGGAGGAGGA GGAGGAGGAG GAGGAAGACG ACGAGGACGA CGACGACGAC       360

GTCGTGTCCG AGGGCTCGGA GGTGCCCGAG AGCGATCGTC CCGCGGGTGC GCAGCATCAC       420

CAGCTGAATG GCGGCGAGCG CGGCCCGCAG ACCGCCAAGG AGCGGGCCAA GGAGTGGTCG       480

CTGTGTGGCC CCCACCCTGG CCAGGAGGAA GGGCGGGGGC CGGCCGCGGG CAGTGGCACC       540

CGCCAGGTGT TCTCCATGGC GGCCTTGAGT AAGGAGGGGG GATCAGCCTC TTCGACCACC       600

GGGCCTGACT CCCCGTCCCC GGTGCCTTTG CCCCCCGGGA AGCCAGCCCT CCAGGAGCC        660

GATGGGACCC CCTTTGGCTG CCCTGCCGGG CGCAAAGAGA AGCCGGCAGA CCCCGTGGAG       720
```

-continued

```
TGGACAGTCA TGGACGTCGT GGAGTACTTC ACCGAGGCGG GCTTCCCTGA GCAAGCCACG      780

GCTTTCCAGG AGCAGGAGAT CGACGGCAAG TCCCTGCTGC TCATGCAGCG CACCGATGTC      840

CTCACCGGCC TGTCCATCCG CCTGGGGCCA GCGTTGAAAA TCTATGAGCA CCATATCAAG      900

GTGCTGCAGC AGGGTCACTT CGAGGACGAT GACCCGGAAG GCTTCCTGGG ATGAGCACAG      960

AGCCGCCGCG CCCCTTGTCC CCACCCCCAC CCCGCCTGGA CCCATTCCTG CCTCCATGTC     1020

ACCCAAGGTG TCCCAGAGGC CAGGAGCTGG ACTGGGCAGG CGAGGGTGC GGACCTACCC     1080

TGATTCTGGT AGGGGCGGG GCCTTGCTGT GCTCATTGCT ACCCCCCCAC CCCGTGTGTG     1140

TCTCTGCACC TGCCCCCAGC ACACCCCTCC CGGAGCCTGG ATGTCGCCTG GGACTCTGGC     1200

CTGCTCATTT TGCCCCCAGA TCAGCCCCCT CCCTCCCTCC TGTCCAGGA CATTTTTTAA     1260

AAGAAAAAAA GGAAAAAAAA AAATTGGGGA GGGGGCTGGG AAGGTGCCCC AAGATCCTCC     1320

TCGGCCCAAC CAGGTGTTTA TTCCTATATA TATATATATA TGTTTTGTTC TGCCTGTTTT     1380

TCGTTTTTTG GTGCGTGGCC TTTCTTCCCT CCCACCACCA CTCATGGCCC CAGCCCTGCT     1440

CGCCCTGTCG GCGGGAGCAG CTGGGAATGG GAGGAGGGTG GGACCTTGGG TCTGTCTCCC     1500

ACCCTCTCTC CCGTTGGTTC TGTTGTCGCT CCAGCTGGCT GTATTGCTTT TTAATATTGC     1560

ACCGAAGGGT TGTTTTTTTT TTTTAAATA AAATTTTAAA AAAAGGAAAA AAAAAAA        1617
```

(2) INFORMATION FOR SEQ ID NO: 12:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...696

(xi) SEQUENCE DESCRIPTION: SEQ ID NO: 12:

```
GCC AGC GCC CGC GCG GCG CGG AAC AAG AGA GCT GGC GAG GAG CGA GTG        48
Ala Ser Ala Arg Ala Ala Arg Asn Lys Arg Ala Gly Glu Glu Arg Val
 1               5                  10                  15

CTT GAA AAG GAG GAG GAG GAG GAG GAG GAA GAC GAC GAG GAC GAC            96
Leu Glu Lys Glu Glu Glu Glu Glu Glu Glu Asp Asp Glu Asp Asp
             20                  25                  30

GAC GAC GAC GTC GTG TCC GAG GGC TCG GAG GTG CCC GAG AGC GAT CGT       144
Asp Asp Asp Val Val Ser Glu Gly Ser Glu Val Pro Glu Ser Asp Arg
         35                  40                  45

CCC GCG GGT GCG CAG CAT CAC CAG CTG AAT GGC GGC GAG CGC GGC CCG       192
Pro Ala Gly Ala Gln His His Gln Leu Asn Gly Gly Glu Arg Gly Pro
 50                  55                  60

CAG ACC GCC AAG GAG CGG GCC AAG GAG TGG TCG CTG TGT GGC CCC CAC       240
Gln Thr Ala Lys Glu Arg Ala Lys Glu Trp Ser Leu Cys Gly Pro His
 65              70                  75                  80

CCT GGC CAG GAG GAA GGG CGG GGG CCG GCC GCG GGC AGT GGC ACC CGC       288
Pro Gly Gln Glu Glu Gly Arg Gly Pro Ala Ala Gly Ser Gly Thr Arg
             85                  90                  95

CAG GTG TTC TCC ATG GCG GCC TTG AGT AAG GAG GGG GGA TCA GCC TCT       336
Gln Val Phe Ser Met Ala Ala Leu Ser Lys Glu Gly Gly Ser Ala Ser
                100                 105                 110

TCG ACC ACC GGG CCT GAC TCC CCG TCC CCG GTG CCT TTG CCC CCC GGG       384
Ser Thr Thr Gly Pro Asp Ser Pro Ser Pro Val Pro Leu Pro Pro Gly
            115                 120                 125

AAG CCA GCC CTC CCA GGA GCC GAT GGG ACC CCC TTT GGC TGC CCT GCC       432
Lys Pro Ala Leu Pro Gly Ala Asp Gly Thr Pro Phe Gly Cys Pro Ala
```

```
           130                 135                 140
GGG CGC AAA GAG AAG CCG GCA GAC CCC GTG GAG TGG ACA GTC ATG GAC        480
Gly Arg Lys Glu Lys Pro Ala Asp Pro Val Glu Trp Thr Val Met Asp
145                 150                 155                 160

GTC GTG GAG TAC TTC ACC GAG GCG GGC TTC CCT GAG CAA GCC ACG GCT        528
Val Val Glu Tyr Phe Thr Glu Ala Gly Phe Pro Glu Gln Ala Thr Ala
                165                 170                 175

TTC CAG GAG CAG GAG ATC GAC GGC AAG TCC CTG CTG CTC ATG CAG CGC        576
Phe Gln Glu Gln Glu Ile Asp Gly Lys Ser Leu Leu Leu Met Gln Arg
            180                 185                 190

ACC GAT GTC CTC ACC GGC CTG TCC ATC CGC CTG GGG CCA GCG TTG AAA        624
Thr Asp Val Leu Thr Gly Leu Ser Ile Arg Leu Gly Pro Ala Leu Lys
        195                 200                 205

ATC TAT GAG CAC CAT ATC AAG GTG CTG CAG CAG GGT CAC TTC GAG GAC        672
Ile Tyr Glu His His Ile Lys Val Leu Gln Gln Gly His Phe Glu Asp
    210                 215                 220

GAT GAC CCG GAA GGC TTC CTG GGA TGAGCACAGA GCCGCCGCGC CCCTTGTCC        726
Asp Asp Pro Glu Gly Phe Leu Gly
225                 230

CACCCCCACC CCGCCTGGAC CCATTCCTGC CTCCATGTCA CCCAAGGTGT CCCAGAGGCC      786

AGGAGCTGGA CTGGGCAGGC GAGGGGTGCG GACCTACCCT GATTCTGGTA GGGGGCGGGG      846

CCTTGCTGTG CTCATTGCTA CCCCCCCACC CCGTGTGTGT CTCTGCACCT GCCCCCAGCA      906

CACCCCTCCC GGAGCCTGGA TGTCGCCTGG GACTCTGGCC TGCTCATTTT GCCCCCAGAT      966

CAGCCCCCTC CCTCCCTCCT GTCCCAGGAC ATTTTTTAAA AGAAAAAAAG GAAAAAAAAA     1026

AATTGGGGAG GGGGCTGGGA AGGTGCCCCA AGATCCTCCT CGGCCCAACC AGGTGTTTAT     1086

TCCTATATAT ATATATATAT GTTTTGTTCT GCCTGTTTTT CGTTTTTTGG TGCGTGGCCT     1146

TTCTTCCCTC CCACCACCAC TCATGGCCCC AGCCCTGCTC GCCCTGTCGG CGGGAGCAGC     1206

TGGGAATGGG AGGAGGGTGG GACCTTGGGT CTGTCTCCCA CCCTCTCTCC CGTTGGTTCT     1266

GTTGTCGCTC CAGCTGGCTG TATTGCTTTT TAATATTGCA CCGAAGGGTT GTTTTTTTTT     1326

TTTTAAATAA AATTTTAAAA AAAGGAAAAA AAAAA                                1362

(2) INFORMATION FOR SEQ ID NO: 13:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (ix) FEATURE:
         (A) NAME/KEY: Coding Sequence
         (B) LOCATION: 1...756

(xi) SEQUENCE DESCRIPTION: SEQ ID NO: 13:

ACC CGT CTC GGA GCG CTT GCG CTG CCC CGC GGG GAC AGG CCC GGA CGG        48
Thr Arg Leu Gly Ala Leu Ala Leu Pro Arg Gly Asp Arg Pro Gly Arg
1               5                   10                  15

GCG CCA CCG GCC GCC AGC GCC CGC GCG GCG CGG AAC AAG AGA GCT GGC        96
Ala Pro Pro Ala Ala Ser Ala Arg Ala Arg Asn Lys Arg Ala Gly
            20                  25                  30

GAG GAG CGA GTG CTT GAA AAG GAG GAG GAG GAG GAG GAG GAA GAC           144
Glu Glu Arg Val Leu Glu Lys Glu Glu Glu Glu Glu Glu Glu Asp
        35                  40                  45

GAC GAG GAC GAC GAC GAC GAC GTC GTG TCC GAG GGC TCG GAG GTG CCC       192
Asp Glu Asp Asp Asp Asp Asp Val Val Ser Glu Gly Ser Glu Val Pro
    50                  55                  60
```

```
GAG AGC GAT CGT CCC GCG GGT GCG CAG CAT CAC CAG CTG AAT GGC GGC      240
Glu Ser Asp Arg Pro Ala Gly Ala Gln His His Gln Leu Asn Gly Gly
 65                  70                  75                  80

GAG CGC GGC CCG CAG ACC GCC AAG GAG CGG GCC AAG GAG TGG TCG CTG      288
Glu Arg Gly Pro Gln Thr Ala Lys Glu Arg Ala Lys Glu Trp Ser Leu
                 85                  90                  95

TGT GGC CCC CAC CCT GGC CAG GAG GAA GGG CGG GGG CCG GCC GCG GGC      336
Cys Gly Pro His Pro Gly Gln Glu Glu Gly Arg Gly Pro Ala Ala Gly
            100                 105                 110

AGT GGC ACC CGC CAG GTG TTC TCC ATG GCG GCC TTG AGT AAG GAG GGG      384
Ser Gly Thr Arg Gln Val Phe Ser Met Ala Ala Leu Ser Lys Glu Gly
        115                 120                 125

GGA TCA GCC TCT TCG ACC ACC GGG CCT GAC TCC CCG TCC CCG GTG CCT      432
Gly Ser Ala Ser Ser Thr Thr Gly Pro Asp Ser Pro Ser Pro Val Pro
130                 135                 140

TTG CCC CCC GGG AAG CCA GCC CTC CCA GGA GCC GAT GGG ACC CCC TTT      480
Leu Pro Pro Gly Lys Pro Ala Leu Pro Gly Ala Asp Gly Thr Pro Phe
145                 150                 155                 160

GGC TGC CCT GCC GGG CGC AAA GAG AAG CCG GCA GAC CCC GTG GAG TGG      528
Gly Cys Pro Ala Gly Arg Lys Glu Lys Pro Ala Asp Pro Val Glu Trp
                165                 170                 175

ACA GTC ATG GAC GTC GTG GAG TAC TTC ACC GAG GCG GGC TTC CCT GAG      576
Thr Val Met Asp Val Val Glu Tyr Phe Thr Glu Ala Gly Phe Pro Glu
            180                 185                 190

CAA GCC ACG GCT TTC CAG GAG CAG GAG ATC GAC GGC AAG TCC CTG CTG      624
Gln Ala Thr Ala Phe Gln Glu Gln Glu Ile Asp Gly Lys Ser Leu Leu
        195                 200                 205

CTC ATG CAG CGC ACC GAT GTC CTC ACC GGC CTG TCC ATC CGC CTG GGG      672
Leu Met Gln Arg Thr Asp Val Leu Thr Gly Leu Ser Ile Arg Leu Gly
210                 215                 220

CCA GCG TTG AAA ATC TAT GAG CAC CAT ATC AAG GTG CTG CAG CAG GGT      720
Pro Ala Leu Lys Ile Tyr Glu His His Ile Lys Val Leu Gln Gln Gly
225                 230                 235                 240

CAC TTC GAG GAC GAT GAC CCG GAA GGC TTC CTG GGA TGAGCACAGA GCCG      772
His Phe Glu Asp Asp Asp Pro Glu Gly Phe Leu Gly
                245                 250

GCGCCCCTTG TCCCCACCCC CACCCCGCCT GGACCCATTC CTGCCTCCAT GTCACCCAAG    832

GTGTCCCAGA GGCCAGGAGC TGGACTGGGC AGGCGAGGGG TGCGGACCTA CCCTGATTCT    892

GGTAGGGGGC GGGGCCTTGC TGTGCTCATT GCTACCCCCC CACCCCGTGT GTGTCTCTGC    952

ACCTGCCCCC AGCACACCCC TCCCGGAGCC TGGATGTCGC CTGGGACTCT GGCCTGCTCA   1012

TTTTGCCCCC AGATCAGCCC CCTCCCTCCC TCCTGTCCCA GGACATTTTT TAAAAGAAAA   1072

AAAGGAAAAA AAAAAATTGG GGAGGGGGCT GGGAAGGTGC CCCAAGATCC TCCTCGGCCC   1132

AACCAGGTGT TTATTCCTAT ATATATATAT ATATGTTTTG TTCTGCCTGT TTTTCGTTTT   1192

TTGGTGCGTG GCCTTTCTTC CCTCCCACCA CCACTCATGG CCCCAGCCCT GCTCGCCCTG   1252

TCGGCGGGAG CAGCTGGGAA TGGGAGGAGG GTGGGACCTT GGGTCTGTCT CCCACCCTCT   1312

CTCCCGTTGG TTCTGTTGTC GCTCCAGCTG GCTGTATTGC TTTTTAATAT TGCACCGAAG   1372

GGTTGTTTTT TTTTTTTTAA ATAAAATTTT AAAAAAAGGA AAAAAAAAAA             1422
```

(2) INFORMATION FOR SEQ ID NO: 14:

(i) SEQUENCE CHARACTERISTICS:
        (A) LENGTH: 4722 base pairs
        (B) TYPE: nucleic acid
        (C) STRANDEDNESS: single
        (D) TOPOLOGY: linear (ix) FEATURE:
    (A) NAME/KEY: Coding Sequence
    (B) LOCATION: 61...1731

(xi) SEQUENCE DESCRIPTION: SEQ ID NO: 14:

```
GTGGAAAATA GCAACTGTGT TTCTCAAGGA TCCAATCCCA ACCTAAGGTG GCAGCGCACA        60

ATG AAG AAT CAA GAC AAA AAG AAC GGG GCT GCC AAA CAG CCC AAC CCC        108
Met Lys Asn Gln Asp Lys Lys Asn Gly Ala Ala Lys Gln Pro Asn Pro
 1               5                  10                  15

AAA AGC AGC CCG GGA CAG CCG GAA GCA GGA GCG GAG GGA GCC CAG GGG        156
Lys Ser Ser Pro Gly Gln Pro Glu Ala Gly Ala Glu Gly Ala Gln Gly
             20                  25                  30

CGG CCC GGC CGG CCG GCC CCC GCC CGA GAA GCC GAA GGT GCC AGC AGC        204
Arg Pro Gly Arg Pro Ala Pro Ala Arg Glu Ala Glu Gly Ala Ser Ser
         35                  40                  45

CAG GCT CCC GGG AGG CCG GAG GGG GCT CAA GCC AAA ACT GCT CAG CCT        252
Gln Ala Pro Gly Arg Pro Glu Gly Ala Gln Ala Lys Thr Ala Gln Pro
     50                  55                  60

GGG GCG CTC TGT GAT GTC TCT GAG GAG CTG AGC CGC CAG TTG GAA GAC        300
Gly Ala Leu Cys Asp Val Ser Glu Glu Leu Ser Arg Gln Leu Glu Asp
 65                  70                  75                  80

ATA CTC AGT ACA TAC TGT GTG GAC AAC AAC CAG GGG GCC CCG GGT GAG        348
Ile Leu Ser Thr Tyr Cys Val Asp Asn Asn Gln Gly Ala Pro Gly Glu
                 85                  90                  95

GAT GGG GTC CAG GGT GAG CCC CCT GAA CCT GAA GAT GCA GAG AAG TCT        396
Asp Gly Val Gln Gly Glu Pro Pro Glu Pro Glu Asp Ala Glu Lys Ser
            100                 105                 110

CGC GCC TAT GTG GCA AGG AAT GGG GAG CCG GAG CCG GGC ACC CCA GTA        444
Arg Ala Tyr Val Ala Arg Asn Gly Glu Pro Glu Pro Gly Thr Pro Val
        115                 120                 125

GTC AAT GGC GAG AAG GAG ACC TCC AAG GCA GAG CCG GGC ACG GAA GAG        492
Val Asn Gly Glu Lys Glu Thr Ser Lys Ala Glu Pro Gly Thr Glu Glu
    130                 135                 140

ATC CGG ACG AGC GAT GAG GTC GGA GAC CGA GAC CAC CGG AGG CCA CAG        540
Ile Arg Thr Ser Asp Glu Val Gly Asp Arg Asp His Arg Arg Pro Gln
145                 150                 155                 160

GAA AAG AAG AAG GCC AAG GGT CTG GGA AAG GAG ATC ACG CTG CTG ATG        588
Glu Lys Lys Lys Ala Lys Gly Leu Gly Lys Glu Ile Thr Leu Leu Met
                165                 170                 175

CAG ACA CTG AAC ACG CTG AGC ACC CCA GAG GAG AAG CTG GCG GCT CTG        636
Gln Thr Leu Asn Thr Leu Ser Thr Pro Glu Glu Lys Leu Ala Ala Leu
            180                 185                 190

TGC AAG AAG TAT GCG GAA CTG CTC GAG GAG CAC CGG AAC TCG CAG AAG        684
Cys Lys Lys Tyr Ala Glu Leu Leu Glu Glu His Arg Asn Ser Gln Lys
        195                 200                 205

CAG ATG AAG CTG CTG CAG AAG AAG CAG AGC CAG CTG GTG CAG GAG AAG        732
Gln Met Lys Leu Leu Gln Lys Lys Gln Ser Gln Leu Val Gln Glu Lys
    210                 215                 220

GAC CAC CTG CGT GGC GAG CAC AGC AAG GCC ATC CTG GCC CGC AGC AAG        780
Asp His Leu Arg Gly Glu His Ser Lys Ala Ile Leu Ala Arg Ser Lys
225                 230                 235                 240

CTC GAG AGC CTG TGC CGG GAG CTG CAG CGG CAC AAC CGC TCG CTC AAG        828
Leu Glu Ser Leu Cys Arg Glu Leu Gln Arg His Asn Arg Ser Leu Lys
                245                 250                 255

GAA GAA GGT GTG CAG CGA GCC CGA GAG GAG GAG AAG CGC AAG GAG        876
Glu Glu Gly Val Gln Arg Ala Arg Glu Glu Glu Lys Arg Lys Glu
            260                 265                 270

GTG ACG TCA CAC TTC CAG ATG ACG CTC AAC GAC ATT CAG CTG CAG ATG        924
Val Thr Ser His Phe Gln Met Thr Leu Asn Asp Ile Gln Leu Gln Met
        275                 280                 285
```

```
GAG CAG CAC AAC GAG CGC AAC TCC AAG CTG CGC CAG GAG AAC ATG GAG        972
Glu Gln His Asn Glu Arg Asn Ser Lys Leu Arg Gln Glu Asn Met Glu
            290                 295                 300

CTG GCC GAG CGG CTC AAG AAG CTG ATT GAG CAG TAC GAG CTG CGA GAA       1020
Leu Ala Glu Arg Leu Lys Lys Leu Ile Glu Gln Tyr Glu Leu Arg Glu
305                 310                 315                 320

GAG CAC ATC GAC AAA GTC TTC AAA CAC AAG GAT CTG CAG CAG CAG CTG       1068
Glu His Ile Asp Lys Val Phe Lys His Lys Asp Leu Gln Gln Gln Leu
                325                 330                 335

GTG GAC GCC AAG CTC CAG CAG GCC CAG GAG ATG CTG AAG GAG GCA GAG       1116
Val Asp Ala Lys Leu Gln Gln Ala Gln Glu Met Leu Lys Glu Ala Glu
            340                 345                 350

GAG CGG CAC CAG CGG GAG AAG GAC TTT CTC CTG AAG GAG GCC GTG GAG       1164
Glu Arg His Gln Arg Glu Lys Asp Phe Leu Leu Lys Glu Ala Val Glu
            355                 360                 365

TCC CAG AGG ATG TGC GAG CTG ATG AAG CAA CAG GAG ACC CAC CTG AAG       1212
Ser Gln Arg Met Cys Glu Leu Met Lys Gln Gln Glu Thr His Leu Lys
        370                 375                 380

CAG CAG CTT GCC CTA TAC ACA GAG AAG TTT GAG GAG TTC CAG AAC ACT       1260
Gln Gln Leu Ala Leu Tyr Thr Glu Lys Phe Glu Glu Phe Gln Asn Thr
385                 390                 395                 400

CTT TCC AAA AGC AGC GAG GTG TTC ACC ACA TTC AAA CAG GAA ATG GAA       1308
Leu Ser Lys Ser Ser Glu Val Phe Thr Thr Phe Lys Gln Glu Met Glu
                405                 410                 415

AAG ATG ACA AAG AAG ATC AAG AAG CTG GAG AAA GAG ACC ACC ATG TAC       1356
Lys Met Thr Lys Lys Ile Lys Lys Leu Glu Lys Glu Thr Thr Met Tyr
            420                 425                 430

CGT TCC CGG TGG GAG AGC AGC AAC AAG GCC CTG CTT GAG ATG GCT GAG       1404
Arg Ser Arg Trp Glu Ser Ser Asn Lys Ala Leu Leu Glu Met Ala Glu
            435                 440                 445

GAG AAA ACA CTC CGG GAC AAA GAG CTG GAA GGC CTG CAG GTG AAA ATC       1452
Glu Lys Thr Leu Arg Asp Lys Glu Leu Glu Gly Leu Gln Val Lys Ile
450                 455                 460

CAG CGG CTG GAG AAG CTG TGC CGG GCA CTG CAG ACA GAG CGC AAT GAC       1500
Gln Arg Leu Glu Lys Leu Cys Arg Ala Leu Gln Thr Glu Arg Asn Asp
465                 470                 475                 480

CTG AAC AAG AGG GTG CAG GAC CTG AGT GCC GGT GGC CAG GGC CCC GTC       1548
Leu Asn Lys Arg Val Gln Asp Leu Ser Ala Gly Gly Gln Gly Pro Val
                485                 490                 495

TCC GAC AGC GGT CCT GAG CGG AGG CCA GAG CCC GCC ACC ACC TCC AAG       1596
Ser Asp Ser Gly Pro Glu Arg Arg Pro Glu Pro Ala Thr Thr Ser Lys
            500                 505                 510

GAG CAG GGT GTC GAG GGC CCC GGG GCT CAA GTA CCC AAC TCT CCA AGG       1644
Glu Gln Gly Val Glu Gly Pro Gly Ala Gln Val Pro Asn Ser Pro Arg
            515                 520                 525

GCC ACA GAC GCT TCC TGC TGC GCA GGT GCA CCC AGC ACA GAG GCA TCA       1692
Ala Thr Asp Ala Ser Cys Cys Ala Gly Ala Pro Ser Thr Glu Ala Ser
530                 535                 540

GGC CAG ACA GGG CCC CAG GAG CCC ACC ACT GCC ACT GCC TAGAGAGCTT  GG    1743
Gly Gln Thr Gly Pro Gln Glu Pro Thr Thr Ala Thr Ala
545                 550                 555

TGCTGGGGTG TGCCAGGAAG GGAGCAGGCA GCCCAGCCAG GCCTGGCCCA GCCCAGGCTC     1803

CCATGCTAAG CAGTCCGGTG CTGAGGCCAG GATGTTCTGA CCTGGCTGGC ACCTGACCCT     1863

CTGCAGTCTT GGATTTTGTG GGTCAGTTTT ACATGCATAT GGCACACATG CAAGGCCTCA     1923

CACATTTGTG TCTCTAAGTG TACTGTGGGC TTGCATCGGG GGTGACGATG ACAGATGAA      1983

GCCAGCGGCT CCCTTGTGAG CTGAAGTCTT ACGGAGGAGA CGGCGTCTGC ACTGCCATCG     2043
```

```
CAGTGACCTG CAGGACGAGT TCCTTGAGCT TTCCCTGCCT GCTTTGAGGC TGAGACCCCT    2103

CCCGGCCCTT CAGAGCTCCT GACAGGTGAT ACACACCCAG CCTTGACCGC ACTTCTCTTG    2163

GGTAGCTGGG CTCTCCTAGC CTCCCCCAGA GGCGCCATTG CTTCTCTTGA CTTGGAGAGG    2223

GGATGCCCAG GCGTGGCCTT GGCAGGCACT GGGAGCTAGT GATTGGGCTG CTCTCCTGCC    2283

TCGAGCAGGG GCAGGAGTGT TTCTGGTGGG ATGATGCGCT CGCTGGTCAG GAGCCCCGTG    2343

GGCGCTGCTT CCCCCGCCCT CTGGTGATGC CAGGACCAGG CCAGTGATGC TTCTCAGTAG    2403

CCTTACCATT CACAGGTGCC TCTCCAGCCC GCACAGTGAG TGACAAGATC ATCCAAAGGA    2463

TTCCTTCTGA AGGTGTTCGT TTCGTTTTGT TTTGTTGCAC GTGACGGTTT GTATTGAGGA    2523

CCCTCTGAGG AAGAGGGGTG CTGTAGCAGT GGTCCCTGCG TGCCTGGCTC CAGTGTCCTG    2583

CCCTCCCCCC CCTCGCCATG GCTCCTCGGC CGCCTTGGTG CTGAGGTTTC TGTTTGGTGA    2643

GATCAGGTTG TCTGTTCAGA GAAGAGGC GTCTGATGGC TTTGCCGCCA GCTTGCCTGC    2703

GGGCCTCAAT CCCGGGAGGC CGCCCGGTTC CCGTCACTGT TGTCCCCGTG CAGTGCGTTG    2763

CTGGTCCCCA GGACCAGCTG CTCGTTTGCT GTATGGGTCA GTTTCTGCTT CCTGCCCCCC    2823

ACTCCACCTA ACTGCAATCC TTGGGGTTTC CCTGGTTCTC GTCCCTGGTA CCTCTGTGCC    2883

CAAGAAGTAG CCTTCTTTGG GATTCTTGTT CTGCCCATGC GGGAGCTGCT GCTGTCTGAC    2943

AGGTGAGGCC TGAGACTCAG CGGCTGACAG AGCTGCAGAG CTCTGCACGG TGGCTCCCGG    3003

GGCGGCCTCT GTGTGCTGCA CACCGCTGCT CTGCTGGCAC TGGCCAGTCT GTGCAGAGCA    3063

TTTGAGTACT GGCTCAGGAG GGAGGGCTCT GCTGGCCTCG AGGGACAGCG CCACGTCTCC    3123

AGCTGGGCTC AGGGAGAGCC CCAGACTGGC TGCGTAGGGT GCTTGGGGTT TGCTTCTTGC    3183

AGTATTTCTT GGAAGCTGTT TTGTTGTCCT GCTATTCCTT CATCTTCCAC AGTCCACGCT    3243

CAGCCTTTAA CTTGGATCCC TCACATAACA GGGTTCATGA GACCCGCAAG TACGCCCAAG    3303

CTACGTATGG CTGAGGCCAG CTGGCAGGTG AATGGCACGC CATTGCTGCT GCTAATCCCT    3363

GGCATATCTT TAGTTCACCT CGAAATGCCC CCGCCACAGT GCAAGCAGTG AGTCCACGTG    3423

CCACCCTGGG CTGAATCCCA CCCCCTGTGA GTGTTGCCCG AGATTGTGTC TCTTCTGAAT    3483

GCCTTCACTG GGAATGGCCT CTGCCGCCTC CTGCTCAGGG AGGCTTTCCC CTTCCCTCAG    3543

CCCCTGTGCC AGACTGAGGT ACAAGAACCG CCAAGCCCAT GCAAGGTGTG GCTAGGCGCC    3603

AGGGTGCAGG AAGGAGGCAG GTAGCTGCCT GCACCCTTGA AAGCCAAGAG GCCTACGGTG    3663

GCCTCCATCC TGGCTTGCCT CACTTCAGCT ACCTCGCATA GCCCAGGGGT GGGGCTATTG    3723

GATTCCAGGG TGGGGGATG GGAAGCTGCA GGGGCAGGT GGCTCTCACT AGGCTTCCCA    3783

GCTCAGGAAT GTGGGCCTCA GGTAGGGGAG AGCCTTTGCT CCACTCCACC CATTTGCAGG    3843

CATCTAGGCC AGTCTAGATG GCGACCCCTT CTCTTCCTCT CCATTGACCA AATCGTACCT    3903

GTCTCTCCAG CTGCTCGCTT GCTCTGCTTT CCAAAGTCAG CCCAGGTACC CAGGTGCCGC    3963

CCACATTGGC CTGGAACCTG GACCAGAGGC AAGGGAGGTG GCCTATCCTT GAGTGATAGC    4023

CAGTGCCTTC CTCACCCGGT GGCTTCCATG CCTGTGACCT CAGATTTAGG ACCAAGAGCT    4083

GTGTTGGTTT CTTACGTTGT GAGCTTTCCC TCCAGGGAC CACAGCAGGT GAGGCTCGGA    4143

GCCCAGAGCC CTTGGCGCCG CCAGCAGTAA CTTGTGTCCG GACCTTGTCC AGCTGAGCGC    4203

TTCGTGTATG ACTCAGCTTC GTGTGTGAGT CCAGCGGAGT GCGTCACGTG ACCTAGACTC    4263

AGCGGTGTCA GCCGCACTTT GATTTGTTTG TTTTCCATGA GGTTTTTGGA CCATGGGCTT    4323

AGCTCAGGCA ACTTTTCTGT AAGGAGAATG TTAACTTTCT GTAAAGATGC TTATTTAACT    4383

AACGCCTGCT TCCCCCACTC CCAACCAGGT GGCCACCGAG AGCTCACCAG GAGGCCAATA    4443
```

```
GAGCTGCTCC AGCTCTCCCA TCTTGCACCG CACAAAGGTG GCCGCCCCAG GGACAGCCAG      4503

GCACCTGCCT GGGGGAGGGG CTTCTCTTCC TTATGGCCTG GCCATCTAGA TTGTTTAAAG      4563

TTGTGCTGAC AGCTTTTTTT GGTTTTTTGG TTTTTGTTTT TGTTTTTGTT TTTGTTTTTG      4623

TCTACTTTTG GTATTCACAA CAGCCAGGGA CTTGATTTTG ATGTATTTTA AGCCACATTA      4683

AATAAAGAGT CTGTTGCCTT AAAAAAAAAA AAAAAAAA                              4722

(2) INFORMATION FOR SEQ ID NO: 15:

(i) SEQUENCE CHARACTERISTICS:
        (A) LENGTH: 1925 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 118...570

(xi) SEQUENCE DESCRIPTION: SEQ ID NO: 15:

GACGCCTCAG AGCGGAACAG GGAAGTGAAT CAGGCGCCGG GTAGTGGGTT GCTGGGCTGG        60

GCTTGCTGAG GTAGAGGCAG CGCCAAGAAG AGGCCTTTGC CGCTGGTCGG GATTGGG ATG      120
                                                                Met
                                                                  1

TCG AAG AAC ACA GTG TCG TCG GCC CGC TTC CGG AAG GTG GAC GTG GAT         168
Ser Lys Asn Thr Val Ser Ser Ala Arg Phe Arg Lys Val Asp Val Asp
              5                  10                  15

GAA TAT GAC GAG AAC AAG TTC GTG GAC GAA GAA GAT GGG GGC GAC GGC         216
Glu Tyr Asp Glu Asn Lys Phe Val Asp Glu Glu Asp Gly Gly Asp Gly
         20                  25                  30

CAG GCC GGG CCC GAC GAG GGC GAG GTG GAC TCC TGC CTG CGG CAA GGA         264
Gln Ala Gly Pro Asp Glu Gly Glu Val Asp Ser Cys Leu Arg Gln Gly
     35                  40                  45

AAC ATG ACA GCT GCC CTA CAG GCA GCT CTG AAG AAC CCC CCT ATC AAC         312
Asn Met Thr Ala Ala Leu Gln Ala Ala Leu Lys Asn Pro Pro Ile Asn
 50                  55                  60                  65

ACC AAG AGT CAG GCA GTG AAG GAC CGG GCA GGC AGC ATT GTC TTG AAG         360
Thr Lys Ser Gln Ala Val Lys Asp Arg Ala Gly Ser Ile Val Leu Lys
                 70                  75                  80

GTG CTC ATC TCT TTT AAA GCT AAT GAT ATA GAA AAG GCA GTT CAA TCT         408
Val Leu Ile Ser Phe Lys Ala Asn Asp Ile Glu Lys Ala Val Gln Ser
             85                  90                  95

CTG GAC AAG AAT GGT GTG GAT CTC CTA ATG AAG TAT ATT TAT AAA GGA         456
Leu Asp Lys Asn Gly Val Asp Leu Leu Met Lys Tyr Ile Tyr Lys Gly
         100                 105                 110

TTT GAG AGC CCG TCT GAC AAT AGC AGT GCT ATG TTA CTG CAA TGG CAT         504
Phe Glu Ser Pro Ser Asp Asn Ser Ser Ala Met Leu Leu Gln Trp His
     115                 120                 125

GAA AAG GCA CTT GCT GCT GGA GGA GTA GGG TCC ATT GTT CGT GTC TTG         552
Glu Lys Ala Leu Ala Ala Gly Gly Val Gly Ser Ile Val Arg Val Leu
130                 135                 140                 145

ACT GCA AGA AAA ACT GTG TAGTCTGGCA GGAAGTGGAT TATCTGCCTC GGGAGT         608
Thr Ala Arg Lys Thr Val
                150

GAATTGCTGG TACAAAGACC AAAACAACCA AATGCCACCG CTGCCCTGTG GGTAGCATCT      668

GTTTCTCTCA GCTTTGCCTT CTTGCTTTTT CATATCTGTA AAGAAAAAAA TTACATATCA      728

GTTGTCCCTT TAATGAAAAT TGGGATAATA TAGAAGAAAT TGTGTTAAAA TAGAAGTGTT      788

TCATCCTTTC AAAACCATTT CAGTGATGTT TATACCAATC TGTATATAGT ATAATTTACA      848
```

-continued

```
TTCAAGTTTT AATTGTGCAA CTTTTAACCC TGTTGGCTGG TTTTTGGTTC TGTTTGGTTT    908

TGTATTATTT TTAACTAATA CTGAAAAATT TGGTCAGAAT TTGAGGCCAG TTTCCTAGCT    968

CATTGCTAGT CAGGAAATGA TATTTATAAA AAATATGAGA GACTGGCAGC TATTAACATT   1028

GCAAAACTGG ACCATATTTC CCTTATTTAA TAAGCAAAAT ATGTTTTTGG AATAAGTGGT   1088

GGGTGAATAC CACTGCTAAG TTATAGCTTT GTTTTTGCTT GCCTCCTCAT TATCTGTACT   1148

GTGGGTTTAA GTATGCTACT TTCTCTCAGC ATCCAATAAT CATGGCCCCT CAATTTATTT   1208

GTGGTCACGC AGGGTTCAGA GCAAGAAGTC TTGCTTTATA CAAATGTATC CATAAAATAT   1268

CAGAGCTTGT TGGGCATGAA CATCAAACTT TTGTTCCACT AATATGGCTC TGTTTGGAAA   1328

AAACTGCAAA TCAGAAAGAA TGATTTGCAG AAAGAAAGAA AAACTATGGT GTAATTTAAA   1388

CTCTGGGCAG CCTCTGAATG AAATGCTACT TTCTTTAGAA ATATAATAGC TGCCTTAGAC   1448

ATTATGAGGT ATACAACTAG TATTTAAGAT ACCATTTAAT ATGCCCCGTA AATGTCTTCA   1508

GTGTTCTTCA GGGTAGTTGG GATCTCAAAA GATTTGGTTC AGATCCAAAC AAATACACAT   1568

TCTGTGTTTT AGCTCAGTGT TTTCTAAAAA AAGAAACTGC CACACAGCAA AAAATTGTTT   1628

ACTTTGTTGG ACAAACCAAA TCAGTTCTCA AAAAATGACC GGTGCTTATA AAAAGTTATA   1688

AATATCGAGT AGCTCTAAAA CAAACCACCT GACCAAGAGG GAAGTGAGCT TGTGCTTAGT   1748

ATTTACATTG GATGCCAGTT TTGTAATCAC TGACTTATGT GCAAACTGGT GCAGAAATTC   1808

TATAAACTCT TTGCTGTTTT TGATACCTGC TTTTTGTTTC ATTTTGTTTT GTTTTGTAAA   1868

AATGATAAAA CTTCAGAAAA TAAAATGTCA GTGTTGAATA ATTAAAAAAA AAAAAAA     1925
```

(2) INFORMATION FOR SEQ ID NO: 16:

(i) SEQUENCE CHARACTERISTICS:
  (A) LENGTH: 1208 base pairs
  (B) TYPE: nucleic acid
  (C) STRANDEDNESS: single
  (D) TOPOLOGY: linear (ix) FEATURE:
  (A) NAME/KEY: Coding Sequence
  (B) LOCATION: 1...651

(xi) SEQUENCE DESCRIPTION: SEQ ID NO: 16:

```
GAA GAG CGA GTA CTT GAG AAA GAA GAG GAA GAA GAT GAT GAT GAA GAT        48
Glu Glu Arg Val Leu Glu Lys Glu Glu Glu Glu Asp Asp Asp Glu Asp
  1               5                  10                  15

GAA GAT GAA GAA GAT GAT GTG TCA GAG GGC TCT GAA GTG CCC GAG AGT        96
Glu Asp Glu Glu Asp Asp Val Ser Glu Gly Ser Glu Val Pro Glu Ser
             20                  25                  30

GAC CGT CCT GCA GGT GCC CAG CAC CAC CAG CTT AAC GGC GAG CGG GGA       144
Asp Arg Pro Ala Gly Ala Gln His His Gln Leu Asn Gly Glu Arg Gly
         35                  40                  45

CCT CAG AGT GCC AAG GAG AGG GTC AAG GAG TGG ACC CCC TGC GGA CCG       192
Pro Gln Ser Ala Lys Glu Arg Val Lys Glu Trp Thr Pro Cys Gly Pro
     50                  55                  60

CAC CAG GGC CAG GAT GAA GGG CGG GGG CCA GCC CCG GGC AGC GGC ACC       240
His Gln Gly Gln Asp Glu Gly Arg Gly Pro Ala Pro Gly Ser Gly Thr
 65                  70                  75                  80

CGC CAG GTG TTC TCC ATG GCA GCC ATG AAC AAG GAA GGG GGA ACA GCT       288
Arg Gln Val Phe Ser Met Ala Ala Met Asn Lys Glu Gly Gly Thr Ala
                 85                  90                  95

TCT GTT GCC ACC GGG CCA GAC TCC CCG TCC CCC GTG CCT TTG CCC CCA       336
Ser Val Ala Thr Gly Pro Asp Ser Pro Ser Pro Val Pro Leu Pro Pro
            100                 105                 110
```

-continued

```
GGC AAA CCA GCC CTA CCT GGG GCC GAC GGG ACC CCC TTT GGC TGT CCT        384
Gly Lys Pro Ala Leu Pro Gly Ala Asp Gly Thr Pro Phe Gly Cys Pro
        115                 120                 125

CCC GGG CGC AAA GAG AAG CCA TCT GAT CCC GTC GAG TGG ACC GTG ATG        432
Pro Gly Arg Lys Glu Lys Pro Ser Asp Pro Val Glu Trp Thr Val Met
130                 135                 140

GAT GTC GTC GAA TAT TTT ACT GAG GCT GGA TTC CCG GAG CAG GCG ACA        480
Asp Val Val Glu Tyr Phe Thr Glu Ala Gly Phe Pro Glu Gln Ala Thr
145                 150                 155                 160

GCT TTC CAA GAG CAG GAA ATT GAT GGC AAA TCT TTG CTG CTC ATG CAG        528
Ala Phe Gln Glu Gln Glu Ile Asp Gly Lys Ser Leu Leu Leu Met Gln
                165                 170                 175

CGC ACA GAT GTG CTC ACC GGC CTG TCC ATC CGC CTC GGG CCA GCC CTG        576
Arg Thr Asp Val Leu Thr Gly Leu Ser Ile Arg Leu Gly Pro Ala Leu
            180                 185                 190

AAA ATC TAC GAG CAC CAC ATC AAG GTG CTT CAG CAA GGC CAC TTT GAG        624
Lys Ile Tyr Glu His His Ile Lys Val Leu Gln Gln Gly His Phe Glu
        195                 200                 205

GAT GAT GAC CCC GAT GGC TTC TTA GGC TGAGCGCCCA GCCTCACCCC TGCCCCA      678
Asp Asp Asp Pro Asp Gly Phe Leu Gly
    210                 215

GCCCATTCCG GCCCCCATCT CACCCAAGAT CCCCCAGAGT CCAGGAGCTG GACGGGGACA       738

CCCTCAGCCC TCATAACAGA TTCCAAGGAG AGGGCACCCT CTTGTCCTTA TCTTTGCCCC       798

TTGTGTCTGT CTCACACACA TCTGCTCCTC AGCACGTCGG TGTGGGGAGG GGATTGCTCC       858

TTAAACCCCA GGTGGCTGAC CCTCCCCACC CAGTCCAGGA CATTTTAGGA AAAAAAAAAT       918

GAAATGTGGG GGGCTTCTCA TCTCCCCAAG ATCCTCTTCC GTTCAGCCAG ATGTTTCCTG       978

TATAAATGTT TGGATCTGCC TGTTTATTTT GGTGGGTGGT CTTTCCTCCC TCCCCTACCA      1038

CCCATGCCCC CCTTCTCAGT CTGCCCCTGG CCTCCAGCCC CTAGGGGACT AGCTGGGTTG      1098

GGGTTCCTCG GGCCTTTTCT CTCCTCCCTC TTTTCTTTCT GTTGATTGTC GCTCCAGCTG      1158

GCTGTATTGC TTTTTAATAT TGCACCGAAG GTTTTTTAAA TAAAATTTTA                 1208

(2) INFORMATION FOR SEQ ID NO: 17:

(i) SEQUENCE CHARACTERISTICS:
        (A) LENGTH: 4697 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 3...1592

(xi) SEQUENCE DESCRIPTION: SEQ ID NO: 17:

CA AAA AGC AGC CCA GGA CAA CCG GAA GCA GGA CCC GAG GGA GCC CAG         47
   Lys Ser Ser Pro Gly Gln Pro Glu Ala Gly Pro Glu Gly Ala Gln
   1               5                   10                  15

GAG CGG CCC AGC CAG GCG GCT CCT GCA GTA GAA GCA GAA GGT CCC GGC        95
Glu Arg Pro Ser Gln Ala Ala Pro Ala Val Glu Ala Glu Gly Pro Gly
            20                  25                  30

AGC AGC CAG GCT CCT CGG AAG CCG GAG GGG GCT CAA GCC AGA ACG GCT       143
Ser Ser Gln Ala Pro Arg Lys Pro Glu Gly Ala Gln Ala Arg Thr Ala
        35                  40                  45

CAG TCT GGG GCC CTT CGT GAT GTC TCT GAG GAG CTG AGC CGC CAA CTG       191
Gln Ser Gly Ala Leu Arg Asp Val Ser Glu Glu Leu Ser Arg Gln Leu
    50                  55                  60

GAA GAC ATA CTG AGC ACA TAC TGT GTG GAC AAT AAC CAG GGG GGC CCC       239
```

```
                    -continued

Glu Asp Ile Leu Ser Thr Tyr Cys Val Asp Asn Asn Gln Gly Gly Pro
 65                  70                  75

GGC GAG GAT GGG GCA CAG GGT GAG CCG GCT GAA CCC GAA GAT GCA GAG      287
Gly Glu Asp Gly Ala Gln Gly Glu Pro Ala Glu Pro Glu Asp Ala Glu
 80                  85                  90                  95

AAG TCC CGG ACC TAT GTG GCA AGG AAT GGG GAG CCT GAA CCA ACT CCA      335
Lys Ser Arg Thr Tyr Val Ala Arg Asn Gly Glu Pro Glu Pro Thr Pro
                    100                 105                 110

GTA GTC TAT GGA GAG AAG GAA CCC TCC AAG GGG GAT CCA AAC ACA GAA      383
Val Val Tyr Gly Glu Lys Glu Pro Ser Lys Gly Asp Pro Asn Thr Glu
             115                 120                 125

GAG ATC CGG CAG AGT GAC GAG GTC GGA GAC CGA GAC CAT CGA AGG CCA      431
Glu Ile Arg Gln Ser Asp Glu Val Gly Asp Arg Asp His Arg Arg Pro
     130                 135                 140

CAG GAG AAG AAA AAA GCC AAG GGT TTG GGG AAG GAG ATC ACG TTG CTG      479
Gln Glu Lys Lys Lys Ala Lys Gly Leu Gly Lys Glu Ile Thr Leu Leu
145                 150                 155

ATG CAG ACA TTG AAT ACT CTG AGT ACC CCA GAG GAG AAG CTG GCT GCT      527
Met Gln Thr Leu Asn Thr Leu Ser Thr Pro Glu Glu Lys Leu Ala Ala
160                 165                 170                 175

CTG TGC AAG AAG TAT GCT GAA CTG CTG GAG GAG CAC CGG AAT TCA CAG      575
Leu Cys Lys Lys Tyr Ala Glu Leu Leu Glu Glu His Arg Asn Ser Gln
                    180                 185                 190

AAG CAG ATG AAG CTC CTA CAG AAA AAG CAG AGC CAG CTG GTG CAA GAG      623
Lys Gln Met Lys Leu Leu Gln Lys Lys Gln Ser Gln Leu Val Gln Glu
             195                 200                 205

AAG GAC CAC CTG CGC GGT GAG CAC AGC AAG GCC GTC CTG GCC CGC AGC      671
Lys Asp His Leu Arg Gly Glu His Ser Lys Ala Val Leu Ala Arg Ser
     210                 215                 220

AAG CTT GAG AGC CTA TGC CGT GAG CTG CAG CGG CAC AAC CGC TCC CTC      719
Lys Leu Glu Ser Leu Cys Arg Glu Leu Gln Arg His Asn Arg Ser Leu
225                 230                 235

AAG GAA GAA GGT GTG CAG CGG GCC CGG GAG GAG GAG GAG AAG CGC AAG      767
Lys Glu Glu Gly Val Gln Arg Ala Arg Glu Glu Glu Glu Lys Arg Lys
240                 245                 250                 255

GAG GTG ACC TCG CAC TTC CAG GTG ACA CTG AAT GAC ATT CAG CTG CAG      815
Glu Val Thr Ser His Phe Gln Val Thr Leu Asn Asp Ile Gln Leu Gln
                    260                 265                 270

ATG GAA CAG CAC AAT GAG CGC AAC TCC AAG CTG CGC CAA GAG AAC ATG      863
Met Glu Gln His Asn Glu Arg Asn Ser Lys Leu Arg Gln Glu Asn Met
             275                 280                 285

GAG CTG GCT GAG AGG CTC AAG AAG CTG ATT GAG CAG TAT GAG CTG CGC      911
Glu Leu Ala Glu Arg Leu Lys Lys Leu Ile Glu Gln Tyr Glu Leu Arg
     290                 295                 300

GAG GAG CAT ATC GAC AAA GTC TTC AAA CAC AAG GAC CTA CAA CAG CAG      959
Glu Glu His Ile Asp Lys Val Phe Lys His Lys Asp Leu Gln Gln Gln
305                 310                 315

CTG GTG GAT GCC AAG CTC CAG CAG GCC CAG GAG ATG CTA AAG GAG GCA     1007
Leu Val Asp Ala Lys Leu Gln Gln Ala Gln Glu Met Leu Lys Glu Ala
320                 325                 330                 335

GAA GAG CGG CAC CAG CGG GAG AAG GAT TTT CTC CTG AAA GAG GCA GTA     1055
Glu Glu Arg His Gln Arg Glu Lys Asp Phe Leu Leu Lys Glu Ala Val
                    340                 345                 350

GAG TCC CAG AGG ATG TGT GAG CTG ATG AAG CAG CAA GAG ACC CAC CTG     1103
Glu Ser Gln Arg Met Cys Glu Leu Met Lys Gln Gln Glu Thr His Leu
             355                 360                 365

AAG CAA CAG CTT GCC CTA TAC ACA GAG AAG TTT GAG GAG TTC CAG AAC     1151
Lys Gln Gln Leu Ala Leu Tyr Thr Glu Lys Phe Glu Glu Phe Gln Asn
     370                 375                 380
```

```
ACA CTT TCC AAA AGC AGC GAG GTA TTC ACC ACA TTC AAG CAG GAG ATG      1199
Thr Leu Ser Lys Ser Ser Glu Val Phe Thr Thr Phe Lys Gln Glu Met
        385                 390                 395

GAA AAG ATG ACT AAG AAG ATC AAG AAG CTG GAG AAA GAA ACC ACC ATG      1247
Glu Lys Met Thr Lys Lys Ile Lys Lys Leu Glu Lys Glu Thr Thr Met
400                 405                 410                 415

TAC CGG TCC CGG TGG GAG AGC AGC AAC AAG GCC CTG CTT GAG ATG GCT      1295
Tyr Arg Ser Arg Trp Glu Ser Ser Asn Lys Ala Leu Leu Glu Met Ala
                420                 425                 430

GAG GAG AAA ACA GTC CGG GAT AAA GAA CTG GAG GGC CTG CAG GTA AAA      1343
Glu Glu Lys Thr Val Arg Asp Lys Glu Leu Glu Gly Leu Gln Val Lys
            435                 440                 445

ATC CAA CGG CTG GAG AAG CTG TGC CGG GCA CTG CAG ACA GAG CGC AAT      1391
Ile Gln Arg Leu Glu Lys Leu Cys Arg Ala Leu Gln Thr Glu Arg Asn
        450                 455                 460

GAC CTG AAC AAG AGG GTA CAG GAC CTG AGT GCT GGT GGC CAG GGC TCC      1439
Asp Leu Asn Lys Arg Val Gln Asp Leu Ser Ala Gly Gly Gln Gly Ser
    465                 470                 475

CTC ACT GAC AGT GGC CCT GAG AGG AGG CCA GAG GGG CCT GGG GCT CAA      1487
Leu Thr Asp Ser Gly Pro Glu Arg Arg Pro Glu Gly Pro Gly Ala Gln
480                 485                 490                 495

GCA CCC AGC TCC CCC AGG GTC ACA GAA GCG CCT TGC TAC CCA GGA GCA      1535
Ala Pro Ser Ser Pro Arg Val Thr Glu Ala Pro Cys Tyr Pro Gly Ala
                500                 505                 510

CCG AGC ACA GAA GCA TCA GGC CAG ACT GGG CCT CAA GAG CCC ACC TCC      1583
Pro Ser Thr Glu Ala Ser Gly Gln Thr Gly Pro Gln Glu Pro Thr Ser
            515                 520                 525

GCC AGG GCC TAGAGAGCCT GGTGTTGGGT CATGCTGGGA AGGGAGCGGC AGCCCAGCC    1641
Ala Arg Ala
        530

AGGCCTGGCC CATAAAAGGC TCCCATGCTG AGCAGCCCAT TGCTGAAGCC AGGATGTTCT    1701

TGACCTGGCT GGCATCTGGC ACTTGCAATT TTGGATTTTG TGGGTCAGTT TTACGTACAT    1761

AGGGCATTTT GCAAGGCCTT GCAAATGCAT TTATACCTGT AAGTGTACAG TGGGCTTGCA    1821

TTGGGATGG GGGTGTGTAC AGATGAAGTC AGTGGCTTGC CTGTGAGCTG AAGAGTCTTG     1881

AGAGGGCTG TCATCTGTAG CTGCCATCAC AGTGAGTTGG CAGAAGTGAC TTGAGCATTT     1941

CTCTGTCTGA TTTGAGGCTC AGACCCCTCC CTGCCCTTTC AGAGCTCAAA ACAAGTAATA    2001

CACCAAGGTC TTGACTGCAT TTGTCTTGTG AGCAGGGCTT GCTTGGTCAG CTCAGGCCCT    2061

CCTAGCTGCT TGGAGGCTCC TTTGATTCTC TAGACCTGGA AAAGGTGTCC CTAGGCAGAG    2121

CCCTGGCAGG GCGCTCAGAG CTGGGATTTC CTGCCTGGAA CAAGGGACCT GGAGAATGTT    2181

TTTGCGTGGG ATGATGTGCT GGTCAGGAGC CCCTTGGGCA TCGCTTCCCC TGCCCTTTGG    2241

TAGTGCCAGG ACCAGGCCAA TGATGCTTCT CAGTAGCCTT ATCATTCACA GGTGCCTCTC    2301

TAGCCTGCAC AAATGATTGA CAAGAGATCA CCCAAAGGAT TATTTCTGAA GGTGTTTTTT    2361

TCTTTATTTC TTTTTCTTTT TTTTTTTTC TTTTTCTTTT TTTTTGCAC ATGACAGTGT      2421

TTGTATTGAG GACCTTCCAA GGAAAAGGGA TGCTGTACCA GTGGTGCCTG GGTGCCTGGC    2481

CTCCAGTGTC CCACCTCCTT CACCACCCCA CTTGGCTCCT TTGCCATCTT GATGCTGAGG    2541

TTTCCTGTTT GGTGAGATCA GGTTGTTTGT GGTAAAAGAA AGGAAAGGGC TTCTGATGGC    2601

TTTGCCACAA GCTTACCTGT GGGTTTCAGT CCTGAGAGGC CACCACCAGT TCCCATCAGC    2661

ACTGTCTCCA TGCAGCAGTT GCTGGGTCCC ATGTCCAGCT GCCTCTTTGG CTTCATGGGT    2721

TTTTCTGCTT CCTGCCCCCA CCCCCACATG TGCAATCCTC AAGATTTGTC CTGATTCTAT    2781

TTCCTGGCAC CTCCCTGCCT GTCCTTGGGG ATTCTACTTC TTCCTGTGTG GGCCCATAG    2841
```

-continued

```
CTGTTGTCTA ACAGGTAAGA AATGAAATTG AACTATTGAC TGGGCCCCAG AAATCCATAA    2901

AATGGCTGCA GACAGTTGTT TCTGTGTCCT GTTCTACCCC CACTCCAGTA CATAACTACT    2961

ATGTACTGTG TAGAGCCATT CTATATGCTG AATGTTCTGC TGTTGCAAAC TTGCCAGGGT    3021

ATTAGCCAGT GTTTGTGCCA AGCAGTTTTC GGGGACAACA GAATGACTCA GACCAAGATG    3081

GATAGGATGG TTAGGGCTTT GCTTCTTGCT GTTTTTCTTT GAACTAGTCA TTGTCCTGCA    3141

GGTCCCTTCA TCTTCCATAC CTAGCCCACT CTTTTAGCCC TTACCTTAAA TCTCTCAGAT    3201

AAGTTGGTTC ACAAAGAATG TTAAGTACTG AATCATGTGT GACTGAGACC AGAGATGGCA    3261

AATGAATGGC ACACCATTTC TCCTTCTCCT GCCCCAGGGC AGGTACCACT GATCTGCATC    3321

AGAGTTGCCT GCTATTCTCT GGTGTATCCT TCACATCTAG GTGCCCTCAA GCAGCTGTGT    3381

GAGTGTTGAG ATCTCTGCCA TCTCTGGCTG AGATACTGCT GTCCTGTGAA GTGTTTCCCA    3441

TGACCTTTTT CTTCCCCTTT GAATCCCTCT TGTCTGGAGT AGTCCTTGCC TTCTTCTTGC    3501

TCCAGTAGGC CTTTTCCTTA CCCCAGCCCT TGTGCCAGGC TAAGCTGGTA CAAGAGCTTGC   3561

CAACTCACAG AGTTTTGCTA GGCGAGAGAG GTGCAGGGAA GAGGCAGAGG TATGCACCTT    3621

CCCCCTTGAA GAGAGGGGAA AGGCCTACAG TGGCCCACAT AATTGCCTGA CTCACACTTC    3681

AGCTACCTCT TAATGCCTGT GGAGGGACTG GAGCTGCTGG ATCCCAGTGT GGTGGTGTAG    3741

GAGGCCACAG TGAGCAGGTG GCCCCAGCTG GGTTTCCCAG GTCAGGAATG TGGGCCCCAG    3801

GCAAGGTGCA GCCTTTGCTC ACAGCTCCAT CCATGTCTAG ACCTTCAGGC CAGTCTGCAG    3861

ATGAGGTTCC CTACCTTTTT CTTCTCTTCA TTGACCAAAT CAACCAATCA CTACAGCTGC    3921

TCTGCTTCTG CTTTCCAAAG TAGCCCAGGT CCTGGGCCAG ATGCAGGGGA GGTGCCTATC    3981

CATGAGTGAA GGCCAGTGTC TTCCTCACCT GGGTGGTCCC ACACTTGTGA CCCTCAGTTT    4041

TAGGACCCAA GATCTGTGTT GGTTTCTTAG ATTGCTAGCT TTTCCTCCAG GGACCACAG    4101

CAGGTGAAGC TCAAGAGCGC ATGGCTCTGC TAATAGTAAA TTGTTTTCAG GGCCTTGTCC    4161

AGCTGAGAGC TTCATGTCCA CCAGATTCTG AGAGGTGTCA GCAGCACTTT TTTTTTTTAT    4221

TTGTTGTTTG TTTTCCATGA GGTTATCGGA CCATGGGCTG AGCTCAGGCA CTTTCTGTAG    4281

GAGACTGTTA TTTCTGTAAA GATGGTTATT TAACCCTCCT CCACCCCATC ACGGTGGCCC    4341

TGAGGGCTGA CCCGGAGGCC AGTGGAGCTG CCTGGTGTCC ACGGGGGAGG GCCAAGGCCT    4401

GCTGAGCTGA TTCTCCAGCT GCTGCCCCAG CCTTTCCGCC TTGCACAGCA CAGAGGTGGT    4461

CACCCCAGGG ACAGCCAGGC ACCTGCTCCT CTTGCCCTTC CTGGGGGAAA GGAGCTGCCT    4521

TCTGTCCCTG TAACTGCTTT CCTTATGGCC CAACCCGGCC ACTCAGACTT GTTTGAAGCT    4581

GCACTGGCAG CTTTTTTGTC TCCTTTGGGT ATTCACAACA GCCAGGGACT TGATTTTGAT    4641

GTATTTTAAA CCACATTAAA TAAAGAGTCT GTTGCCTTAA AAAAAAAAAA AAAAAA       4697
```

(2) INFORMATION FOR SEQ ID NO: 18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...60

(xi) SEQUENCE DESCRIPTION: SEQ ID NO: 18:

```
GTG GAC GTG GAT GAG TAC GAC GAG AAC AAG TTC GTG GAC GAG GAA GAC        48
```

```
Val Asp Val Asp Glu Tyr Asp Glu Asn Lys Phe Val Asp Glu Glu Asp
 1               5                  10                  15

GGC GGC GAC GGC                                                      60
Gly Gly Asp Gly
            20
```

(2) INFORMATION FOR SEQ ID NO: 19:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 19:

```
Glu Glu Glu Glu Asp Asp Asp Glu Asp Glu Asp Glu Glu Asp Asp
 1               5                  10                  15
```

(2) INFORMATION FOR SEQ ID NO: 20:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 20:

```
Glu Glu Glu Glu Asp Asp Asp Glu Asp Glu Asp Glu Glu Asp Asp Val
 1               5                  10                  15

Ser Glu Gly Ser Glu Val Pro Glu Ser Asp
            20                  25
```

(2) INFORMATION FOR SEQ ID NO: 21:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 21:

```
Val Ser Glu Gly Ser Glu Val Pro Glu Ser Asp
 1               5                  10
```

(2) INFORMATION FOR SEQ ID NO: 22:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 22:

```
Glu Asp Asp Asp Pro Asp Gly Phe Leu Gly
 1               5                  10
```

(2) INFORMATION FOR SEQ ID NO: 23:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO: 23:

Val Asp Val Asp Glu Tyr Asp Glu Asn Lys Phe Val Asp Glu Glu Asp
 1               5                  10                  15
Gly Gly Asp Gly Gln Ala Gly Pro Asp Glu Gly Glu Val Asp
            20                  25                  30

(2) INFORMATION FOR SEQ ID NO: 24:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 24:

Asp Glu Gly Glu Val Asp
 1               5

(2) INFORMATION FOR SEQ ID NO: 25:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 25:

Glu Glu Glu Glu Glu Glu Glu Glu Asp Asp Glu Asp Asp Asp Asp Asp
 1               5                  10                  15

(2) INFORMATION FOR SEQ ID NO: 26:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 26:

Glu Glu Glu Glu Glu Glu Glu Glu Asp Asp Glu Asp Asp Asp Asp Asp
 1               5                  10                  15
Val Val Ser Glu Gly Ser Glu Val Pro Glu Ser Asp
            20                  25

(2) INFORMATION FOR SEQ ID NO: 27:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 27:

Val Val Ser Glu Gly Ser Glu Val Pro Glu Ser Asp
 1               5                  10

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 28:

Pro Pro Gly Lys Pro Ala Leu Pro Gly Ala
 1               5                  10

(2) INFORMATION FOR SEQ ID NO: 29:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 29:

Glu Asp Gly Val Gln Gly Glu Pro Pro Glu Pro Glu Asp Ala Glu
 1               5                  10                  15

(2) INFORMATION FOR SEQ ID NO: 30:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...45

(xi) SEQUENCE DESCRIPTION: SEQ ID NO: 30:

GAA GAG GAA GAA GAT GAT GAT GAA GAT GAA GAT GAA GAA GAT GAT          45
Glu Glu Glu Glu Asp Asp Asp Glu Asp Glu Asp Glu Glu Asp Asp
 1               5                  10                  15

(2) INFORMATION FOR SEQ ID NO: 31:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...78

(xi) SEQUENCE DESCRIPTION: SEQ ID NO: 31:

GAA GAG GAA GAA GAT GAT GAT GAA GAT GAA GAT GAA GAA GAT GAT GTG      48
Glu Glu Glu Glu Asp Asp Asp Glu Asp Glu Asp Glu Glu Asp Asp Val
 1               5                  10                  15

TCA GAG GGC TCT GAA GTG CCC GAG AGT GAC                              78
Ser Glu Gly Ser Glu Val Pro Glu Ser Asp
                 20                  25

(2) INFORMATION FOR SEQ ID NO: 32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...33

(xi) SEQUENCE DESCRIPTION: SEQ ID NO: 32:

```
GTG TCA GAG GGC TCT GAA GTG CCC GAG AGT GAC                    33
Val Ser Glu Gly Ser Glu Val Pro Glu Ser Asp
 1               5                  10
```

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...30

(xi) SEQUENCE DESCRIPTION: SEQ ID NO: 33:

```
GAG GAT GAT GAC CCC GAT GGC TTC TTA GGC                        30
Glu Asp Asp Asp Pro Asp Gly Phe Leu Gly
 1               5                  10
```

(2) INFORMATION FOR SEQ ID NO: 34:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...90

(xi) SEQUENCE DESCRIPTION: SEQ ID NO: 34:

```
GTG GAC GTG GAT GAA TAT GAC GAG AAC AAG TTC GTG GAC GAA GAA GAT    48
Val Asp Val Asp Glu Tyr Asp Glu Asn Lys Phe Val Asp Glu Glu Asp
 1               5                  10                  15

GGG GGC GAC GGC CAG GCC GGG CCC GAC GAG GGC GAG GTG GAC            90
Gly Gly Asp Gly Gln Ala Gly Pro Asp Glu Gly Glu Val Asp
            20                  25                  30
```

(2) INFORMATION FOR SEQ ID NO: 35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...18

(xi) SEQUENCE DESCRIPTION: SEQ ID NO: 35:

```
GAC GAG GGC GAG GTG GAC                                        18
Asp Glu Gly Glu Val Asp
 1               5
```

(2) INFORMATION FOR SEQ ID NO: 36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...48

(xi) SEQUENCE DESCRIPTION: SEQ ID NO: 36:

```
GAG GAG GAG GAG GAG GAG GAG GAA GAC GAC GAG GAC GAC GAC GAC GAC      48
Glu Glu Glu Glu Glu Glu Glu Glu Asp Asp Glu Asp Asp Asp Asp Asp
 1               5                  10                  15
```

(2) INFORMATION FOR SEQ ID NO: 37:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...84

(xi) SEQUENCE DESCRIPTION: SEQ ID NO: 37:

```
GAG GAG GAG GAG GAG GAG GAG GAA GAC GAC GAG GAC GAC GAC GAC GAC      48
Glu Glu Glu Glu Glu Glu Glu Glu Asp Asp Glu Asp Asp Asp Asp Asp
 1               5                  10                  15

GTC GTG TCC GAG GGC TCG GAG GTG CCC GAG AGC GAT                      84
Val Val Ser Glu Gly Ser Glu Val Pro Glu Ser Asp
                 20                  25
```

(2) INFORMATION FOR SEQ ID NO: 38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...36

(xi) SEQUENCE DESCRIPTION: SEQ ID NO: 38:

```
GTC GTG TCC GAG GGC TCG GAG GTG CCC GAG AGC GAT                      36
Val Val Ser Glu Gly Ser Glu Val Pro Glu Ser Asp
 1               5                  10
```

(2) INFORMATION FOR SEQ ID NO: 39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...30

(xi) SEQUENCE DESCRIPTION: SEQ ID NO: 39:

```
CCC CCC GGG AAG CCA GCC CTC CCA GGA GCC                              30
Pro Pro Gly Lys Pro Ala Leu Pro Gly Ala
 1               5                  10
```

(2) INFORMATION FOR SEQ ID NO: 40:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...45

-continued

```
    (xi) SEQUENCE DESCRIPTION: SEQ ID NO: 40:

GAG GAT GGG GTC CAG GGT GAG CCC CCT GAA CCT GAA GAT GCA GAG           45
Glu Asp Gly Val Gln Gly Glu Pro Pro Glu Pro Glu Asp Ala Glu
 1               5                  10                  15

(2) INFORMATION FOR SEQ ID NO: 41:

(i) SEQUENCE CHARACTERISTICS:
         (A) LENGTH: 7 amino acids
         (B) TYPE: amino acid
         (D) TOPOLOGY: linear (ii) MOLECULE TYPE: protein (xi) SEQUENCE DESCRIPTION: SEQ ID NO: 41:

Arg Asp Val Ser Glu Glu Leu
 1               5

(2) INFORMATION FOR SEQ ID NO: 42:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ix) FEATURE:
         (A) NAME/KEY: Coding Sequence
         (B) LOCATION: 1...21

(xi) SEQUENCE DESCRIPTION: SEQ ID NO: 42:

CGT GAT GTC TCT GAG GAG CTG                                            21
Arg Asp Val Ser Glu Glu Leu
 1               5
```

LOW DENSITY LIPOPROTEIN BINDING PROTEINS AND THEIR USE IN DIAGNOSING AND TREATING ATHEROSCLEROSIS

FIELD OF THE INVENTION

This application is a continuation-in-part of U.S. Ser. No. 08/979,608, filed Nov. 26, 1997 now U.S. Pat. No. 6,355,451, which claimed priority from U.S. Ser. No. 60/031,930, filed Nov. 27, 1996, and U.S. Ser. No. 60/048,547, filed Jun. 3, 1997. This invention relates to novel polypeptides (LBPs) which bind to low density lipoprotein (LDL), polynucleotides which encode these polypeptides, and treatments, diagnoses and therapeutic agents for atherosclerosis.

BACKGROUND OF THE INVENTION

Atherosclerosis is the principal cause of heart attacks and strokes. It has been reported that about 50% of all deaths in the United States, Europe and Japan are due to atherosclerosis. Atherosclerotic lesions in the arterial wall characterize atherosclerosis. Cholesteryl esters (CE) are present in these atherosclerotic lesions. Low density lipoprotein (LDL) has been shown to be the major carrier of plasma CE, and has been implicated as the agent by which CE enter the atherosclerotic lesions.

Scattered groups of lipid-filled macrophages, called foam cells, are the first visible signs of atherosclerosis and are described as type I lesions. These macrophages are reported to contain CE derived from LDL. The macrophages recognize oxidized LDL, but not native LDL, and become foam cells by phagocytosing oxidized LDL. Larger, more organized collections of foam cells, fatty streaks, represent type II lesions. These lesions further develop into complex lesions called plaques, which can result in impeding the flow of blood in the artery.

It is widely believed that accumulation of LDL in the artery depends on the presence of functionally modified endothelial cells in the arterial wall. It has been reported in animal models of atherosclerosis that LDL, both native LDL and methylated LDL, accumulates focally and irreversibly only at the edges of regenerating endothelial islands in aortic lesions, where functionally modified endothelial cells are present, but not in the centers of these islands where endothelial regeneration is completed. Similarly, LDL accumulates in human atherosclerotic lesions. The mechanism by which the LDL accumulates focally and irreversibly in arterial lesions has not heretofore been understood.

SUMMARY OF THE INVENTION

It is an object of the invention to provide polypeptides which bind to LDL.

It is yet another object of the invention to provide a method for determining if an animal is at risk for atherosclerosis.

It is yet another object of the invention to provide a method for evaluating an agent for use in treating atherosclerosis.

It is yet another object of the invention to provide a method for treating atherosclerosis.

Still another object of the invention is to utilize an LBP (low density lipoprotein binding protein) gene and/or polypeptide, or fragments, analogs and variants thereof, to aid in the treatment, diagnosis and/or identification of therapeutic agents for atherosclerosis.

In one aspect, the invention features an isolated polynucleotide comprising a polynucleotide encoding the polypeptide comprising the amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9; or a polynucleotide capable of hybridizing to and which is at least about 95% identical to any of the above polynucleotides and wherein the encoded polypeptide is capable of binding to LDL; or a biologically active fragment of any of the above polynucleotides wherein the encoded polypeptide is capable of binding to LDL.

In certain embodiments, the polynucleotide comprises the nucleic acid sequence as set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:18.

Another aspect of the invention is an isolated polypeptide comprising a polypeptide having the amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9; or a polypeptide which is at least about 95% identical to any of the above polypeptides and wherein the polypeptide is capable of binding to LDL; or a biologically active fragment of any of the above polypeptides wherein the fragment is capable of binding to LDL.

Another aspect of the invention is a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis.

Another aspect of the invention is a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

Another aspect of the invention is a method for evaluating an agent for the ability to alter the binding of LBP polypeptide to a binding molecule, e.g., native LDL, modified LDL, e.g., methylated LDL or oxidized LDL, or an arterial extracellular matrix structural component. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

Another aspect of the invention is a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated.

Another aspect of the invention is a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated.

Another aspect of the invention is a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs. In certain embodiments, the agent is an LBP polypeptide, e.g., LBP-1, LBP-2 or LBP-3, or a biologically active fragment or analog thereof. In certain embodiments, the agent is a polypeptide of no more than about 100, 50, 30, 20, 10, 5, 4, 3 or 2 amino acid residues in length. In certain embodiments, the agent is a polypeptide having an amino acid sequence that includes at least about 20%, 40%, 60%, 8%, 90%, 95% or 98% acidic amino acid residues.

Another aspect of the invention is a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs.

Another aspect of the invention is a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

Another aspect of the invention is a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a method for diagnosing atherosclerotic lesions in an animal. An animal is provided. A labeled agent capable of binding to LBP, e.g., LBP-1, LBP-2 or LBP-3, present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Another aspect of the invention is a method for immunizing an animal against an LBP, e.g., LBP-1, LBP-2 or LBP-3, or fragment or analog thereof. An animal having LDL is provided. The LBP or fragment or analog thereof is administered to the animal so as to stimulate antibody production by the animal to the LBP or fragment or analog thereof such that binding of the LBP to the LDL is altered, e.g., decreased or increased.

Another aspect of the invention is a method of making a fragment or analog of LBP polypeptide, the fragment or analog having the ability to bind to native LDL and to modified LDL, e.g., methylated LDL, oxidized LDL, acetylated LDL, or cyclohexanedione-treated LDL. An LBP polypeptide is provided. The sequence of the LBP polypeptide is altered. The altered LBP polypeptide is tested for the ability to bind to modified LDL and native LDL.

Yet another aspect of the invention is a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes the polypeptide is isolated, the cDNA encoding an LBP.

The above and other features, objects and advantages of the present invention will be better understood by a reading of the following specification in conjunction with the drawings.

BRIEF DESCRIPTION OF THE DRAWINGS

FIG. 1 depicts the amino acid sequence of rabbit LBP-1 (SEQ ID NO:1). Differences in amino acids between rabbit and human LBP-1 are depicted in bold type.

FIG. 2 depicts the amino acid sequence of rabbit LBP-2 (SEQ ID NO:2). Differences in amino acids between rabbit and human LBP-2 are depicted in bold type.

FIG. 3 depicts the amino acid sequence of amino acids 86 to 317 of rabbit LBP-2 (SEQ ID NO:3).

FIG. 4 depicts the amino acid sequence of amino acids 66 to 317 of rabbit LBP-2 (SEQ ID NO:4).

FIGS. 5A–5B depict the amino acid sequence of rabbit LBP-3 (SEQ ID NO:5). Differences in amino acids between rabbit and human LBP-3 are depicted in bold type.

FIG. 6 depicts the amino acid sequence of human LBP-1 (SEQ ID NO:6). Differences in amino acids between rabbit and human LBP-1 are depicted in bold type.

FIG. 7 depicts the amino acid sequence of human LBP-2 (SEQ ID NO:7). Differences in amino acids between rabbit and human LBP-2 are depicted in bold type.

FIGS. 8A–8B depict the amino acid sequence of human LBP-3 (SEQ ID NO:8). Differences in amino acids between rabbit and human LBP-3 are depicted in bold type.

FIG. 9 depicts the amino acid sequence of amino acids 14 to 33 of human or rabbit LBP-1, called BHF-1 (SEQ ID NO:9).

FIGS. 10A–10A depict the cDNA sequence encoding rabbit LBP-1 (SEQ ID NO:10) and the corresponding amino acid sequence. Differences in amino acids between rabbit and human LBP-1 are depicted in bold type.

FIGS. 11A–11C depict the cDNA sequence encoding rabbit LBP-2 (SEQ ID NO:11) and the corresponding amino acid sequence. Differences in amino acids between rabbit and human LBP-2 are depicted in bold type.

FIGS. 12A–12B depict the cDNA sequence 256 to 1617 of rabbit LBP-2 (SEQ ID NO:12) and the corresponding amino acid sequence.

FIGS. 13A–13B depict the cDNA sequence 196 to 1617 of rabbit LBP-2 (SEQ ID NO:13) and the corresponding amino acid sequence.

FIGS. 14A–14F depict the cDNA sequence encoding rabbit LBP-3 (SEQ ID NO:14) and the corresponding amino acid sequence. Differences in amino acids between rabbit and human LBP-3 are depicted in bold type.

FIGS. 15A–15B depict the cDNA sequence encoding human LBP-1 (SEQ ID NO:15) and the corresponding amino acid sequence. Differences in amino acids between rabbit and human LBP-1 are depicted in bold type.

FIGS. 16A–16B depict the cDNA sequence encoding human LBP-2 (SEQ ID NO:16) and the corresponding amino acid sequence. Differences in amino acids between rabbit and human LBP-2 are depicted in bold type.

FIGS. 17A–17D depict the cDNA sequence encoding human LBP-3 (SEQ ID NO:17) and the corresponding amino acid sequence. Differences in amino acids between rabbit and human LBP-3 are depicted in bold type.

FIG. 18 depicts the cDNA sequence encoding BHF-1 (SEQ ID NO:18).

FIG. 19 corresponds to the amino acid sequence of rabbit LBP-1 (top sequence) in alignment with the amino acid sequence of human LBP-1 (bottom sequence).

FIG. 20 corresponds to the amino acid sequence of rabbit LBP-2 (top sequence) in alignment with the amino acid sequence of human LBP-2 (bottom sequence).

FIG. 21 corresponds to the amino acid sequence of rabbit LBP-3 (top sequence) in alignment with the amino acid sequence of human LBP-3 (bottom sequence).

DETAILED DESCRIPTION

In accordance with aspects of the present invention, there are provided novel mature human and rabbit polypeptides, LBP-1, LBP-2 and LBP-3, and biologically active analogs and fragments thereof, and there are provided isolated polynucleotides which encode such polypeptides. LBP is an abbreviation for low density lipoprotein (LDL) binding protein. The terms polynucleotide, nucleotide and oligonucleotide are used interchangeably herein, and the terms polypeptides, proteins and peptides are used interchangeably herein.

This invention provides for an isolated polynucleotide comprising a polynucleotide encoding the polypeptide having the amino acid sequence of rabbit LBP-1 as set forth in FIG. 1 (SEQ ID NO:1); rabbit LBP-2 as set forth in FIG. 2 (SEQ ID NO:2); 86 to 317 of rabbit LBP-2 as set forth in FIG. 3 (SEQ ID NO:3); 66 to 317 of rabbit LBP-2 as set forth in FIG. 4 (SEQ ID NO:4); rabbit LBP-3 as set forth in FIG. 5 (SEQ ID NO:5); human LBP-1 as set forth in FIG. 6 (SEQ ID NO:6); human LBP-2 as set forth in FIG. 7 (SEQ ID NO:7); human LBP-3 as set forth in FIG. 8 (SEQ ID NO:8); 14 to 33 of human or rabbit LBP-1, called BHF-1, as set forth in FIG. 9 (SEQ ID NO:9); a polynucleotide capable of hybridizing to and which is at least about 80% identical, more preferably at least about 90% identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

This invention also includes an isolated polynucleotide comprising a polynucleotide encoding the polypeptide having amino acid residues 8–22 (SEQ ID NO:19), 8–33 (SEQ ID NO:20), 23–33 (SEQ ID NO:21) or 208–217 (SEQ ID NO:22) of human LBP-2 as set forth in FIG. 7 (SEQ ID NO:7); amino acid residues 14–43 (SEQ ID NO:23) or 38–43 (SEQ ID NO:24) of rabbit or human LBP-1 as set. forth in FIG. 1 (SEQ ID NO:1) and FIG. 6 (SEQ ID NO:6); amino acid residues 105–120 (SEQ ID NO:25), 105–132 (SEQ ID NO:26), 121–132 (SEQ ID NO:27) or 211–220 (SEQ ID NO:28) of rabbit LBP-2 as set forth in FIG. 2 (SEQ ID NO:2); amino acid residues 96–110 (SEQ ID NO:29) of rabbit LBP-3 as set forth in FIG. 5 (SEQ ID NO:5); amino acid residues 53–59 (SEQ ID NO:41) of human LBP-3 as set forth in FIG. 8 (SEQ ID NO:8); a polynucleotide capable of hybridizing to and which is at least about 80% identical, more preferably at least about 90° C. identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

By a polynucleotide encoding a polypeptide is meant a polynucleotide which includes only coding sequence for the polypeptide, as well as a polynucleotide which includes additional coding and/or non-coding sequences. Thus, e.g., the polynucleotides which encode for the mature polypeptides of FIGS. 1–9 (SEQ ID NOS:1–9) may include only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequences 5' and/or 3' of the coding sequence for the mature polypeptide. The polynucleotides of the invention are also meant to include polynucleotides in which the coding sequence for the mature polypeptide is fused in the same reading frame to a polynucleotide sequence which aids in expression and/or secretion of a polypeptide from a host cell, e.g., a leader sequence. The polynucleotides are also meant to include polynucleotides in which the coding sequence is fused in frame to a marker sequence which, e.g., allows for purification of the polypeptide.

The polynucleotides of the present invention may be in the form of RNA, DNA or PNA, e.g., cRNA, cDNA, genomic DNA, or synthetic DNA, RNA or PNA. The DNA may be double-stranded or single stranded, and if single stranded may be the coding strand or non-coding (antisense) strand.

In preferred embodiments, the polynucleotide comprises the nucleic acid of rabbit LBP-1 as set forth in FIG. 10 (SEQ ID NO:10); rabbit LBP-2 as set forth in FIG. 11 (SEQ ID NO:11); nucleotide 256 to 1617 of rabbit LBP-2 as set forth in FIG. 12 (SEQ ID NO:12); nucleotide 196 to 1617 of rabbit LBP-2 as set forth in FIG. 13 (SEQ ID NO:13); rabbit LBP-3 as set forth in FIG. 14 (SEQ ID NO:14); human LBP-1 as set forth in FIG. 15 (SEQ ID NO:15); human LBP-2 as set forth in FIG. 16 (SEQ ID NO:16); human LBP-3 as set forth in FIG. 17 (SEQ ID NO:17); or nucleotide 97 to 156 of rabbit LBP-1 or nucleotide 157 to 216 of human LBP-1, (BHF-1), as set forth in FIG. 18 (SEQ ID NO:18).

In other preferred embodiments, the polynucleotide comprises the nucleic acid as set forth in SEQ ID NO:30, SEQ ID NO:31, SEQ ID NO:32, SEQ ID NO:33 SEQ ID NO:34, SEQ ID NO:35, SEQ ID NO:36, SEQ ID NO:37, SEQ ID NO:38, SEQ ID NO:39, SEQ ID NO:40 or SEQ ID NO:42.

The coding sequence which encodes the mature polypeptide may be identical to the coding sequences shown in FIGS. 10–18 (SEQ ID NOS:10–18) or SEQ ID NOS:30–40 or 42, or may be a different coding sequence which coding sequence, as a result of the redundancy or degeneracy of the genetic code, encodes the same mature polypeptides as the DNA of FIGS. 10–18 (SEQ ID NOS:10–18) and SEQ ID NOS: 30–40 and 42.

This invention also includes recombinant vectors comprising the polynucleotides described above. The vector can be, e.g., a plasmid, a viral particle or a phage. In certain embodiments, the recombinant vector is an expression vector. The vectors may also include various marker genes which are useful in identifying cells containing such vectors.

This invention also includes a cell comprising such a recombinant vector. The recombinant vectors described herein can be introduced into a host cell, e.g., by transformation, transfection or infection.

This invention also includes a method for producing an LBP comprising culturing such a cell under conditions that permit expression of the LBP.

This invention also includes an isolated polypeptide comprising a polypeptide having the amino acid sequence as set forth in FIG. 1 (SEQ ID NO:1); FIG. 2 (SEQ ID NO:2); FIG. 3 (SEQ ID NO:3); FIG. 4 (SEQ ID.NO:4); FIG. 5 (SEQ ID NO:5); FIG. 6 (SEQ ID NO:6); FIG. 7 (SEQ ID NO:7); FIG. 8 (SEQ ID NO:8) or FIG. 9 (SEQ ID NO:9); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL. Differences in amino acids between the rabbit and human LBP-1, LBP-2 and LBP-3 genes are depicted in bold type in the figures. The differences in the amino acid sequences between rabbit and human LBP-1, LBP-2 and LBP-3 are also specifically shown in FIGS. 19, 20 and 21, respectively.

This invention also includes an isolated polypeptide comprising a polypeptide having amino acid residues 8–22 (SEQ ID NO:19), 8–33 (SEQ ID NO:20), 23–33 (SEQ ID NO:21) or 208–217 (SEQ ID NO:22) as set forth in FIG. 7 (SEQ ID NO:7); amino acid residues 14–43 (SEQ ID NO:23) or 38–43 (SEQ ID NO:24) as set forth in FIG. 1 (SEQ ID NO:1) and FIG. 6 (SEQ ID NO:6); amino acid residues 105–120 (SEQ ID NO:25), 105–132 (SEQ ID NO:26), 121–132 (SEQ ID NO:27) or 211–220 (SEQ ID NO:28) as set forth in FIG. 2 (SEQ ID NO:2); amino acid residues 96–110 (SEQ ID NO:29) as set forth in FIG. 5 (SEQ ID NO:5); and amino acid residues 53–59 (SEQ ID NO:41) as set forth in FIG. 8 (SEQ ID NO:8); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL.

The polypeptides of the invention are meant to include, e.g., a naturally purified product, a chemically synthesized product, and a recombinantly derived product.

The polypeptides can be used, e.g., to bind to LDL, thereby inhibiting formation of atherosclerotic plaques. The polypeptides can also be used, e.g., in gene therapy, by expression of such polypeptides in vivo. The polypeptides can also be used in pharmaceutical or vaccine compositions. The polypeptides can also be used as immunogens to produce antibodies thereto, which in turn, can be used as antagonists to the LBP polypeptides.

Without being bound by any theory, it is believed that the LBPs provide the mechanism by which atherosclerosis is promoted through LDL oxidation. The LBPs are believed to be required in order for focal, irreversible LDL binding to occur at the arterial wall, and that such binding is a critical early event in atherosclerosis because it allows the time necessary for LDL to be changed from its native state to a fully oxidized state. Since oxidized, but not native, LDL is a foreign protein, macrophages ingest it, first becoming the foam cells of type I lesions, and subsequently forming the fatty streaks of type II lesions.

This invention also includes a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis.

By atherosclerosis is meant a disease or condition which comprises several stages which blend imperceptibly into each other, including irreversible binding of LDL, LDL oxidation, macrophage recruitment, blockage of the artery and tissue death (infarction).

By animal is meant human as well as non-human animals. Non-human animals include, e.g., mammals, birds, reptiles, amphibians, fish, insects and protozoa. Preferably, the non-human animal is a mammal, e.g., a rabbit, a rodent, e.g., a mouse, rat or guinea pig, a primate, e.g., a monkey, or a pig. An animal also includes transgenic non-human animals. The term transgenic animal is meant to include an animal that has gained new genetic information from the introduction of foreign DNA, i.e., partly or entirely heterologous DNA, into the DNA of its cells; or introduction of a lesion, e.g., an in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout or replacement of the homologous host gene or results in altered-and/or regulatable expression and/or metabolism of the gene. The animal may include a transgene in all of its cells including germ line cells, or in only one or some of its cells. Transgenic animals of the invention can serve as a model for studying atherosclerosis or for evaluating agents to treat atherosclerosis.

In certain embodiments, the determination for being at risk for atherosclerosis is done in a prenatal animal.

By LBP is meant a low density lipoprotein (LDL) binding protein which is capable of binding LDL and methylated LDL. By methylated LDL is meant that about 50% to about 90% of the lysine residues of LDL have a methyl group chemically attached. Methylated LDL is not recognized by previously reported cell surface receptors. See, e.g., Weisgraber et al., J. Biol. Chem. 253:9053–9062 (1978). In certain embodiments, the. LBP is also capable of binding oxidized LDL. In certain preferred embodiments, the binding of LDL to an LBP is irreversible. In certain preferred embodiments, the LBP does not transport the LDL to any intracellular compartment. Examples of LBPs are LBP-1, LBP-2 and LBP-3 described herein.

By LBP metabolism is meant any aspect of the production, release, expression, function, action, interaction or regulation of LBP. The metabolism of LBP includes modifications, e.g., covalent or non-covalent modifications, of LBP polypeptide. The metabolism of LBP includes modifications, e.g., covalent or non-covalent modifications, that LBP induces in other substances. The metabolism of LBP also includes changes in the distribution of LBP polypeptide, and changes LBP induces in the distribution of other substances.

Any aspect of LBP metabolism can be evaluated. The methods used are standard techniques known to those skilled in the art and can be found in standard references, e.g., Ausubel et al., ed., Current Protocols in Mol. Biology, New York: John Wiley & Sons, 1990; Kriegler, M., ed., Gene Transfer and Expression, Stockton Press, New York, N.Y., 1989; pDisplay gene expression system (Invitrogen, Carlsbad, Calif.). Preferred examples of LBP metabolism that can be evaluated include the binding activity of LBP polypeptide to a binding molecule, e.g., LDL; the transactivation activity of LBP polypeptide on a target gene; the level of LBP protein; the level of LBP mRNA; the level of LBP modifications, e.g., phosphorylation, glycosylation or acylation; or the effect of LBP expression on transfected mammalian cell binding of LDL.

By binding molecule is meant any molecule to which LBP can bind, e.g., a nucleic acid, e.g., a DNA regulatory region, a protein, e.g., LDL, a metabolite, a peptide mimetic, a non-peptide mimetic, an antibody, or any other type of ligand. In certain preferred embodiments, the aspect of LBP metabolism that is evaluated is the ability of LBP to bind to native LDL and/or methylated LDL and/or oxidized LDL. Binding to LDL can be shown, e.g., by antibodies against LDL, affinity chromatography, affinity coelectrophoresis (ACE) assays, or ELISA assays. See Examples. In other embodiments, it is the ability of LBP to bind to an arterial extracellular matrix stuctural component that is evaluated. Examples of such components include proteoglycans, e.g., chondroitin sulfate proteoglycans and heparin sulfate proteoglycans; elastin; collagen; fibronectin; vitronectin; integrins; and related extracellular matrix molecules. Binding to arterial extracellular matrix structural components can be shown by standard methods known to those skilled in the art, e.g., by ELISA assays. Primary antibodies to the LBP are then added, followed by an enzyme-conjugated secondary antibody to the primary antibody, which produces a stable color in the presence of an appropriate substrate, and color development on the plates is measured in a microtiter plate reader.

Transactivation of a target gene by LBP can be determined, e.g., in a transient transfection assay in which the promoter of the target gene is linked to a reporter gene, e.g., β-galacto-sidase or luciferase, and co-transfected with an LBP expression vector. Such evaluations can be done in vitro or in vivo. Levels of LBP protein, mRNA or phosphorylation, can be measured, e.g., in a sample, e.g., a tissue sample, e.g., arterial wall, by standard methods known to those skilled in the art.

In certain embodiments, an aspect of LBP structure is evaluated, e.g., LBP gene structure or LBP protein structure. For example, primary, secondary or tertiary structures can be evaluated. For example, the DNA sequence of the gene is determined and/or the amino acid sequence of the protein is determined. Standard cloning and sequencing methods can be used as are known to those skilled in the art. In certain embodiments, the binding activity of an antisense nucleic acid with the cellular LBP mRNA and/or genomic DNA is determined using standard methods known to those skilled in the art so as to detect the presence or absence of the target mRNA or DNA sequences to which the antisense nucleic acid would normally specifically bind.

The risk for atherosclerosis that is determined can be a reduced risk or an increased risk as compared to a normal animal. For example, an abnormality which would give a reduced risk is an inactive LBP polypeptide. An abnormality which would give an increased risk would be, e.g., an LBP polypeptide that has higher activity, e.g., LDL binding activity, than native LBP polypeptide.

The invention also includes a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

In certain embodiments, the method employs two phases for evaluating an agent for use in treating atherosclerosis, an initial in vitro phase and then an in vivo phase. The agent is administered to the test cell or cell-free system in vitro, and if a change in an aspect of LBP metabolism occurs, then the agent is further administered to a test animal in a therapeutically effective amount and evaluated in vivo for an effect of the agent on an aspect of LBP metabolism.

By cell is meant a cell or a group of cells, or a cell that is part of an animal. The cell can be a human or non-human cell. Cell is also meant to include a transgenic cell. The cell can be obtained, e.g., from a culture or from an animal. Animals are meant to include, e.g., natural animals and non-human transgenic animals. In certain embodiments, the transgenic cell or non-human transgenic animal has an LBP transgene, or fragment or analog thereof. In certain embodiments, the transgenic cell or non-human transgenic animal has a knockout for the LBP gene.

The test cell, cell-free system or animal can have a wild type pattern or a non-wild type pattern of LBP metabolism. A non-wild type pattern of LBP metabolism can result, e.g., from under-expression, over-expression, no expression, or a temporal, site or distribution change. Such a non-wild type pattern can result, e.g., from one or more mutations in the LBP gene, in a binding molecule gene, a regulatory gene, or in any other gene which directly or indirectly affects LBP metabolism. A mutation is meant to include, e.g., an alteration, e.g., in gross or fine structure, in a nucleic acid. Examples include single base pair alterations, e.g., missense or nonsense mutations, frameshifts, deletions, insertions and translocations. Mutations can be dominant or recessive. Mutations can be homozygous or heterozygous. Preferably, an aspect of LBP-1, LBP-2 or LBP-3 metabolism is evaluated.

An agent is meant to include, e.g., any substance, e.g., an anti-atherosclerosis drug. The agent of this invention preferably can change an aspect of LBP metabolism. Such change can be the result of any of a variety of events, including, e.g., preventing or reducing interaction between LBP and a binding molecule, e.g., LDL or an arterial extracellular matrix structural component; inactivating LBP and/or the binding molecule, e.g., by cleavage or other modification; altering the affinity of LBP and the binding molecule for each other; diluting out LBP and/or the binding molecule; preventing expression of LBP and/or the binding molecule; reducing synthesis of LBP and/or the binding molecule; synthesizing an abnormal LBP and/or binding molecule; synthesizing an alternatively spliced LBP and/or binding molecule; preventing or reducing proper conformational folding of LBP and/or the binding molecule; modulating the binding properties of LBP and/or the binding molecule; interfering with signals that are required to activate or deactivate LBP and/or the binding molecule; activating or deactivating LBP and/or the binding molecule in such a way as to prevent binding; or interfering with other receptors, ligands or other molecules which are required for the normal synthesis or functioning of LBP and/or the binding molecule. For example, the agent can block the binding site on LDL for LBPs expressed focally in the arterial wall extracellular matrix, or it could block the binding site on an LBP for LDL, or it could be bifunctional, i.e., it could block both binding sites.

Examples of agents include LBP polypeptide, e.g., LBP-1, LBP-2 or LBP-3, or a biologically active fragment or analog thereof; a nucleic acid encoding. LBP polypeptide or a biologically active fragment or analog thereof; a nucleic acid encoding an LBP regulatory sequence or a biologically active fragment or analog thereof; a binding molecule for LBP polypeptide; a binding molecule for LBP nucleic acid, the LBP nucleic acid being, e.g., a nucleic acid comprising a regulatory region for LBP or a nucleic acid comprising a structural region for LBP or a biologically active fragment of LBP; an antisense nucleic acid; a mimetic of LBP or a binding molecule; an antibody for LBP or a binding molecule; a metabolite; or an inhibitory carbohydrate or glycoprotein. In certain embodiments, the agent is an antagonist, agonist or super agonist.

Knowledge of the existence of the sequence of the LBPs allows a search for natural or artificial ligands to regulate LDL levels in the treatment of atherosclerosis. In certain embodiments, the agent is a natural ligand for LBP. In certain embodiments, the agent is an artificial ligand for LBP.

By analog is meant a compound that differs from naturally occurring LBP in amino acid sequence or in ways that do not involve sequence, or both. Analogs of the invention generally exhibit at least about 80% homology, preferably at least about 90% homology, more preferably yet at least about 95% homology, and most preferably at least about 98% homology, with substantially the entire sequence of a naturally occurring LBP sequence, preferably with a segment of about 100 amino acid residues, more preferably with a segment of about 50 amino acid residues, more preferably yet with a segment of about 30 amino acid residues, more preferably yet with a segment of about 20 amino acid residues, more preferably yet with a segment of about 10 amino acid residues, more preferably yet with a segment of about 5 amino acid residues, more preferably yet with a segment of about 4 amino acid residues, more preferably yet with a segment of about 3 amino acid residues, and most preferably with a segment of about 2 amino acid residues. Non-sequence modifications include, e.g., in vivo or in vitro chemical derivatizations of LBP. Non-sequence modifications include, e.g., changes in phosphorylation, acetylation, methylation, carboxylation, or glycosylation. Methods for making such modifications are known to those skilled in the art. For example, phosphorylation can be modified by exposing LBP to phosphorylation-altering enzymes, e.g., kinases or phosphatases.

Preferred analogs include LBP or biologically active fragments thereof whose sequences differ from the wild-type sequence by one or more conservative amino acid substitutions or by one or more non-conservative amino acid substitutions, deletions, or insertions which do not abolish LBP biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other examples of conservative substitutions are shown in Table 1.

TABLE 1

CONSERVATIVE AMINO ACID SUBSTITUTIONS

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn, L-NMMA, L-NAME |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |

TABLE 1-continued

CONSERVATIVE AMINO ACID SUBSTITUTIONS

| For Amino Acid | Code | Replace with any of |
| --- | --- | --- |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His |
| Valine | V | D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., Bio-Technique 1:11–15 (1989)), or saturation mutagenesis (by, e.g., chemical treatment or irradiation of single-stranded DNA in vitro, and synthesis of a complementary DNA strand; Mayers et al., Science 229:242 (1985)). Random mutagenesis can also be accomplished by, e.g., degenerate oligonucleotide generation (using, e.g., an automatic DNA synthesizer to chemically synthesize degenerate sequences; Narang, Tetrahedron 39:3 (1983); Itakura et al., Recombinant DNA, Proc. 3rd Cleveland Sympos. Macromolecules, ed. A. G. Walton, Amsterdam: Elsevier, pp. 273–289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above. For example, analogs can be made by in vitro DNA sequence modifications of the sequences of FIGS. 10–18 (SEQ ID NOS:10–18). For example, in vitro mutagenesis can be used to convert any of these DNA sequences into a sequence which encodes an analog in which one or more amino acid residues has undergone a replacement, e.g., a conservative replacement as described in Table 1.

Methods for identifying desirable mutations include, e.g., alanine scanning mutagenesis (Cunningham and Wells, Science 244:1081–1085 (1989)), oligonucleotide-mediated mutagenesis (Adelman et al., DNA 2:183 (1983)); cassette mutagenesis (Wells et al., Gene 34:315 (1985)), combinatorial mutagenesis, and phage display libraries (Ladner et al., PCT International Appln. No. WO88/06630). The LBP analogs can be tested, e.g., for their ability to bind to LDL and/or to an arterial extracellular matrix component, as described herein.

Other analogs within the invention include, e.g., those with modifications which increase peptide stability. Such analogs may contain, e.g., one or more non-peptide bonds (which replace the peptide bonds) in the peptide sequence. Also included are, e.g.: analogs that include residues other than naturally occurring L-amino acids, e.g., D-amino acids or non-naturally occurring or synthetic amino acids, e.g., β or γ amino acids; and cyclic analogs.

Analogs are also meant to include peptides in which structural modifications have been introduced into the peptide backbone so as to make the peptide non-hydrolyzable. Such peptides are particularly useful for oral administration, as they are not digested. Peptide backbone modifications include, e.g., modifications of the amide nitrogen, the α-carbon, the amide carbonyl, or the amide bond, and modifications involving extensions, deletions or backbone crosslinks. For example, the backbone can be modified by substitution of a sulfoxide for the carbonyl, by reversing the peptide bond, or by substituting a methylene for the carbonyl group. Such modifications can be made by standard procedures known to those skilled in the art. See, e.g., Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267–357, B. Weinstein (ed.), Marcel Dekker, Inc., New York (1983).

An analog is also meant to include polypeptides in which one or more of the amino acid residues include a substituent group, or polypeptides which are fused with another compound, e.g., a compound to increase the half-life of the polypeptide, e.g., polyethylene glycol.

By fragment is meant some portion of the naturally occurring LBP polypeptide. Preferably, the fragment is at least about 100 amino acid residues, more preferably at least about 50 amino acid residues, more preferably yet at least about 30 amino acid residues, more preferably yet at least about 20 amino acid residues, more preferably yet at least about 5 amino acid residues, more preferably yet at least about 4 amino acid residues, more preferably yet at least about 3 amino acid residues, and most preferably at least about 2 amino acid residues in length. Fragments include, e.g., truncated secreted forms, proteolytic fragments, splicing fragments, other fragments, and chimeric constructs between at least a portion of the relevant gene, e.g., LBP-1, LBP-2 or LBP-3, and another molecule. Fragments of LBP can be generated by methods known to those skilled in the art. In certain embodiments, the fragment is biologically active. The ability of a candidate fragment to exhibit a biological activity of LBP can be assessed by methods known to those skilled in the art. For example, LBP fragments can be tested for their ability to bind to LDL and/or to an arterial extracellular matrix structural component, as described herein. Also included are LBP fragments containing residues that are not required for biological activity of the fragment or that result from alternative mRNA splicing or alternative protein processing events.

Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated, e.g., by random shearing, restriction digestion or a combination of the above-discussed methods. For example, fragments of LBP can be made by expressing LBP DNA which has been manipulated in vitro to encode the desired fragment, e.g., by restriction digestion of any of the DNA sequences of FIGS. 10–18 (SEQ ID NOS:10–18).

Fragments can also be chemically synthesized using techniques known in the art, e.g., conventional Merrifield solid phase f-Moc or t-Boc chemistry. For example, peptides of the present invention can be arbitrarily divided into fragments of desired length with no overlap of the fragments, or divided into overlapping fragments of a desired length.

An LBP or a biologically active fragment or analog thereof, or a binding molecule or a biologically active fragment or analog thereof, can, e.g., compete with its cognate molecule for the binding site on the complementary molecule, and thereby reduce or eliminate binding between LBP and the cellular binding molecule. LBP or a binding molecule can be obtained, e.g., from purification or secretion of naturally occurring LBP or binding molecule, from recombinant LBP or binding molecule, or from synthesized LBP or binding molecule.

Therefore, methods for generating analogs and fragments and testing them for activity are known to those skilled in the art.

An agent can also be a nucleic acid used as an antisense molecule. Antisense therapy is meant to include, e.g., administration or in situ generation of oligonucleotides or their derivatives which specifically hybridize, e.g., bind, under cellular conditions, with the cellular mRNA and/or genomic DNA encoding an LBP polypeptide, or mutant thereof, so as to inhibit expression of the encoded protein, e.g., by inhibiting transcription and/or translation. The binding may be by conventional base pair complementarity, or, for example, in the case of binding to DNA-duplexes, through specific interactions in the major groove of the double helix.

In certain embodiments, the antisense construct binds to a naturally-occurring sequence of an LBP gene which, e.g., is involved in expression of the.gene. These sequences include, e.g., promoter, start codons, stop codons, and RNA polymerase binding sites.

In other embodiments, the antisense construct binds to a nucleotide sequence which is not present in the wild type gene. For example, the antisense construct can bind to a region of an LBP gene which contains an insertion of an exogenous, non-wild type sequence. Alternatively, the antisense construct can bind to a region of an LBP gene which has undergone a deletion, thereby bringing two regions of the gene together which are not normally positioned together and which, together, create a non-wild type sequence. When administered in vivo to a subject, antisense constructs which bind to non-wild type sequences provide the advantage of inhibiting the expression of a mutant LBP gene, without inhibiting expression of any wild type LBP gene.

An antisense construct of the present invention can be delivered, e.g., as an expression plasmid which, when transcribed in the cell, produces RNA which is complementary to at least a unique portion of the cellular mRNA which encodes an LBP polypeptide. An alternative is that the antisense construct is an oligonucleotide which is generated ex vivo and which, when introduced into the cell causes inhibition of expression by hybridizing with the mRNA (duplexing) and/or genomic sequences (triplexing) of an LBP gene. Such oligonucleotides are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate, phosphorodithioates and methylphosphonate analogs of DNA and peptide nucleic acids (PNA). (See also U.S. Pat. Nos. 5,176,996; 5,264,564; and 5,256,775). Additionally, general approaches to constructing oligomers useful in antisense therapy have been reviewed. (See, e.g., Van der Krol et al., Biotechniques 6:958–976, (1988); Stein et al., Cancer Res. 48:2659–2668 (1988)).

By mimetic is meant a molecule which resembles in shape and/or charge distribution LBP or a binding molecule. The mimetic can be a peptide or a non-peptide. Mimetics can act as therapeutic agents because they can, e.g., competitively inhibit binding of LBP to a binding molecule. By employing, e.g., scanning mutagenesis, e.g., alanine scanning mutagenesis, linker scanning mutagenesis or saturation mutagenesis, to map the amino acid residues of a particular LBP polypeptide involved in binding a binding molecule, peptide mimetics, e.g., diazepine or isoquinoline derivatives, can be generated which mimic those residues in binding to a binding molecule, and which therefore can inhibit binding of the LBP to a binding molecule and thereby interfere with the function of LBP. Non-hydrolyzable peptide analogs of such residues can be generated using, e.g., benzodiazepine (see, e.g., Freidinger et al., in Peptides: Chemistry and Biology, G. R. Marshall ed., ESCOM Publisher: Leiden, Netherlands (1988)); azepine (see, e.g., Huffman et al., in Peptides: Chemistry and Biology, G. R. Marshall ed., ESCOM Publisher: Leiden, Netherlands (1988)); substituted gamma lactam rings (see, e.g., Garvey et al., in Peptides: Chemistry and Biology, G. R. Marshall ed., ESCOM Publisher: Leiden, Netherlands (1988)); keto-methylene pseudopeptides (see, e.g., Ewenson et al., J. Med. Chem. 29:295 (1986); Ewenson et al., in Peptides: Structure and Function (Proceedings of the 9th American Peptide Symposium) Pierce Chemical Co. Rockland, Ill. (1985)); β-turn dipeptide cores (see, e.g., Nagai et al., Tetrahedron Lett. 26:647 (1985); Sato et al., J. Chem. Soc. Perkin Trans. 1:1231 (1986)); or β-aminoalcohols (see, e.g., Gordon et al., Biochem. Biophys. Res. Commun. 126:419 (1985); Dann et al., Biochem. Biophys. Res. Commun. 134:71 (1986)).

Antibodies are meant to include antibodies against any moiety that directly or indirectly affects LBP metabolism. The antibodies can be directed against, e.g., LBP or a binding molecule, or a subunit or fragment thereof. For example, antibodies include anti-LBP-1, LBP-2 or LBP-3 antibodies; and anti-binding molecule antibodies. Antibody fragments are meant to include, e.g., Fab fragments, Fab' fragments, F(ab')$_2$ fragments, F(v) fragments, heavy chain monomers, heavy chain dimers, heavy chain trimers, light chain monomers, light chain dimers, light chain trimers, dimers consisting of one heavy and one light chain, and peptides that mimic the activity of the anti-LBP or anti-binding molecule antibodies. For example, Fab$_2$' fragments of the inhibitory antibody can be generated through, e.g., enzymatic cleavage. Both polyclonal and monoclonal antibodies can be used in this invention. Preferably, monoclonal antibodies are used. Natural antibodies, recombinant antibodies or chimeric-antibodies, e.g., humanized antibodies, are included in this invention. Preferably, humanized antibodies are used when the subject is a human. Most preferably, the antibodies have a constant region derived from a human antibody and a variable region derived from an inhibitory mouse monoclonal antibody. Production of polyclonal antibodies to LBP is described in Example 6. Monoclonal and humanized antibodies are generated by standard methods known to those skilled in the art. Monoclonal antibodies can be produced, e.g., by any technique which provides antibodies produced by continuous cell lines cultures. Examples include the hybridoma technique (Kohler and Milstein, Nature 256:495–497 (1975), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, A. R. Liss, Inc., pp. 77–96 (1985)). Preferably, humanized antibodies are raised through conventional production and harvesting techniques (Berkower, I., Curr. Opin. Biotechnol. 7:622–628 (1996); Ramharayan and Skaletsky, Am. Biotechnol. Lab 13:26–28 (1995)). In certain preferred embodiments, the antibodies are raised against the LBP, preferably the LDL-binding site, and the Fab fragments produced. These antibodies, or fragments derived therefrom, can be used, e.g., to block the LDL-binding sites on the LBP molecules.

Agents also include inhibitors of a molecule that are required for synthesis, post-translational modification, or functioning of LBP and/or a binding molecule, or activators of a molecule that inhibits the synthesis or functioning of LBP and/or the binding molecule. Agents include, e.g., cytokines, chemokines, growth factors, hormones, signaling components, kinases, phosphatases, homeobox proteins, transcription factors, editing factors, translation factors and post-translation factors or enzymes. Agents are also meant to include ionizing radiation, non-ionizing radiation, ultrasound and toxic agents which can, e.g., at least partially inactivate or destroy LBP and/or the binding molecule.

An agent is also meant to include an agent which is not entirely LBP specific. For example, an agent may alter other genes or proteins related to arterial plaque formation. Such overlapping specificity may provide additional therapeutic advantage.

The invention also includes the agent so identified as being useful in treating atherosclerosis.

The invention also includes a method for evaluating an agent for the ability to alter the binding of LBP polypeptide to a binding molecule. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

In preferred embodiments, the LBP polypeptide is LBP-1, LBP-2 or LBP-3. Examples of a binding molecule include native LDL, modified LDL, e.g., methylated LDL or oxidized LDL, and arterial extracellular matrix structural components.

Altering the binding includes, e.g., inhibiting or promoting the binding. The efficacy of the agent can be assessed, e.g., by generating dose response curves from data obtained using various concentrations of the agent. Methods for determining formation of a complex are standard and are known to those skilled in the art, e.g., affinity coelectrophoresis (ACE) assays or ELISA assays as described herein.

The invention also includes the agent so identified as being able to alter the binding of an LBP polypeptide to a binding molecule.

The invention also includes a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated. Preferably, the LBP polypeptide is LBP-1, LBP-2 or LBP-3. Binding can be determined, e.g., by measuring formation of a complex by standard methods known to those skilled in the art, e.g., affinity coelectrophoresis (ACE) assays or ELISA assays as described herein.

The invention also includes the agent so identified as being able to bind to LBP polypeptide.

The invention also includes a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated. Preferably, the LBP regulatory sequence is an LBP-1, LBP-2 or LBP-3 regulatory sequence. Binding can be determined, e.g., by measuring formation of a complex by standard methods known to those skilled in the art, e.g., DNA mobility shift assays, DNase I footprint analysis (Ausubel et al., ed., Current Protocols in Molecular Biology, John Wiley & Sons, New York, N.Y., (1989)).

The invention also includes the agent so identified as being able to bind to a nucleic acid encoding an LBP regulatory sequence.

The invention also includes a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs.

In certain preferred embodiments, the agent is an LBP polypeptide, e.g., LBP-1, LBP-2 or LBP-3, or a biologically active fragment or analog thereof. The agent can be, e.g., the polypeptide as set forth in SEQ ID NOS:1–9. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues. Acidic amino acid residues include aspartic acid and glutamic acid. An example of such an LBP polypeptide is BHF-1, which is a 20 amino acid length fragment of human or rabbit LBP-1 which contains amino acid residues 14 through 33. See FIG. 9 (SEQ ID NO:9). 45% of the amino acid residues of BHF-1 are acidic. The invention also includes biologically active fragments and analogs of BHF-1.

Other preferred acidic regions from the LBPs are amino acid residues 8 through 22 (SEQ ID NO:19), 8 through 33 (SEQ ID NO:20), 23 through 33 (SEQ ID NO:21), and 208 through 217 (SEQ ID NO:22) of human LBP-2 as depicted in FIG. 7 (SEQ. ID NO:7); amino acid residues 14 through 43 (SEQ ID NO:23) and 38 through. 43 (SEQ ID NO:24) of rabbit or human LBP-1 as depicted in FIG. 1 (SEQ ID NO:1) and FIG. 6 (SEQ ID NO:6); amino acid residues 105 through 120 (SEQ ID NO:25), 105 through 132 (SEQ ID NO:26), 121 through 132 (SEQ ID NO:27), and 211 through 220 (SEQ ID NO:28) of rabbit LBP-2 as depicted in FIG. 2 (SEQ ID NO:2); amino acid residues 96 through 110 (SEQ ID NO:29) of rabbit LBP-3 as depicted in FIG. 5 (SEQ ID NO:5); and amino acid residues 53–59 (SEQ ID NO:41) of human LBP-3 as depicted in FIG. 8 (SEQ ID NO:8). The invention is also meant to include biologically active fragments and analogs of any of these polypeptides.

Other examples of agents include homopolymers and heteropolymers of any amino acid or amino acid analog. In certain preferred embodiments, the agent is a homopolymer of an acidic amino acid or analog thereof. In certain embodiments, the agent is a heteropolymer of one or more acidic amino acids and one or more other amino acids, or analogs thereof. For example, agents include poly(glu), poly(asp), poly(glu asp), poly(glu N), poly(asp N) and poly(glu asp N). By N is meant any amino acid, or analog thereof, other than glu or asp. By poly(glu asp) is meant all permutations of glu and asp for a given length peptide. A preferred peptide is poly(glu) of no more than about 10 amino acids in length, preferably about 7 amino acids in length.

In certain preferred embodiments, the agent is an LBP nucleic acid or a biologically active fragment or analog thereof, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS:10–18. In other embodiments, the agent is an antisense molecule, e.g., one which can bind to an LBP gene sequence.

Treating is meant to include, e.g., preventing, treating, reducing the symptoms of, or curing the atherosclerosis. Administration of the agent can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants.

Examples of systems in which release occurs in bursts include, e.g., systems in which the agent is entrapped in liposomes which are encapsulated in a polymer matrix, the liposomes being sensitive to a specific stimulus, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used.

The agent can be administered prior to or subsequent to the appearance of atherosclerosis symptoms. In certain embodiments, the agent is administered to patients with familial histories of atherosclerosis, or who have phenotypes that may indicate a predisposition to atherosclerosis, or who have been diagnosed as having a genotype which predisposes the patient to atherosclerosis, or who have other risk factors, e.g., hypercholesterolemia, hypertension or smoking.

The agent is administered to the animal in a therapeutically effective amount. By therapeutically effective amount is meant that amount which is capable of at least partially preventing or reversing atherosclerosis. A therapeutically effective amount can be determined on an individual basis and will be based, at least in part, on consideration of the species of animal, the animal's size, the animal's age, the agent used, the type of delivery system used, the time of administration relative to the onset of atherosclerosis symptoms, and whether a single, multiple, or controlled release dose regimen is employed. A therapeutically effective amount can be determined by one of ordinary skill in the art employing such factors and using no more than routine experimentation.

Preferably, the concentration of the agent is at a dose of about 0.1 to about 1000 mg/kg body weight/day, more preferably at about 0.1 to about 500 mg/kg/day, more preferably yet at about 0.1 to about 100 mg/kg/day, and most preferably at about 0.1 to about 5 mg/kg/day. The specific concentration partially depends upon the particular agent used, as some are more effective than others. The dosage concentration of the agent that is actually administered is dependent at least in part upon the final concentration that is desired at the site of action, the method of administration, the efficacy of the particular agent, the longevity of the particular agent, and the timing of administration relative to the onset of the atherosclerosis symptoms. Preferably, the dosage form is such that it does not substantially deleteriously affect the animal. The dosage can be determined by one of ordinary skill in the art employing such factors and using no more than routine experimentation.

In certain embodiments, various gene constructs can be used as part of a gene therapy protocol to deliver nucleic acids encoding an agent, e.g., either an agonistic or antagonistic form of an LBP polypeptide. For example, expression vectors can be used for in vivo transfection and expression of an LBP polypeptide in particular cell types so as to reconstitute the function of, or alternatively, abrogate the function of, LBP polypeptide in a cell in which non-wild type LBP is expressed. Expression constructs of the LBP polypeptide, and mutants thereof, may be administered in any biologically effective carrier, e.g. any formulation or composition capable of effectively delivering the LBP gene to cells in vivo. Approaches include, e.g., insertion of the subject gene in viral vectors including, e.g., recombinant retroviruses, adenovirus, adeno-associated virus, and herpes simplex virus-1, or recombinant bacterial or eukaryotic plasmids. Viral vectors infect or transduce cells directly; plasmid DNA can be delivered with the help of, for example, cationic liposomes (lipofectin™ (Life Technologies, Inc., Gaithersburg, Md.) or derivatized (e.g. antibody conjugated), polylysine conjugates, gramacidin S, artificial viral envelopes or other such intracellular carriers, as well as direct injection of the gene construct or $Ca_3(PO_4)_2$ precipitation carried out in vivo. The above-described methods are known to those skilled in the art and can be performed without undue experimentation. Since transduction of appropriate target cells represents the critical first step in gene therapy, choice of the particular gene delivery system will depend on such factors as the phenotype of the intended target and the route of administration, e.g., locally or systemically. Administration can be directed to one or more cell types, and to one or more cells within a cell type, so as to be therapeutically effective, by methods that are known to those skilled in the art. In a preferred embodiment, the agent is administered to arterial wall cells of the animal. For example, a genetically engineered LBP gene is administered to arterial wall cells. In certain embodiments, administration is done in a prenatal animal or embryonic cell. It will be recognized that the particular gene construct provided for in in Vivo transduction of LBP expression is also useful for in vitro transduction of cells, such as for use in the diagnostic assays described herein.

In certain embodiments, therapy of atherosclerosis is performed with antisense nucleotide analogs of the genes which code for the LBPs. Preferably, the antisense nucleotides have non-hydrolyzable "backbones," e.g., phosphorothioates, phosphorodithioates or methylphosphonates. The nucleoside base sequence is complementary to the sequence of a portion of the gene coding for, e.g., LBP-1, 2 or 3. Such a sequence might be, e.g., ATTGGC if the gene sequence for the LBP is TAACCG. One embodiment of such therapy would be incorporation of an antisense analog of a portion of one of the LBP genes in a slow-release medium, e.g., polyvinyl alcohol, which is administered, e.g., by subcutaneous injection, so as to release the antisense nucleotide analog over a period of weeks or months. In another embodiment, the antisense analog is incorporated into a polymeric matrix, e.g., polyvinyl alcohol, such that the gel can be applied locally to an injured arterial wall to inhibit LBP synthesis and prevent LDL accumulation, e.g., after angioplasty or atherectomy.

The invention also includes a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs. Being at risk for atherosclerosis can result from, e.g., a family history of atherosclerosis, a genotype which predisposes to atherosclerosis, or phenotypic symptoms which predispose to atherosclerosis, e.g., having hypercholesterolemia, hypertension or smoking.

The invention also includes a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

In certain embodiments, the cell is obtained from a cell culture or tissue culture or an embryo fibroblast. The cell can be, e.g., part of an animal, e.g., a natural animal or a non-human transgenic animal. Preferably, the LBP is LBP-1, LBP-2 or LBP-3.

The invention also includes a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier. Pharmaceutically acceptable carriers include, e.g., saline, liposomes and lipid emulsions.

In certain preferred embodiments, the agent of the pharmaceutical composition is an LBP polypeptide, e.g., LBP-1, LBP-2 or LBP-3, or a biologically active fragment or analog thereof. The agent can be, e.g., the polypeptide as set forth in SEQ ID NOS:1–9. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues.

In certain preferred embodiments, the agent is an LBP nucleic acid, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS:10–18.

The invention also includes a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

The invention also includes a method for diagnosing atherosclerotic lesions in an animal. An animal is provided. A labeled agent capable of binding to LBP present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Preferably, the LBP is LBP-1, LBP-2 or LBP-3. The imaging can be performed by standard methods known to those skilled in the art, including, e.g., magnetic resonance imaging, gamma camera imaging, single photon emission computed tomographic (SPECT) imaging, or positron emission tomography (PET).

Preferably, agents that bind tightly to LBPs in atherosclerotic lesions are used for atherosclerotic imaging and diagnosis. The agent is radiolabeled with, e.g., $^{99m}$Tc or another isotope suitable for clinical imaging by gamma camera, SPECT, PET scanning or other similar technology. Since LBPs occur in very early lesions, such imaging is more sensitive than angiography or ultrasound for locating very early lesions which do not yet impinge on the arterial lumen to cause a visible bulge or disturbed flow. In addition to locating both early and more developed lesions, the imaging agents which bind to LBPs. can also be used to follow the progress of atherosclerosis, as a means of evaluating the effectiveness of both dietary and pharmacological treatments.

Thus, a diagnostic embodiment of the invention is the adaptation of, e.g., a peptide complementary to one of the LBPs, by radiolabeling it and using it as an injectable imaging agent for detection of occult atherosclerosis. The peptide is selected from those known to bind to LBPs, e.g., RRRRRRR or KKLKLXX, or any other polycationic peptide which binds to the highly electronegative domains of the LBPs. For extracorporeal detection with a gamma scintillation (Anger) camera, technetium-binding ligands, e.g., CGC, GGCGC, or GGCGCF, can be incorporated into the peptides at the N-terminus or C-terminus for $^{99m}$Tc labeling. For external imaging by magnetic resonance imaging (MRI), e.g., the gadolinium-binding chelator, diethylene triamine penta-acetic acid (DTPA), is covalently bound to the N- or C-terminus of the peptides. In yet other embodiments, the LBP-binding peptides are covalently bound, e.g., to magnetic ion oxide particles by standard methods known to those skilled in the art, e.g., conjugating the peptides with activated polystyrene resin beads containing magnetic ion oxide.

The invention also includes a method for immunizing an animal against an LBP, e.g., LBP-1, LBP-2 or LBP-3, or fragment or analog thereof. An animal having LDL is provided. An LBP or fragment or analog thereof is provided. The LBP or fragment or analog thereof is administered to the animal so as to stimiulate antibody production by the animal to the LBP or fragment or analog thereof such that binding of the LBP to the LDL is altered, e.g., decreased or increased.

The invention also includes a method of making a fragment or analog of LBP polypeptide, the fragment or analog having the ability to bind to modified LDL and native LDL. An LBP polypeptide is provided. The sequence of the LBP polypeptide is altered. The altered LBP polypeptide is tested for the ability to bind to modified LDL, e.g., methylated LDL, oxidized LDL, acetylated LDL, cyclohexanedione-treated LDL (CHD-LDL), and to native LDL.

The fragments or analogs can be generated and tested for their ability to bind to these modified LDLs and to native LDL, by methods known to those skilled in the art, e.g., as described herein. Preferably, they are tested for their ability to bind to methylated LDL and native LDL. The binding activity of the fragment or analog can be greater or less than the binding activity of the native LBP. Preferably, it is greater. In preferred embodiments, the LBP is LBP-1, LBP-2 or LBP-3.

The invention also includes a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes this polypeptide is isolated, the cDNA encoding an LBP.

The following non-limiting examples further illustrate the present invention.

EXAMPLES

Example 1

Construction of a Rabbit cDNA Library

This example illustrates the construction of a rabbit cDNA library using mRNA from balloon-deendothelialized healing rabbit abdominal aorta. Balloon-catheter deendothelialized rabbit aorta has been shown to be a valid model for atherosclerosis (Minick et al., Am. J. Pathol. 95:131–158 (1979).

The mRNA was obtained four weeks after ballooning to maximize focal LDL binding in the ballooned rabbit aorta. First strand cDNA synthesis was carried out in a 50 $\mu$l reaction mixture containing 4 $\mu$g mRNA; 2 $\mu$g oligo d(T) primer; methylation dNTP mix (10 mM each); 10 mM DTT; 800 units superscript II RT (Life Technologies, Gaithersburg, Md.); 1× first strand cDNA synthesis buffer (50 mM Tris-HCl, pH 8.3; 75 mM KCl; 5 mM $MgCl_2$), which was incubated for 1 hr at 37° C. The reaction mixture was then adjusted to 250 $\mu$l through the addition of 1× second strand buffer (30 mM Tris-HCl, pH 7.5; 105 mM KCl; 5.2 mM $MgCl_2$); 0.1 mM DTT; methylation dNTP mix (10 mM each); 50 units E. coli DNA polymerase I, 3 units RNase H; 15 units E. coli DNA ligase (all enzymes from Life Technologies), which was incubated for an additional 2.5 hr at 15° C. The resulting double-stranded cDNAs (dscDNA) were then treated with 1.5 units T4 DNA polymerase (Novagen Inc., Madison, Wis.) for 20 min at 11° C. to make blunt-ended dscDNA. These were then concentrated by ethanol precipitation and EcoR1/Hind III linkers were attached to the ends by T4 DNA ligase (Novagen Inc.). The linker-ligated cDNAs were treated with EcoR1 and HindIII restriction enzymes to produce EcoR1 and Hind III recognition sequences at their 5' and 3' ends, respectively. After the removal of linker DNA by gel exclusion chromatography, the dscDNAs were inserted into $\lambda$EXlox phage arms (Novagen Inc.) in a unidirectional manner by T4 DNA ligase and packaged into phage particles according to the manufacturer's protocol (Novagen Inc.). A phage library of cDNAs containing $2 \times 10^6$ independent clones was established from 4 $\mu$g of mRNA.

Example 2

Identification of Rabbit cDNAs Encoding LDL Binding Proteins (LBPs)

This example illustrates a method of functionally screening a rabbit cDNA library so as to identify cDNAs encoding LBPs which bind to both native LDL and methyl LDL. Methyl LDL is not recognized by previously reported cell surface receptors. See, e.g., Weisgraber et al., J. Biol. Chem. 253:9053–9062 (1978).

A fresh overnight culture of E. coli ER1647 cells (Novagen Inc.) was infected with the cDNA phage obtained from Example 1, and plated at a density of $2 \times 10^4$ plaque-forming units (pfu) in 150 mm diameter plates containing 2× YT agar. A total of 50 plates, equivalent to $1 \times 10^6$ phage, were plated and incubated at 37° C. until the plaques reached 1 mm in diameter (5–6 hr). A dry nitrocellulose membrane, which had previously been saturated with 10 mM IPTG solution, was layered on top of each plate to induce the production of recombinant protein, as well as to immobilize the proteins on the membranes. The plates were incubated at 37° C. for an additional 3–4 hr, and then overnight at 4° C.

The next day, the membranes were lifted from each plate and processed as follows. Several brief rinses in TBST solution (10 mM Tris-HCl, pH 8.0; 150 mM NaCl, 0.05% Tween 20); two 10-min rinses with 6M guanidine-HCl in HBB (20 mM HEPES, pH 7.5; 5 mM $MgCl_2$, 1 mM DTT, and 5 mM KCl); two 5-min rinses in 3M guanidine-HCl in HBB; a final brief rinse in TBSEN (TBS, 1 mM EDTA, 0.02% $NaN_3$).

The membranes were then blocked for 30 min at room temperature in a solution of TBSEN with 5% non-fat dry milk, followed by 10 min in TBSEN with 1% non-fat dry milk. Following blocking, the membranes were incubated with native human LDL (obtained as described in Example 11 or methylated human LDL (meLDL) (see Weisgraber et al., J. Biol. Chem. 253:9053–9062 (1978)), at a concentration of 4 $\mu$g/ml, in a solution containing 1× TBSEN, 1% non-fat dry milk, 1 mM PMSF, 0.5× protease inhibitor solution (1 mm $\epsilon$-amino caproic acid/1 mM benzamidine). Incubation was for 4 hr at room temperature in a glass Petri dish with gentle stirring on a stirring table, followed by overnight at 4° C. with no stirring.

Specifically bound meLDL and native LDL were detected on the nitrocellulose membranes by antibodies against human LDL. Sheep anti-human LDL polyclonal antibodies (Boehringer Mannheim, Indianapolis, Ind.) were adsorbed with E. coli plys E cell extracts to abolish background. For adsorption, E. coli plys E cells were grown to log phase, spun down and resuspended in PBS containing 1 mM PMSF, 2 mM $\epsilon$-amino caproic acid, and 1 mM benzamidine. The cell suspension then underwent 8 freeze-thaw cycles via immersion in liquid nitrogen and cold running tap water, respectively. The anti LDL antibodies/cell extract solution were incubated with gentle stirring for 1 hr at 4° C. (1 ml of antibody solution/3 mg crude cell extract). Following incubation, the mixture was centrifuged (10,000×g; 10 min; 4° C.) and the supernatant was stored at 4° C. in the presence of 0.02% $NaN_3$ until use. The membranes were processed for immunoscreening as follows: (i) three 5-min washes at room temperature in TBSEN containing 1% gelatin; (ii) 30 min incubation in PBS, pH 7.4 with 1% gelatin; (iii) two-hr room temperature incubation with gentle stirring in fresh PBS/gelatin solution containing adsorbed sheep anti-human LDL antibodies (Boehringer Manheim, Indianapolis, Ind.) (1:1000 dilution); (iv) three brief washes in TBS, pH 7.4; (v) one-hr room temperature incubation with gentle stirring in PBS/gelatin solution containing donkey antisheep alkaline phosphatase-conjugated antibodies (Sigma, St. Louis, Mo.) (1:10,000 dilution); (vi) three brief washes with TBS, pH 7.4.; and (vii) development according to the manufacturer's instructions, using an alkaline phosphatase substrate development kit (Novagen Inc.). Phage plaques which produced LBPs appeared as blue-colored "donuts" on the membranes.

The phage from Example 1 containing the LBP cDNAs were plaque-purified and converted into plasmid subclones by following a protocol called "Autosubcloning by Cre-mediated Plasmid Excision" provided by Novagen Inc. DNA sequences were obtained by the dideoxynucleotide chain-termination method (Sanger et al., Proc. Natl. Acad. Sci., USA 74:5463–54.67 (1977), and analyzed by an Applied Biosystems automated sequencer. The open reading frame (ORF) of each cDNA was determined from consensus sequences obtained from both the sense and antisense strands of the cDNAs. Sequencing confirmed that three previously unknown genes had been isolated. Since the genes were selected by functional screening for LDL binding, the proteins coded by these genes were termed LDL binding proteins (LBPs), specifically, LBP-1, LBP-2 and LBP-3. The cDNA sequences for rabbit LBP-1, LBP-2 and LBP-3 and the corresponding proteins are set forth in SEQ ID NOS:10–14.

Based on their respective cDNA coding sequences, the sizes of the recombinant proteins were determined to be 16.2 kDa for LBP-1, 40 kDa for LBP-2, and 62.7 kDa for LBP-3.

Example 3

Northern Blot Analysis of Rabbit RNA Using LBP cDNA or cRNA

This example illustrates the size and tissue distribution of LBP mRNAs. Total RNA was isolated from different rabbit tissues: adrenals, thoracic aorta, abdominal aorta, ballooned and reendothelialized abdominal aorta, heart, kidney, smooth muscle cells, lung and liver, by Trizol reagent (Life Technologies) and concentrated by ethanol precipitation. Gel electrophoresis of RNA was carried out in 1.2% agarose gel containing 1× MOPS buffer (0.2M MOPS, pH 7.0; 50 mM sodium acetate; 5 mM EDTA, pH 8.0) and 0.37M formaldehyde. Gels were loaded with 20 µg total RNA from each tissue examined and electrophoresed at 100 volts for 2 hr in 1× MOPS buffer. RNAs were blotted onto supported nitrocellulose membranes (Schleicher & Schuell, Keene, N. H.) and immobilized by baking at 80° C. for 2 hr. Hybridization to radiolabeled LBP-1, LBP-2 and LBP-3 cDNA or cRNA probes was carried out by standard procedures known to those skilled in the art (see, e.g., Ausubel et al., Current Protocols in Molecular Biology; John Wiley & Sons (1989)); signals were detected by autoradiography.

The results were as follows: the sizes of the mRNAs were about 1.3 kb for LBP-1, about 2.3–2.5 kb for LBP-2, and about 4.7 kb for LBP-3. LBP-1, LBP-2 and LBP-3 mRNA were found in all tissues tested, but the highest amount was in ballooned abdominal aorta.

Example 4

Isolation of Human LBP cDNAs

This example illustrates isolation of human LBP cDNAs. Human LBP cDNA clones were isolated from three cDNA libraries. A human fetal brain cDNA library was obtained from Stratagene, Lajolla, Calif., a human liver and a human aorta cDNA library were obtained from Clontech, Palo Alto, Calif., and screened with a radiolabeled cDNA probe derived from rabbit LBP-1, LBP-2 or LBP-3, according to the method described in Law et al., Gene Expression 4:77–84 (1994). Several strongly hybridizing clones were identified and plaque-purified. Clones were confirmed to be human LBP-1, LBP-2 and LBP-3, by DNA sequencing using the dideoxynucleotide chain-termination method and analysis by an Applied Biosystems automated sequencer. The cDNA sequences and the corresponding proteins for human LBP-1, LBP-2 and LBP-3 are set forth in SEQ ID NOS:15, 16 and 17, respectively. A comparison between the corresponding LBP-1, LBP-2 and LBP-3 protein sequences for rabbit and human are shown in FIGS. 19, 20 and 21.

Example 5

Isolation of Recombinant LBP-1, LBP-2 and LBP-3 Rabbit Proteins from E. coli LBP cDNA was isolated from the original pEXlox plasmids obtained as described in Examples 1 and 2, and subcloned into the pPROEX-HT vector (Life Technologies) for recombinant protein expression. Induction of the recombinant protein by IPTG addition to transformed E. coli DH10B cultures resulted in the expression of recombinant protein containing a 6-histidine tag (N-terminal). This tagged protein was then purified from whole cell proteins by binding to Ni-NTA (nickel nitrilo-triacetic acid) as described in the protocol provided by the manufacturer (Qiagen, Inc., Santa Clara, Calif.). The preparation obtained after the chromatography step was approximately 90% pure; preparative SDS-PAGE was performed as the final purification step.

When required by the characterization procedure, iodination of LBPs was carried out using Iodobeads (Pierce, Rockford, Ill.). The Iodobeads were incubated with 500 µCi of Na$^{125}$I solution (17 Ci/mg) (New England Nuclear, Boston, Mass.) in a capped microfuge tube for 5 min at room temperature. The protein solution was added to the Iodobeads-Na$^{125}$I microfuge tube and incubated for 15 min at room temperature. At the end of this incubation, aliquots were removed for the determination of total soluble and TCA precipitable counts. The radiolabeled protein was then precipitated with cold acetone (2.5 vol; −20° C.; 2.5 hr) Following this incubation, precipitated protein was collected by centrifugation (14,000 g; 1 hr; room temperature) and resuspended in sample buffer (6 M urea/50 mM Tris, pH 8.0/2 mM EDTA). Integrity of the protein preparation was assessed by SDS-PAGE.

The identities of the recombinant LBPs were confirmed using standard protein sequencing protocols known to those skilled in the art. (A Practical Guide for Protein and Peptide Purification for Microsequencing, Matsudaira, ed., Academic Press, Inc., 2d edition (1993)). Analysis was performed using an Applied Biosystems Model 477A Protein Sequencer with on-line Model 120 PTH amino acid analyzer.

Example 6

Production of Antibodies to LBP-1, LBP-2 and LBP-3

This example illustrates the production of polyclonal antibodies to LBP-1, LBP-2 and LBP-3. A mixture of purified recombinant LBP protein (0.5 ml; 200 µg) and RIBI adjuvant (RIBI ImmunoChem Research, Inc., Hamilton, Mont.) was injected subcutaneously into male guinea pigs (Dunkin Hartley; Hazelton Research Products,. Inc., Denver, Pa.) at 3–5 sites along the dorsal thoracic and abdominal regions of the guinea pig. Blood was collected by venipuncture on days 1 (pre-immune bleeding), 28, 49 and 70. Booster injections were administered on days 21 (100 µg; SC), 42 (50 µg; SC), and 63 (25 µg; SC) The titer of the guinea pig antiserum was evaluated by serial dilution "dot blotting." Preimmune antiserum was evaluated at the same time. After the third booster of LBP protein, the titer against the recombinant protein reached a maximal level with a detectable. colorimetric response on a dot blot assay of 156 pg.

Specificity of the polyclonal antibody for recombinant LBP-1, LBP-2 or LBP-3 was demonstrated using Western blot analysis. (Towbin et al., Proc. Natl. Acad. Sci. USA 76:4350 (1979)). The protein-antibody complex was visualized immunochemically with alkaline phosphatase-conjugated goat anti-guinea pig IgG, followed by staining with nitro blue tetrazolium (BioRad Laboratories, Hercules, Calif.). Non-specific binding was blocked using 3% non-fat dry milk in Tris buffered saline (100 mM Tris; 0.9% NaCl, pH 7.4).

Example 7

Immunohistochemical Characterization

This example illustrates the presence of LBPs in or on endothelial cells covering plaques, in or on adjacent smooth muscle cells, and in the extracellular matrix. In addition, co-localization of LDL and LBPs was demonostrated. These results were obtained by examining ballooned rabbit arterial lesions and human atherosclerotic plaques by immunohistochemical methods.

Ballooned deendothelialized aorta was obtained from rabbits which had received a bolus injection of human LDL (3 mg; i.v.) 24 hr prior to tissue collection. Human aortas containing atherosclerotic plaques were obtained-from routine autopsy specimens. Tissues were fixed in 10 buffered formalin ($\leq$24 hr) and imbedded in paraffin using an automated tissue-imbedding machine. Tissue sections were cut (5–7 $\mu$) and mounted onto glass slides by incubating for 1 hr at 60° C. Sections were deparaffinized. After a final wash with deionized $H_2O$, endogenous peroxidase activity was eliminated by incubating the sections with 1% $H_2O_2/H_2O$ buffer for 5 min at room temperature. Sections were rinsed with phosphate buffered saline (PBS) for 5 min at room temperature and nonspecific binding was blocked with 5% normal goat serum or 5% normal rabbit serum depending on the source of the secondary antibody (Sigma, St. Louis, Mo.) (1 hr; room temperature). Sections were then incubated with a 1:50 dilution (in 5% normal goat serum/PBS) of a guinea pig polyclonal antibody against the rabbit form of recombinant LBP-1, LBP-2 or LBP-3. Controls included preimmune serum as well as specific antisera to LBP-1, LBP-2, or LBP-3 in which the primary antibody was completely adsorbed and removed by incubation with recombinant LBP-1, LBP-2 or LBP-3 followed by centrifugation prior to incubation with the tissue sections. An affinity purified rabbit polyclonal antibody against human apolipoprotein B (Polysciences Inc.; Warrington, Pa.) was used at a dilution of 1:100 (in 5% normal rabbit serum/PBS). Sections were incubated for 2 hr at room temperature in a humidified chamber. At the end of incubation, sections were rinsed with PBS and incubated with a 1:200 dilution.(in 5% normal goat serum/PBS) of goat anti-guinea pig biotinylated IgG conjugate (Vector Laboratories, Burlingame, Calif.) or a 1:250 dilution (in 5% normal rabbit serum/PBS) of rabbit anti-goat biotinylated IgG conjugate (Vector Laboratories, Burlingame, Calif.) for 1 hr at room temperature in a humidified chamber. Sections were then rinsed with PBS and antigen-antibody signal amplified using avidin/biotin HRP conjugate (Vectastain ABC kit; Vector Laboratories, Burlingame, Calif.). Sections were developed using DAB substrate (4–6 min; room temperature) and counterstained with hematoxylin.

In the ballooned rabbit artery, immunohistochemistry with the anti-LBP-1, LBP-2 and LBP-3 antibodies showed that LBP-1, LBP-2 and -LBP-3 were located in or on functionally modified endothelial cells at the edges of regenerating endothelial islands, the same location in which irreversible LDL binding has been demonstrated (Chang et al., Arteriosclerosis and Thrombosis 12:1088–1098 (1992)). LBP-1, LBP-2 and LBP-3 were also found in or on intimal smooth muscle cells underneath the functionally modified endothelial cells, and to a lesser extent, in extracellular matrix. No LBP-1, LBP-2 or LBP-3 was detected in still deendothelialized areas, where LDL binding had been shown to be reversible (Chang et al., Arteriosclerosis and Thrombosis 12:1088–1098 (1992)). Immunohistochemistry of ballooned rabbit aorta with anti-human apolipoprotein B antibodies showed the presence of LDL at the same locations as that found for LBP-1, LBP-2 and LBP-3.

In the human atherosclerotic plaques taken at routine autopsies, immunohistochemistry with the anti-LBP-1, anti-LBP-2 and anti-LBP-3 antibodies showed that LBP-1, LBP-2, and LBP-3 were also-found in or on endothelial cells covering plaques and in or on adjacent smooth muscle cells. In the human tissue, there was greater evidence of LBP-1, LBP-2 and LBP-3 in extracellular matrix.

The results obtained with paraffin sections were identical to those of frozen sections.

Example 8

Affinity Coelectrophoresis (ACE) Assays of LBPs and LDL or HDL

This example illustrates that binding occurs between LBP-1, LBP-2 or LBP-3 and LDL, and that this binding is specific, as illustrated by the fact that binding does not occur between LBP-1, LBP-2 or LBP-3 and HDL (high density lipoprotein).

Analysis of the affinity and specificity of recombinant rabbit LBP-1, LBP-2 or LBP-3 binding to LDL was carried out using the principle of affinity electrophoresis (Lee and Lander, Proc. Natl. Acad. Sci. USA 88:2768–2772 (1991)). Melted agarose (1%; 65° C.) was prepared in 50 mM sodium MOPS, pH 7.0; 125 mM sodium acetate, 0.5% CHAPS. A teflon comb consisting of nine parallel bars (45×4×4 mm/3 mm spacing between bars) was placed onto GelBond film (FMC Bioproducts, Rockland, Me.) fitted to a plexiglass casting tray with the long axis of the bars parallel to the long axis of the casting tray. A teflon strip (66×1×1 mm) was placed on edge with the long axis parallel to the short axis of the casting tray, at a distance of 4 mm from the edge of the teflon comb. Melted agarose (>65+ C.) was then poured to achieve a height of approximately 4 mm. Removal of the comb and strip resulted in a gel containing nine 45×4×4 mm rectangular wells adjacent to a 66×1 mm slot. LDL or HDL samples were prepared in gel buffer (50 mM sodium MOPS, pH 7.0, 125 mM sodium acetate) at twice the desired concentration. Samples were then mixed with an equal volume of melted agarose (in 50 mM MOPS, pH 7.0; 125 mM sodium acetate; 50° C.), pipetted. into the appropriate rectangular wells and allowed to gel. The binding affinity and specificity of LBP-1 and LBP-3 was tested using several concentrations of LDL (540 to 14 nM) and HDL (2840–177 nM). A constant amount (0.003 nM–0.016 nM) of $^{125}$I-labeled LBP-1, LBP-2 or LBP-3 (suspended in 50 mM sodium MOPS, pH 7.0; 125 mM sodium acetate; 0.5% bromphenol blue; 6% (wt/vol) sucrose) was loaded into the slot. Gels were electrophoresed at 70v/2hr/20° C. At the end of the run, the gels were air dried and retardation profiles were visualized by exposure of X-ray films to the gels overnight at −70° C., with intensifying screens).

LDL retarded LBP-1, LBP-2 and LBP-3 migration through the gel in a concentration-dependent, saturable manner, indicating that LBP-1, LBP-2 and LBP-3 binding to LDL was highly specific. This conclusion is supported by the fact that HDL did not retard LBP-1, LBP-2 or LBP-3. A binding curve generated from the affinity coelectrophoresis assay indicated that LBP-1 binds to LDL with a $K_d$ of 25.6 nM, that LBP-2 (rabbit clone 26) binds to LDL with a $K_d$ of 100 nM, and that LBP-3 (80 kDa fragment) binds to LDL with a $K_d$ of 333 nM.

In addition to testing affinity and specificity of LBP-1, LBP-2 and LBP-3 binding to LDL, the ability of "cold" (i.e., non-radiolabeled) LBP-1, LBP-2 or LBP-3 to competitively inhibit. radiolabeled LBP-1, LBP-2 or LBP-3 binding to LDL, respectively, was tested. Competition studies were carried out using fixed concentrations of cold LDL and radiolabeled LBP-1 and increasing amounts of cold recombinant LBP-1 (6–31 μM). The ACE assay samples and gel were prepared as described herein. Cold LBP-1 inhibited binding of radiolabeled LBP-1 to LDL in a concentration-dependent manner, cold LBP-2 inhibited binding of radiolabeled LBP-2 to LDL in a concentration-dependent manner, and cold LBP-3 inhibited binding of radiolabeled LBP-3 to LDL in a concentration-dependent manner.

Rabbit and human LBP-2 contain a long stretch of acidic amino acids at the amino terminal (rabbit LBP-2 amino acid residues 105 through 132 and human LBP-2 amino acid residues 8 through 33). The possibility that this segment of LBP-2 was the LDL binding domain was tested by subcloning two rabbit LBP-2 clones which differ from each other by the presence or absence of this acidic region (clone 26 and clone 45, respectively) into expression vectors, by standard methods known to those skilled in the art. ACE assays were then conducted in order to assess the affinity and specificity of the binding of these two clones to LDL. LDL retarded clone 26 derived radiolabeled LBP-2 migration through the gel in a concentration-dependent, saturable, manner while clone 45 derived radiolabeled LBP-2 migration was not retarded.

Competition studies using fixed concentrations of cold LDL and clone 26 derived radiolabeled LBP-2 and increasing. concentrations of cold recombinant LBP-2/clone 26 and LBP-2/clone 45 were carried out. Cold clone 26 derived LBP-2 inhibited binding of clone 26 derived radiolabeled LBP-2 to LDL in a concentration-dependent manner. Clone 45 derived LBP-2, on the other hand, did not affect the binding of clone 26 derived radiolabeled LBP-2 to LDL. These results indicate that the long stretch of acidic amino acids contain a binding domain of LBP-2 to LDL.

Example 9

Affinity Coelectrophoresis (ACE) Assays of LBP-1 or LBP-2 and LDL in the Presence of Inhibitors This example illustrates that binding between LBP-1 or LBP-2 and LDL is inhibited by polyglutamic acid or BHF-1. The ability of a third compound to inhibit binding between two proteins previously shown to interact was tested by a modification of the ACE assays described in Example 8. The third compound was added to the top or wells together with the radiolabeled protein. If the third compound inhibited binding, the radiolabeled protein would run through the gel. If the third compound did not inhibit binding, migration of the radio-labeled protein was retarded by the protein cast into the gel.

Inhibition of LBP-1/LDL or LBP-2/LDL binding by polyglutamic acid (average MW about 7500, corresponding to about 7 monomers) was shown by casting a constant amount of LDL (148 nM) in all the rectangular lanes. A constant amount (1 μl) of $^{125}$I-labeled LBP-1 or LBP-2 (0.003 nM–0.016 nM) was loaded in the wells at the top of the gel, together with increasing concentrations of polyglutamic acid (obtained from Sigma) (0–0.4 nM). The gel was electrophoresed at 70 volts for 2 hr, dried and placed on X-ray film, with intensifying screens, overnight at −70° C. before the film was developed to determine the retardation profile of LBP-1 and LBP-2. As the concentration of polyglutamic acid increased, retardation of radiolabeled LBP-1 and LBP-2 migration by LDL decreased in a concentration-dependent manner, which showed that polyglutamic acid inhibited binding between LBP-1, LBP-2 and LDL.

Inhibition of LBP-1/LDL binding by BHF-1 was shown by casting a constant amount of LDL (148 nM) in all the rectangular lanes. A constant amount of $^{125}$I-labeled LBP-1 (0.003 nM–0.016 nM) was loaded in the wells at the top of the gel, together with increasing concentrations of BHF-1 (0–10 nM), obtained as described in Example 15. The gel was electrophoresed at 70 volts for 2 hr, dried and placed on X-ray film, with intensifying screens, overnight at −70° C. The film was then developed to determine the retardation profile of $^{125}$I-LBP-1. As the concentration of BHF-1 increased, retardation of LBP-1 by LDL decreased in a concentration-dependent manner, which demonstrated that BHF-1 inhibited binding between LBP-1 and LDL.

Example 10

Affinity Coelectrorhoresis (ACE) Assays for Identifying Fragments, Analogs and Mimetics of LBPs Which Bind to LDL This example illustrates a method for identifying fragments, analogs or mimetics of LBPs which bind to LDL, and which thus can be used as inhibitors of LDL binding to LBP in the arterial walls, by occupying binding sites on LDL molecules, thereby rendering these sites unavailable for binding to LBP in the arterial wall.

Fragments of LBPs are generated by chemical cleavage or synthesized from the known amino acid sequences. Samples of these fragments are individually added (cold) to radiolabeled LBP as described in Example 8, to assess the inhibitory potency of the various fragments. By iterative application of this procedure on progressively smaller portions of fragments identified as inhibitory, the smallest active polypeptide fragment or fragments are identified. In a similar manner, analogs of the LBPs are tested to identify analogs which can act as inhibitors by binding to LDL. And, similarly, mimetics of LBP (molecules which resemble the conformation and/or charge distributions of the LDL-binding sites on LBP molecules) are tested in a similar fashion to identify molecules exhibiting affinities for the LDL-binding sites on LBP.

The affinities of the inhibitors so identified are at least as strong as the affinity of LDL itself for the LDL-binding sites on LBP. The inhibitors bind at least competitively, and some irreversibly and preferentially as well, to the LDL-binding sites, thereby rendering such sites unavailable for binding to humoral LDL.

Example 11

ELISA Assays

This example illustrates the use of an ELISA plate assay for the quantification of a test compound's capacity to inhibit the binding of LDL to a specific LBP.

The assay was carried out as follows: LDL was diluted in 50 mM $Na_2HCO_3$, pH 9.6/0.02% $NaN_3$ and added to the wells of a 96-well plate (ImmunoWare 96-Well Reacti-Bind EIA Polystyrene Plates; Pierce (Rockford, Ill.)) to achieve a final concentration ranging from 0.1 to 1 μg/well. The plates were incubated for 6 hr at room temperature. At the end of the incubation period, the wells were washed 3 times with Tris-buffered saline, pH 7.4 (TBS), and blocked overnight with 200 μl of 1% bovine serum albumin (BSA) in TBS/0.02% $NaN_3$ (Sigma; St. Louis Mo.) at room temperature. The wells were then incubated with 200 μl of LBP protein (5–10 μg/well) in TBS and varying concentrations of the test compound. Plates were incubated for 1 hr at room temperature. The wells were then washed three times with TBS and blocked for 2 hr. with 200 μl of 1% BSA in TBS/0.02% $NaN_3$ at room temperature. At the end of the incubation period, the wells were washed 3 times with TBS and a 1:1000 dilution (in TBS/0.05% Tween 20) of the appropriate guinea pig anti-LBP protein polyclonal antibody was added to the wells and incubated for 1 hr at room temperature. The wells were then washed 3 times with TBS/0.05% Tween 20; a 1:30,000 dilution of goat anti-guinea pig IgG alkaline phophatase conjugate (Sigma) was added to each well. Plates were incubated for 1 hr at room temperature. The wells were washed 3 times with TBS/0.05% Tween 20 and a chlorimetric reaction was carried out by adding 200 ml of p-nitrophenyl phosphate substrate (Sigma; St. Louis Mo.) to the wells. The reaction was allowed to proceed for 30 min at room temperature and stopped with 50 μl of 3N NaOH. The absorbance was determined at 405 nm using an ELISA plate reader. The test compound's effectiveness in blocking the binding of LDL to the recombinant protein was assessed by comparing the absorbance values of control and treated groups.

Alternatively, LBPs, rather than LDL, were bound to the plate. Recombinant LBP protein binding to LDL and the effect of varying concentration of the inhibitor on LBP-LDL binding was determined through the use of antibodies against LDL. This interaction was visualized through the use of a secondary antibody conjugated to a reporter enzyme (e.g. alkaline phosphatase).

ELISA plate assays were used to screen agents which can affect the binding of LBP proteins to LDL. For example, peptides derived from LBP-1 and human LBP-3 protein sequences (BHF-1 and BHF-2, respectively) were synthesized and have been shown to reduce the binding of LDL to recombinant LBP-1 and LBP-2 in this format. These results were in agreement with those obtained with the ACE assays.

Example 12

Administration of Humanized Antibodies Against LBPs so as to Block LDL-Binding Sites on the LBPs This example illustrates administration to patients of humanized antibodies against LBP-1, LBP-2 or LBP-3 so as to block LDL-binding sites on arterial LBP molecules. Mouse monoclonal antibodies are humanized by recombinant DNA techniques and produced by standard procedures known to those skilled in the art (Berkower, I., Curr. Opin. Biotechnol. 7:622–628 (1996); Ramharayan and Skaletsky, Am. Biotechnol. Lab 13:26–28 (1995)) against LBPs and/or the LDL-binding sites on the LBPs. The corresponding Fab fragments are also produced, as described in Goding, J. W., Monoclonal Antibodies:Principles and Practice, Academic Press, New York, N.Y. (1986). These antibodies are administered parenterally in sufficient quantity so as to block LDL-binding sites on the LBP molecules, i.e., 1–10 mg/kg daily. This prevents the irreversible arterial uptake of LDL that is required to facilitate oxidation of the LDL.

Example 13

Preparation of LDL

This example illustrates the preparation of LDL. LDL was prepared from the plasma of normolipemic donors (Chang et al., Arterioscler. Thromb. 12:1088–1098 (1992)). 100 ml of whole blood was placed into tubes containing 100 mM disodium EDTA. Plasma was separated from red blood cells by low-speed centrifugation (2,000 g; 30 min; 4° C.). Plasma density was adjusted to 1.025 gm/ml with a solution of KBr and centrifuged for 18–20 hr, 100,000×g, 12° C. Very low density lipoproteins (VLDL) were removed from the tops of the centrifuge tubes with a Pasteur pipet. The density of the infranate was raised to 1.050 gm/ml with KBr solution and centrifuged for 22–24 hr, 100,000×g, 12° C. LDL was removed from the tops of the centrifuge tubes with a drawn out Pasteur pipet tip. Purity of the LDL preparation was checked by Ouchterlony double immunodiffusion against antibodies to human LDL, human HDL, human immunoglobulins, and human albumin. KBr was removed from the LDL solution by dialysis (1L, ×2, ≈16 hr) against 0.9% saline, pH 9.0, containing 1 mM EDTA and 10 μM butylated hydroxytoluene (BHT), the latter to prevent oxidation of LDL. Following dialysis, LDL protein was measured by the method of Lowry (Lowry et al., J. Biol. Chem. 193:265–275 (1951)), and the LDL was stored at 4° C. until use. LDL preparations were kept for no more than 4–6 weeks.

Example 14

Preparation of HDL

This example illustrates the preparation of HDL. HDL was prepared from plasma of normolipemic donors. 100 ml of whole blood was placed into tubes containing 100 mM disodium EDTA and plasma was collected by centrifugation (2000 g; 30 min; 4° C.) Apolipoprotein B containing lipoproteins present in plasma were then precipitated by the sequential addition of sodium heparin (5,000 units/ml) and $MnCl_2$ (1M) to achieve a final concentration of 200 units/ml and 0.46 M, respectively (Warnick and Albers, J. Lipid Res. 19:65–76 (1978)). Samples were then centrifuged (2000 g; 1 hr; 4° C.). The supernatant was collected and density adjusted to 1.21 g/ml by the slow addition of solid KBr. HDL was separated by ultracentrifugation (100,000 g; >46 hr; 12° C.). Purity of the HDL preparation was assessed via Ouchterlony double immunodiffusion test using antibodies against human HDL, human LDL, human immunoglobulins, and human albumin. HDL samples were dialyzed against saline pH 9.0/1 mM EDTA/10 μM BHT (4L; 24 hr/4° C.) and total protein was determined by the Lowry protein assay (Lowry et al., J. Biol. Chem. 193:265–275 (1951)). HDL was stored at 4° C. until use. HDL preparations were kept for no longer than 2 weeks.

Example 15

Synthesis of BHF-1

This example illustrates the synthesis of BHF-1, a fragment of human or rabbit LBP-1 which contains amino acid residues 14 through 33. BHF-1 was synthesized using an Applied Biosystems Model 430A peptide synthesizer with standard T-Boc NMP chemistry cycles. The sequence of BHF-1 is as follows:

val-asp-val-asp-glu-tyr-asp-glu-asn-lys-phe-val-asp-glu-giu-asp-gly-gly-asp-gly (SEQ ID NO:9)

After synthesis, the peptide was cleaved with hydrofluoric acid/anisole (10/1 v/v) for 30 min at −10° C. and then incubated for 30 min at 0° C. BHF-1 was then precipitated and washed three times with cold diethyl ether. Amino acid coupling was monitored with the ninhydrin test (>99%).

The BHF-1 peptide was purified to homogeneity by high performance liquid chromatography on a reverse phase Vydac $C_4$ column (2.24×25 cm) using a linear gradient separation (2–98% B in 60 min) with a flow rate of 9 ml/min. Buffer A consisted of 0.1% trifluoroacetic acid (TFA)/Milli Q water and Buffer B consisted of 0.085% TFA/80% acetonitrile. The gradient was run at room temperature and absorbance monitored at 210 and 277 nm.

Fast atom bombardment-mass spectrometry gave a protonated molecular ion peak $(M+H)^+$ at m/z=2290.2, in good agreement with the calculated value. On amino acid analysis, experimental values for the relative abundance of each amino acid in the peptide were in good agreement with theoretical values. The lyophilized peptide was stored at −20° C.

Example 16

In Vitro Screening for Agents Which Inhibit Binding Between LDL and LBPs

This example illustrates in vitro screening for agents which inhibit binding between LDL and LBPs.

A candidate polypeptide for being an agent is chosen, e.g., LBP-1, LBP-2, LBP-3, BHF-1 or any other polypeptide. The shortest fragment of the polypeptide that inhibits LDL binding to LBPs in vitro is determined. Peptides are synthesized by standard techniques described herein. Inhibition assays are performed using standard ELISA techniques for screening, and affinity coelectrophoresis (ACE) assays to confirm the ELISA results, as described herein. Short peptides ranging, e.g., from dimers to 20-mers are constructed across sequences of the candidate polypeptide whose chemical characteristics make them likely LDL binding sites, e.g., acidic regions. The ability of shorter and shorter lengths of the peptides to inhibit LDL binding in vitro and to mammalian cells in culture is tested. For example, the effect of the peptide on inhibiting LDL binding in mammalian cells transfected to express an LBP gene is tested. Each of the peptides so identified as an inhibitor is tested with each of LBP-1, LBP-2 and LBP-3, to determine whether a single inhibitor works against all three LBPs.

Once the minimum active sequence is determined, the peptide backbone is modified so as to inhibit proteolysis, as discussed herein. For example, modification is accomplished by substitution of a sulfoxide for the carbonyl, by reversing the peptide bond, by substituting a methylene for the carbonyl group, or other similar standard methodology. See Spatola, A. F., "Peptide. Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267–357, B. Weinstein (ed.), Marcel Dekker, Inc., New York (1983). The ability of these analogs to inhibit LDL binding to the LBPs in vitro is tested by ELISA and ACE assays in a similar manner as for the natural peptides described above.

Example 17

In Vitro Screening With Cultured Mammalian Cells for Agents Which Inhibit Binding Between LDL and LBPs This example illustrates cell-based in vitro screening of agents which have been shown by in vitro tests such as ACE assay and ELISA to be potential inhibitors of binding between LDL and LBPs.

Mammalian cells, such as 293 cells, which are commonly used for expression of recombinant gene constructs, are used to develop cell lines which express LBPs on the cell surface. This is done by subcloning LBP open reading frames (ORFs) into a mammalian expression plasmid vector, pDisplay (Invitrogen, Carlsbad, Calif.), which is designed to express the gene of interest on the cell surface. The use of mammalian cells to produce LBPs allows for their expression in a functionally active, native conformation. Therefore, stably transfected mammalian cell lines with surface expression of LBPs individually, or in combination, are particularly suitable for assaying and screening inhibitors that block LDL binding in cell culture, as well as to evaluate the cytotoxicity of these compounds.

Specifically, LBP ORFs are amplified by PCR (Perkin Elmer, Foster City, Calif.) from cDNA templates using Taq polymerase (Perkin Elmer) and appropriate primers. The amplified LBP ORFs are purified by agarose gel electrophoresis and extracted from gel slices with the Bio-Rad DNA Purification kit (Bio-Rad, Hercules, Calif.). The purified DNAs are then cut with the restriction enzymes Bgl II and Sal I (New England Biolabs, Beverly, Mass.) to generate cohesive ends, and purified again by agarose gel electrophoresis and DNA extraction as described above. The LBP ORFs are then subcloned into the Bgl II/Sal I sites in the mammalian expression vector, pDisplay (Invitrogen) by ligation. Recombinant plasmids are established by transformation in E. coli strains TOP10 (Invitrogen) or DH5α (Life Technologies, Grand Island, N.Y.). Recombinant pDisplay/LBP plasmid DNA is isolated from overnight E. coli cultures with the Bio-Rad Plasmid Miniprep kit, cut with Bgl II/Sal I, and analyzed by agarose gel electrophoresis. LBP ORFs in successfully transformed clones are verified by automated dideoxy DNA sequencing. To transfect human kidney 293.cells, 1–2 µg of DNA is mixed with 6 µl lipofectamine reagent (Life Technologies) and incubated with the cells as described in the Life Technologies protocol. LBP expression in transfected cells is confirmed by Western blot analysis of cell extracts obtained 48 hr after transfection. To select for stably transfected 293 cells, the antibiotic G418 (Life Technologies) is added to the growth medium at a concentration of 800 µg/ml. Colonies resistant to G418 are tested for recombinant LBP expression by Western blot, and recombinant clones expressing LBPs are expanded, assayed for LDL binding and used to test compounds for their ability to inhibit LDL binding.

Example 18

In Vivo Screening for Agents Which Inhibit Binding Between LDL and LBPs

This example illustrates vivo screening of agents which have been shown by in vitro tests to be promising candidate inhibitors of binding between LDL and LBPs.

In vivo inhibitory activity is first tested in the healing balloon-catheter deendothelialized rabbit aorta model of arterial injury (Roberts et al., J. Lipid. Res. 24:1160–1167 (1983); Chang et al., Arterioscler. Thomb. 12:1088–1098 (1992)). This model was shown to be an excellent analog for human atherosclerotic lesions. Each candidate inhibitor is tested in five to ten ballooned rabbits, while an equal number of rabbits receive a control peptide, or placebo. Four weeks following aortic deendothelialization, when reendothelialization (healing) is partially complete, daily parenteral (intravenous or subcutaneous) or intragastric administration of the peptides and the analogs begins at an initial concentration of 10 mg/kg body weight, which is varied down, or up to 100 mg/kg depending on results. 30 min later, a bolus of intravenously injected $^{125}$I (or $^{99m}$Tc-) labeled LDL is given to test the candidate inhibitor's ability in short term studies to inhibit LDL sequestration in healing arterial lesions. If $^{125}$I-LDL is used, the animals are sacrificed 8–24 hr later, the aortas excised, washed and subjected to quantitative autoradiography of excised aortas, as previously described (Roberts et al., J. Lipid Res. 24:1160–1167 (1983); Chang et al., Arterioscler. Thomb. 12:1088–1098 (1992)). If $^{99m}$Tc-LDL is used, analysis is by external gamma camera imaging of the live anesthetized animal at 2–24 hr, as previously described (Lees and Lees, Syndromes of Atherosclerosis, in Fuster, ed., Futura Publishing Co., Armonk, N.Y., pp. 385–401 (1996)), followed by sacrifice, excision and imaging of the excised aorta. Immediately before the end of testing, the animals have standard toxicity tests, including CBC, liver enzymes, and urinalysis.

The compounds which are most effective and least toxic are then tested in short term studies of rabbits fed a 2% cholesterol diet (Schwenke and Carew, Arteriosclerosis 9:895–907 (1989)). Each candidate inhibitor is tested in five to ten rabbits, while an equal number of rabbits receive a control peptide, or placebo. Animals receive one or more doses per day of the candidate inhibitor, or placebo, for up to two weeks. Daily frequency of doses is determined by route of administration. If active drug or placebo are administered parenterally, they are given 1–3 times daily and the 2% cholesterol diet is continued. If drug or placebo are given orally, they are mixed with the 2% cholesterol diet. Schwenke and Carew (Arteriosclerosis 9:895–907 (1989)) have shown that the LDL concentration in lesion-prone areas of the rabbit aorta is increased 22-fold above normal in rabbits fed a 2% cholesterol diet for 16 days, and that the increased LDL content precedes the histological evidence of early atherosclerosis. Therefore, analysis of the effect of the candidate inhibitors is tested two weeks after the start of cholesterol feeding by injecting $^{125}$I-LDL, allowing it to circulate for 8–24 hr, and then performing quantitative autoradiography on the excised aortas of both test and control animals. If appropriate, quantitation of aortic cholesterol content is also carried out (Schwenke and Carew, Arteriosclerosis 9:895–907 (1989); Schwenke and Carew, Arteriosclerosis 9:908–918 (1989).

The above procedures identify the most promising candidate inhibitors, as well as the best route and frequency of their administration. Inhibitors so identified are then tested in long-term studies of cholesterol-fed rabbits. These tests are carried out in the same way as the short-term cholesterol feeding studies, except that inhibitor effectiveness is tested by injection of $^{125}$I-LDL at longer intervals following the initiation of cholesterol feeding, and lesion-prone areas of the aorta are examined histologically for evidence of atherosclerosis. Testing times are at two, four, and six months. Major arteries are examined grossly and histologically for evidence and extent of atherosclerosis. If necessary, other accepted animal models, such as atherosclerosis-susceptible primates (Williams et al., Arterioscler. Thromb. Vasc. Biol. 15:827–836 (1995) and/or Watanabe rabbits are tested with short and long-term cholesterol feeding.

Example 19

In Vivo Inhibition of Radiolabeled LDL Accumulation in the Ballooned Deendothelialized Rabbit Aorta via Induction of Active Immunity Against LBP Protein This example illustrates the effect that induction of immunity against LBP protein has on the accumulation of radiolabeled LDL in the ballooned deendothelialized rabbit aorta model of atherosclerosis.

Immunity was induced in male New Zealand White rabbits (Hazelton Research Products, Denver, Pa.) as follows: A mixture of purified human recombinant LBP-2 or BHF-1 peptide (1 ml; 1 mg) and RIBI adjuvant (RIBI ImmunoChem Research, Inc., Hamilton, Mont.) was injected subcutanously at 2–5 sites along the dorsal thoracic and abdominal regions of the rabbits. Blood was collected by venipuncture on days 1 (preimmune bleeding), 35, 63, and 91. Booster injections were administered on days 28 (5.00 µg; SC), 56 (250 µg; SC), and 84 (125 µg; SC).

The titer of the rabbits was evaluated by serial dilution using an ELISA plate format. Preimmune serum was evaluated at the same time. After the third booster of LBP protein or peptide, the titer reached a maximal level with a detectable calorimetric response on an ELISA plate of 156 pg. Titer is defined as the maximum dilution of antibody which generates an absorbance reading of 0.5 above control in 30 min. Specificity of the polyclonal antibodies was demonstrated using Western blot analysis as described in Example 6.

On day 93, the abdominal aorta of immunized and control rabbits was deendothelialized using a Fogarty number 4 embolectomy catheter (Chang et al., Arteriosclerosis and Thrombosis 12:1088–1098 (1992)). Four weeks after ballooning, rabbits received a bolus injection of $^{125}$I-labeled LDL (1 ml; i.v.). Blood samples were collected at 1 hr intervals for 8 hr, and 24 hr post injection. Blood samples were centrifuged for 30 min at 2000 rpm (40° C.) and total activity present in the serum was determined using a Gamma counter. Total TCA precipitable counts were determined by addition of TCA to the serum to a final concentration of 10% followed by incubation for 10 min at 4° C. Serum samples were then centrifuged (2000 rpm; 30 min; 40° C.) and total activity present in the supernate was determined. TCA precipitable counts were calculated by substration: total soluble counts minus counts present in the supernate after TCA precipitation. Blood samples for the determination of antibody titers were collected prior to the injection of the radiolabeled LDL.

After 24 hr, the rabbits were injected intravenously with 5% Evan's blue dye which was allowed to circulate for 15 min. Areas of the aorta in which the endothelial covering is absent stain blue while those areas covered by endothelium remain unstained. At the end of the incubation period, the rabbits were euthanized and the abdominal and thoracic aorta were dissected out, rinsed, and fixed overnight in 10% TCA at room temperature. The aortas were then rinsed exhaustively with physiological saline, weighed, counted, blotted dry and placed onto X-ray film in order to visualize the pattern of radiolabeled LDL accumulation in the deendothelialized rabbit abdominal aorta.

Immunization of rabbits against recombinant human LBP-2 or BHF-1 peptide altered the pattern of radiolabeled LDL accumulation in the ballooned deendothelialized abdominal aorta. When corrected for dosage, and percent reendothelialization, immunized-ballooned rabbits had lower accumulation of radiolabeled LDL compared to nonimmune-ballooned rabbits. These results indicate that active immunization against LBP provides an effective means by which the accumulation of LDL in the injured arterial wall can be modified.

Example 20

Screening Agents in Humans Which Inhibit Binding Between LDL and LBPs

Human studies are carried out according to standard FDA protocols for testing of new drugs for safety (Phase I)

efficacy (Phase II), and efficacy compared to other treatments (Phase III). Subjects, who are enrolled into studies after giving informed consent, are between the ages of 18 and 70. Women who are pregnant, or likely to become pregnant, or subjects with diseases other than primary atherosclerosis, such as cancer, liver disease, or diabetes, are excluded. Subjects selected for study in FDA Phase II and Phase III trials have atherosclerotic disease previously documented by standard techniques, such as ultrasound and/or angiography, or are known to be at high risk of atherosclerosis by virtue of having at least one first degree relative with documented atherosclerosis. Subjects themselves have normal or abnormal plasma lipids. Initial testing includes 20–50 subjects on active drug and 20–50 subjects, matched for age, sex, and atherosclerotic status, on placebo. The number of subjects is pre-determined by the number needed for statistical significance. Endpoints for inhibitor efficacy includes ultrasound measurements of carotid artery thickness in high risk subjects, as well as in subjects with known carotid or coronary disease; atherosclerotic events; atherosclerotic deaths; and all-cause deaths in all subjects. Non-invasive analysis (carotid artery thickness by ultrasound) as per Stadler (Med. and Biol. 22:25–34 (1996)) are carried out at 6-to 12-month intervals for 3 years. Atherosclerotic events and deaths, as well as all-cause deaths are tabulated at 3 years.

Oral dosage of drug in FDA Phase I trials ranges from 0.01 to 10 gm/day, and is determined by results of animal studies, extrapolated on a per kg basis. Based on data obtained from Phase I studies, the dose range and frequency are narrowed in Phase II and III trials. If parenteral administration of drug is determined by animal studies to be the only effective method, parenteral administration in human subjects is tested by injection, as well as by the transdermal and nasal insufflation routes. Testing of parenteral drug follows the same outline as that for oral administration.

The optimal treatment schedule and dosage for humans is thus established.

Example 21

Treating an Individual Having Atherosclerosis With BHF-1

This example illustrates a method for treating an individual having atherosclerosis with an LBP fragment, e.g., BHF-1, so as to decrease the levels of arterially bound LDL in the individual. BHF-1 is obtained as described herein. The BHF-1 is administered to the mammal intravenously as a bolus or as an injection at a concentration of 0.5–10 mg/kg body weight. Such administrations are repeated indefinitely in order to prevent the development or progression of symptomatic atherosclerosis, just as is done currently with cholesterol-lowering drugs. Stable subjects are examined twice yearly to evaluate the extent of any atherosclerotic disease by physical exam and non-invasive studies, such as carotid artery thickness, ultrasound, and/or gamma camera imaging of the major arteries, to determine if atherosclerotic lesions are present, and, if previously present, have regressed or progressed. Such a regimen results in treatment of the atherosclerosis.

Those skilled in the art will be able to ascertain using no more than routine experimentation, many equivalents of the specific embodiments of the invention described herein. These and all other equivalents are intended to be encompassed by the following claims.

Other Embodiments

In Vivo Reduction of Atherosclerosis in Hyperlipidemic Mice by Immunization with LBPs Separate immunization experiments were performed with each of LBP-1, LBP-2, and LBP-3. Immunity was induced by injecting apo E knockout mice with the LBP protein (LBP-1, LBP-2, or LBP-3) together with an RIBI adjuvant (RIBI ImmunoChem Research, Inc., Hamilton, Mont.). Apo E knockout mice (Jackson Laboratories, Bar Harbor, Me.) are hyperlipidemic and thus a model for human atherosclerosis. Apo E knockout mice have high levels of plasma cholesterol and develop naturally-occurring atherosclerotic-like lesions.

Four week old apo E knockout mice (Jackson Laboratories, Bar Harbor, Me.) were ear tagged, randomly assigned to different cages and weighed. Body weights were determined weekly. Animals were allowed to habituate for 1 week. Normal rodent chow was provided ad libitum and animals were maintained in a 12:12 light:dark cycle. The following four groups of mice were treated with either recombinant LBP proteins (40 g of recombinant protein/mouse) plus RIBI adjuvant or RIBI adjuvant alone (control group).

LBP-1: Immunized with rabbit recombinant LBP-1 (6-His tag).

LBP-2: Immunized with rabbit recombinant LBP-2 clone 26 (6-His tag).

LBP-3: Immunized with rabbit recombinant LBP-3 (6-His tag).

Control: Received adjuvant.

Blood samples (pre-immune serum) were collected prior to the initial injection of recombinant protein and RIBI adjuvant (as described in the manufacturer's manual). After 21 days, mice received a booster injection (half-initial dose) and were then bled seven days later. Titer was defined as the maximum dilution of serum that yielded a change in absorbance equivalent to 2× that of control serum (60 min; 37° C.). The amount of recombinant protein per well was 100 ng.

Booster injections took place at 21 day intervals until an average titer value of 1:10,000 was reached. At this time, mice were switched to western type diet (Harland Teklad, Madison, Wis.) and fed ad libitum. Blood samples were collected at this time (retro-orbital sinus bleeding technique) and monthly thereafter.

Blood samples were analyzed for total cholesterol, HDL cholesterol, and triglyceride concentration with a commercially available total cholesterol and triglycerides assay kits (Sigma; St. Louis Mo.) using an ELISA format. HDL concentration was determined after Apo B containing lipoproteins were precipitated using heparin/$MnCl_2$.

Apo E knockout mice were sacrificed at 26 weeks of age. The mice were anesthetized with methoxyfluorane and exanguinated via cardiac puncture. A midline thoracotomy was performed, a cannula inserted into the right ventricle and perfusate allowed unrestricted flow via an incision into the right atrium. The mice were perfused with saline, followed by 10% phosphate buffered formalin until fasciculations stopped. At this time, the aorta was exposed and adventitial fat removed in situ. The aorta was then removed from the heart down to the iliac bifurcation and placed in 10% phosphate buffered formalin overnight.

The aorta was stained as follows: after a brief 70% ethanol rinse, it was immersed in a filtered solution of 0.5% (weight/volume) Sudan IV in 35% ethanol/50% acetone with continuous shaking for 10 minutes at room temperature. Unbound dye was removed by incubating the aorta in an 80% ethanol solution with shaking until the background color was clear. The vessel was then rinsed in distilled water, placed in physiological saline and opened longitudinally from the aortic arch down to the iliac bifurcation. The vessel was pinned out and photographed. Photographs were then digitized using an Astra 1200S scanner (UMAX Technologies Inc., Freemont, Calif.) and a commercially available graphics program (Canvas; Deneba Software, Miami Fla.). Total and lesion areas were determined using the signal processing toolbox of MATLAB (The Mathworks Inc., Natick, Mass.). Percent involvement was calculated by dividing lesion area by total area.

A second analysis was done to measure aortic atherosclerosis by a cholesterol extraction method whereby cholesterol is determined as a unit weight of artery. This method may be more accurate in measuring lesion size than attempting to measure the thickness of many sections. Specifically, the weight of an artery was measured, then the cholesterol was extracted. Aortic cholesterol content was then measured by gas-liquid chromatography. The amount of cholesterol per unit weight of artery was then determined.

After the first booster injection, some of the apo E knockout mice immunized against LBP-1 had relatively high anti-LBP-1 titers ($\leq 1:5000$) while others in the same group exhibited moderate levels (>1:500 to <1:1000). LBP-2/26 titers were low in the apoE knockout mice (<1:500) at this time. LBP-3 titers ranged from moderate to low ($\geq 1:500$ to<1:1000) to low (<1:500) in the apoE knockout mice.

After the second booster injection, Apo E knockout mice immunized against LBP-1 had moderate to high titers (>1:1000 to $\leq 1:8000$). Apo E knockout mice immunized against LBP-2/26 had moderate titer levels (>1:2000). LBP-3 titers range from moderate to high (>1:1000 to >1:8000) in the Apo knockout mice.

After the third booster injection, most of the mice immunized against LBP-1 had relatively high titers (>1:10,000) while others had moderate to high titers (>1000 to <1:10,000). Some of the Apo E knockout mice had moderate (<1:5000) to low (<1:1000) titers. LBP-3 titers ranged from high (>1:5000 to $\leq 1:10,000$) to moderate (>1:1000 to <1:5000).

Data were analyzed using T-tests and Wilcoxons. Immunization against LBP-1, LBP-2/26 or LBP-3 did not have a significant effect (P>0.05) on body weight of Apo E knockout mice. Due to the small sample size and the large variability present in the Apo E knockout mice, it was not possible to determine whether immunization against LBP-1, LBP-2/26 or LBP-3 had an effect on total cholesterol, HDL cholesterol or triglycerides concentration, but it did not appear to.

Immunization against LBP-1 or LBP-3 did not have a significant effect (P>0.05) on lesions of the apo E knockout mice or LDL receptor negative knockout mice. However, immunization of the apo E knockout mice against LBP-2 had a significant effect on lesion area (Table 1), and, once outliers were deleted, a significant effect on arterial wall cholesterol content (Table 2). The LBP-2 immunized apo E knockout mice had significantly reduced aortic atherosclerosis as compared to the control, non-immunized mice. Without being bound to any particular theory, the circulating antibodies generated against LBP-2 proteins are thought to block LDL binding to the artery wall.

TABLE 1

Lesion Area in LBP-Immunized Apo E Mice

| Apo E Mice | Lesion Area % Coverage | Treated Area Change | P-Value Wilcoxon |
|---|---|---|---|
| Control | 9.40 | | |
| LBP-1 | 6.05 | −0.36% | 0.07 |
| LBP-2 | 6.01 | −0.36% | 0.01 |
| LBP-3 | 7.14 | −0.24% | 0.36 |

TABLE 2

Arterial Cholesterol Content in LBP-Immunized Apo E Mice

| Apo E Mice | Arterial Wall Cholesterol (ug cholesterol/mg aorta) | Treated Area Cholesterol Change | P-Value Wilcoxon |
|---|---|---|---|
| Control | 6.33 | | |
| LBP-1 | 3.82 | −0.40% | 0.14 |
| LBP-2 | 3.28 | −0.48% | 0.07 |
| LBP-2 (outliers deleted) | 1.83 | −0.71% | 0.01 |
| LBP-3 | 4.48 | −0.29% | 0.20 |

Immunotherapeutic Products

These experiments demonstrate that atherosclerosis in a hyperlipidemic subject can be reduced following the generation of an immune response in the subject by immunization with LBPs. Numerous immunotherapeutic products can be used to generate antibodies that will block the binding between LDL and LBPs.

The injection of one or more LBPs can result in the production of anti-LBP antibodies, resulting in a reduction in aortic atherosclerosis. This effect is thought to be mediated by an inhibition of LBP binding to LDL. LBP immunogens that can be used in the invention include human LBPs, non-human LBPs, recombinant LBPs, and proteins structurally related to the LBPs described herein, e.g. non-naturally occurring proteins that differ from a naturally occurring LBP at one or more amino acid residues. In addition to full length proteins, injecting one or more peptides that include an LBP domain can generate an effective immune response. For example, the injection of a peptide comprising an LBP domain having LDL-binding activity can cause an organism to make antibodies to the LBP binding sites for LDL. These peptide immunogens can include sequences derived from human LBPs, non-human LBPs, recombinant LBPs, and proteins structurally related to the LBPs described herein.

Modifications can be made to a protein or peptide immunogen of the invention to increase its immunogenicity. The immunogen can be conjugated or coupled with a carrier, e.g. a Cholera toxin B chain or monoclonal antibodies. The immunogen can be precipitated with aluminum salts or cross-linked with formaldehyde or other aldehydes. The protein may be mixed with a physiologically acceptable diluent such as water, phosphate buffered saline, or saline. The composition may further include an adjuvant. In addition to RIBI adjuvant, adjuvants such as incomplete Freund's adjuvant, aluminum phosphate, aluminum hydroxide are all well known in the art. Adjustments in the adjuvant of the invention can be made to affect the immunogenicity of the peptide or protein. Examples of such modifications include using: aluminum salts; cytokines; MF59 (microfluidized emulsion of oil and surfactants); SAF-1 (oil-based emulsion); saponin derivatives; polymers (such as polyphosphazene); and bacterial toxins. Additional descriptions of antigenic protein-adjuvant combinations are described in WO 99/54452 (herein incorporated by reference) and WO 99/49890 (herein incorporated by reference).

In addition to delivery of the proteins and peptides described above, numerous other delivery systems can be used to generate the anti-atherosclerotic immunity of the invention. The LBP immunogen can be delivered either directly as a protein antigen or alternatively as a nucleic acid that encodes the protein antigen. The immunotherapeutic products of the invention, either protein or nucleic acid, can be delivered by numerous delivery routes. These include injection, deposition, implantation, suppositories, oral ingestion, inhalation (e.g., delivery via a nasal spray), and topical administration (e.g., delivery via a skin patch).

A nucleic acid encoding an immunogen of the invention can be directly administered, for example by injection, to tissues and expressed as a protein. The DNA or RNA can be either associated with a delivery vehicle (e.g., viruses, bacteria, liposomes, and gold beads) or naked (free from association with transfection-facilitating proteins, viral particles, liposomal formulations, charged lipids and calcium phosphate precipitating). The nucleic acid can optionally include a promoter, e.g. a viral promoter. The immunogen encoded by the nucleic acid is produced in the host, resulting in the generation of an immune response. Methods for the delivery of nucleic acid sequences encoding therapeutic proteins and peptides are described in detail by Felgner et al. (U.S. Pat. No. 5,580,859; herein incorporated by reference) and Barbet et al. (U.S. Pat. No. 6,025, 338; herein incorporated by reference). Vaccine compositions of viral liposomes comprising a nucleic acid, e.g. an RNA, encoding a protein antigen are described in WO 99/52503 (herein incorporated by reference). Proteins and nucleic acids encoding peptides can also be delivered to an individual by their encapsulation in liposomes, microparticles, and ISCOMS, all of which are well known in the art (see, e.g., U.S. Pat. No. 6,013,258, herein incorporated by reference).

A nucleic acid encoding an immunogen of the invention can also be included in the genome of a plant, so as to result in the production of the immunogen by plant tissues. The genetically modified plant may then consumed by an individual, resulting in the ingestion of the immunogen and the generation of an anti-LBP immune response. Methodology for the generation and usage of edible plant vaccines is described in WO 99/54452 (herein incorporated by reference).

Numerous plants may be useful for the production of an edible vaccine, including: tobacco, tomato, potato, eggplant, pepino, yam, soybean, pea, sugar beet, lettuce, bell pepper, celery, carrot, asparagus, onion, grapevine, muskmelon, strawberry, rice, sunflower, rapeseed/canola, wheat, oats, maize, cotton, walnut, spruce/conifer, poplar and apple. The edible vaccine can include a plant cell transformed with a nucleic acid construct comprising a promoter and a sequence encoding an LBP. The sequence may optionally encode a chimeric protein, comprising a cholera toxin subunit B peptide fused to the LBP peptide. Preferred plant promoters of the invention include CaMV 35S, patatin, mas, and granule-bound starch synthase promoters. Additional useful promoters and enhancers are described in WO 99/54452.

The edible vaccine of the invention can be administered to a mammal suffering from or at risk of atherosclerosis. Preferably, an edible vaccine is administered orally, e.g. consuming a transgenic plant of the invention. The transgenic plant can be in the form of a plant part, extract, juice, liquid, powder, or tablet. The edible vaccine can also be administered via an intranasal route.

Microorganisms, e.g., attenuated viruses or bacteria, can be used in the invention by including a nucleic acid encoding an LBP immunogen in the genome of the microorganism. This modified vector can then be delivered to a host, resulting in the in vivo production of the immunogen. The immune response generated by these vectors is expected to result in anti-atherosclerotic immunity. Nucleic acid molecules are inserted into microorganism genomes by standard methods known in the art (U.S. Pat. No. 5,866,136 and U.S. Pat. No. 6,025,164, both of which are herein incorporated by reference).

The anti-atherosclerotic methods of the invention are directed to treating a subject, e.g., a human, primate, horse, dog, cat, or goat, at risk for atherosclerosis by stimulating an anti-LBP response in the subject by immunotherapy. The LBP proteins and peptides of the invention may be delivered to the subject by the numerous delivery systems described herein. The immunotherapy may comprise an initial immunization followed by additional, e.g. one, two, or three, boosters.

Also provided by the invention is a method of treating a subject at risk for atherosclerosis whereby a non-autologous LBP protein is delivered to the subject to generate an immune response to an autologous LBP. Specifically, this method entails identifying one or more autologous LBP proteins, e.g., LBP-1, LBP-2, or LBP-3, produced by the subject. The identification can by, e.g., DNA sequence analysis, protein sequence analysis, antibody reactivity, hybridization analysis, or nucleic acid amplification. Next, a non-autologous LBP protein, e.g., allogeneic, xenogeneic, or a genetically modified, non-naturally occurring protein that differs at one or more amino acid residues from the one or more LBP proteins is administered to the subject. The anti-atherosclerotic effectiveness of this immunotherapeutic product is determined by its ability to induce an immune response against one or more autologous LBP proteins when administered to the subject. It is therefore expected that extensive differences between a non-autologous and autologous LBP protein will not result in cross immunoreactivity.

Another method of the invention is a method of treating a subject at risk for atherosclerosis by increasing the levels of LBP circulating in the plasma. According to this method, either autologous or non-autologous LBP levels may be increased. Because LBP generally does not normally occur as a circulating protein, the endogenous molecule is expected to be susceptible to immune recognition when delivered in a soluble form.

Also included in the invention is a cell therapy system, whereby a cell expressing an LBP is delivered to a subject at risk for atherosclerosis. This cell can be engineered to express either an autologous or non-autologous LBP protein or peptide of the invention. Delivery of this engineered cell to a subject results in the in vivo production of an LBP protein and the associated immunotherapy produced when either the protein or a nucleic acid encoding the protein is provided to an individual. Cell therapy methods are described in U.S. 5,955,095 (herein incorporated by reference).

What is claimed is:

1. A method of treating a subject having atherosclerosis or at risk for having atherosclerosis, the method comprising:
   providing a subject having atherosclerosis or at risk for having atherosclerosis; and
   administering to the subject a polypeptide and an adjuvant, wherein the polypeptide comprises the amino acid sequence of SEQ ID NO:6 or an immunogenic fragment of the amino acid sequence of SEQ ID NO:6.

2. The method of claim 1, further comprising diagnosing the subjects as having atherosclerosis or being at risk for having atherosclerosis.

3. The method of claim 1, wherein the polypeptide comprises the amino acid sequence of SEQ ID NO:6.

4. The method of claim 1, wherein the polypeptide consists of the amino acid sequence of SEQ ID NO:6.

5. The method of claim 1, wherein the polypeptide comprises SEQ ID NO:9.

6. The method of claim 1, wherein the polypeptide comprises SEQ ID NO:23.

7. The method of claim 1, wherein the polypeptide comprises SEQ ID NO:24.

8. The method of claim 1, wherein the polypeptide consists of the amino acid sequence of SEQ ID NO:9.

9. The method of claim 1, further comprising diagnosing the subject as having atherosclerosis.

10. The method of claim 9, wherein the polypeptide comprises the amino acid sequence of SEQ ID NO:6.

11. The method of claim 9, wherein the polypeptide consists of the amino acid sequence of SEQ ID NO:6.

12. The method of claim 9, wherein the polypeptide comprises the amino acid sequence of SEQ ID NO:9.

13. The method of claim 9, wherein the polypeptide consists of the amino acid sequence of SEQ ID NO:9.

14. The method of claim 9, wherein the polypeptide comprises the amino acid sequence of SEQ ID NO:23.

15. The method of claim 9, wherein the polypeptide comprises the amino acid sequence of SEQ ID NO:24.

16. A pharmaceutical composition comprising a polypeptide mixed with an adjuvant, suitable for use in humans, wherein the polypeptide comprises the amino acid sequence of SEQ ID NO:6, SEQ ID NO:9, SEQ ID NO:23, or SEQ ID NO:24.

17. The pharmaceutical composition of claim 16, wherein the polypeptide comprises the amino acid sequence of SEQ ID NO:6.

18. The pharmaceutical composition of claim 16, wherein the polypeptide comprises SEQ ID NO:9.

19. The pharmaceutical composition of claim 16, wherein the polypeptide comprises SEQ ID NO:23.

20. The pharmaceutical composition of claim 16, wherein the polypeptide comprises SEQ ID NO:24.

21. The pharmaceutical composition of claim 16, wherein the polypeptide consists of the amino acid sequence of SEQ ID NO:6.

22. The pharmaceutical composition of claim 16, wherein the polypeptide consists of the amino acid sequence of SEQ ID NO:9.

* * * * *

UNITED STATES PATENT AND TRADEMARK OFFICE
CERTIFICATE OF CORRECTION

PATENT NO. : 6,605,588 B1
DATED : August 12, 2003
INVENTOR(S) : Ann M. Lees et al.

It is certified that error appears in the above-identified patent and that said Letters Patent is hereby corrected as shown below:

Column 95,
Line 45, replace "or an immunogenic fragment of the amino acid sequence of SEQ ID NO:6" with -- , SEQ ID NO:9, SEQ ID NO:23, or SEQ ID NO:24 --.

Signed and Sealed this

Seventh Day of June, 2005

JON W. DUDAS
*Director of the United States Patent and Trademark Office*